(12) United States Patent
Withers et al.

(10) Patent No.: US 11,608,353 B2
(45) Date of Patent: Mar. 21, 2023

(54) AMYLASE INHIBITOR COMPOUNDS, METHODS OF THEIR USE AND COMPOSITIONS THEREOF

(71) Applicant: THE UNIVERSITY OF BRITISH COLUMBIA, Vancouver (CA)

(72) Inventors: Stephen G. Withers, Vancouver (CA); Gary D. Brayer, Richmond (CA); Leslie Karen Williams, Surrey (CA); Xiaohua Zhang, Montreal (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 327 days.

(21) Appl. No.: 16/675,535

(22) Filed: Nov. 6, 2019

(65) Prior Publication Data

US 2020/0079810 A1 Mar. 12, 2020

Related U.S. Application Data

(62) Division of application No. 15/661,883, filed on Jul. 27, 2017, now abandoned.

(60) Provisional application No. 62/367,360, filed on Jul. 27, 2016.

(51) Int. Cl.
| | |
|---|---|
| *A61K 31/7034* | (2006.01) |
| *A61K 31/7048* | (2006.01) |
| *A61K 31/7032* | (2006.01) |
| *C07H 15/26* | (2006.01) |
| *C07C 33/26* | (2006.01) |
| *C07D 311/30* | (2006.01) |
| *C07H 15/203* | (2006.01) |
| *A23G 4/12* | (2006.01) |
| *A23L 33/105* | (2016.01) |
| *C07H 1/06* | (2006.01) |

(52) U.S. Cl.
CPC ............ *C07H 15/26* (2013.01); *A23G 4/12* (2013.01); *A23L 33/105* (2016.08); *A61K 31/7032* (2013.01); *A61K 31/7034* (2013.01); *A61K 31/7048* (2013.01); *C07C 33/26* (2013.01); *C07D 311/30* (2013.01); *C07H 1/06* (2013.01); *C07H 15/203* (2013.01); *A23V 2002/00* (2013.01); *A23V 2200/312* (2013.01); *A23V 2200/328* (2013.01); *A23V 2250/2116* (2013.01)

(58) Field of Classification Search
None
See application file for complete search history.

(56) References Cited

FOREIGN PATENT DOCUMENTS

| CN | 101538296 | * | 9/2009 | ............ A61K 36/11 |
|---|---|---|---|---|
| WO | 2009049428 A1 | | 4/2009 | |
| WO | 2009064485 A1 | | 5/2009 | |
| WO | 2012061958 A1 | | 5/2012 | |

OTHER PUBLICATIONS

Asada, Yoshihisa, et al., "Acylated Flavonols from Crocosmia Crocosmiiflora." Phytochemistry, 1988, 27(5): 1497-1501.
Brasseur, Thierry, et al., "Sex Flavonol Glycosides from Leaves of Strychnos Variabilis." Phytochemistry, 1988, 27(5): 1487-1490.
Karl, Christian, et al., "A New Acylated Kaempferol Glycoside from Phyllitis Scolopendrium." Z Naturforsch, Jun. 19, 1980, 35c: 826-828.
Lee, Joon Yeol, et al., "Design and Synthesis of Novel Antidiabetic Agents." Arch Pharm Res, 2005, 28(2): 142-150.
Moharram, F.A., et al., "Antioxidant galloylated flavonol glycosides from Calliandra haematocephala." Natural Product Research, Aug. 2006, 20(10): 927-934, DOI: 10.1080/14786410500378494.
Sanz, Maria-Jesus, et al., "A New Quercetin-Acylglucuronide From Scolymus Hispanicus." Journal of Natural Products, Nov. 1993, 56(11): 1995-1998.
Williams, Leslie K., et al., "The amylase inhibitor montbretin A reveals a new glycosidase inhibition motif." Nature Chemical Biology, Sep. 2015, 11: 691-698.
Yuan, Jian, et al., "Synthesis of methylated quercetin derivatives and their reversal activities on P-gp- and BCRP-mediated multidrug resistance tumour cells." European Journal of Medicinal Chemistry, Apr. 2012. 54: 413-422.

* cited by examiner

*Primary Examiner* — Traviss C McIntosh, III
(74) *Attorney, Agent, or Firm* — Saliwanchik, Lloyd & Eisenschenk

(57) ABSTRACT

There are provided compounds of Formula I:

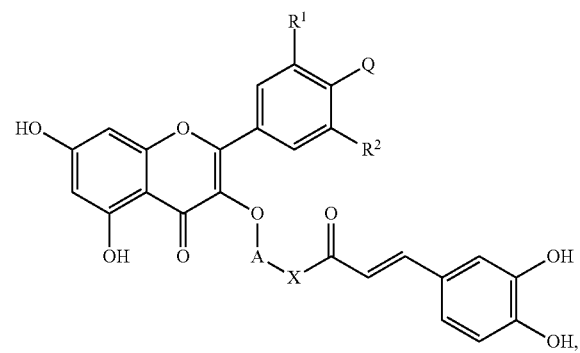

various compositions thereof and methods for their use in the inhibition of α-amylase.

16 Claims, 12 Drawing Sheets

FIGURE 4B MbA solution conformation
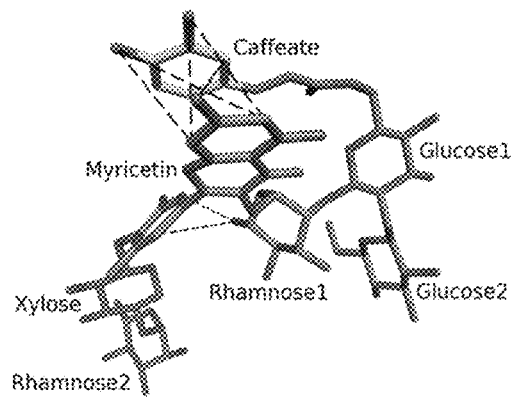
FIGURE 4C MbA conformation bound to HPA
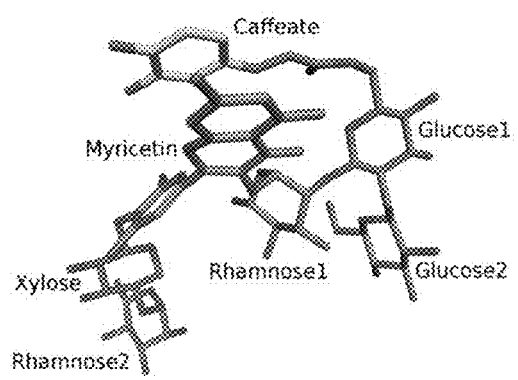
FIGURE 5B
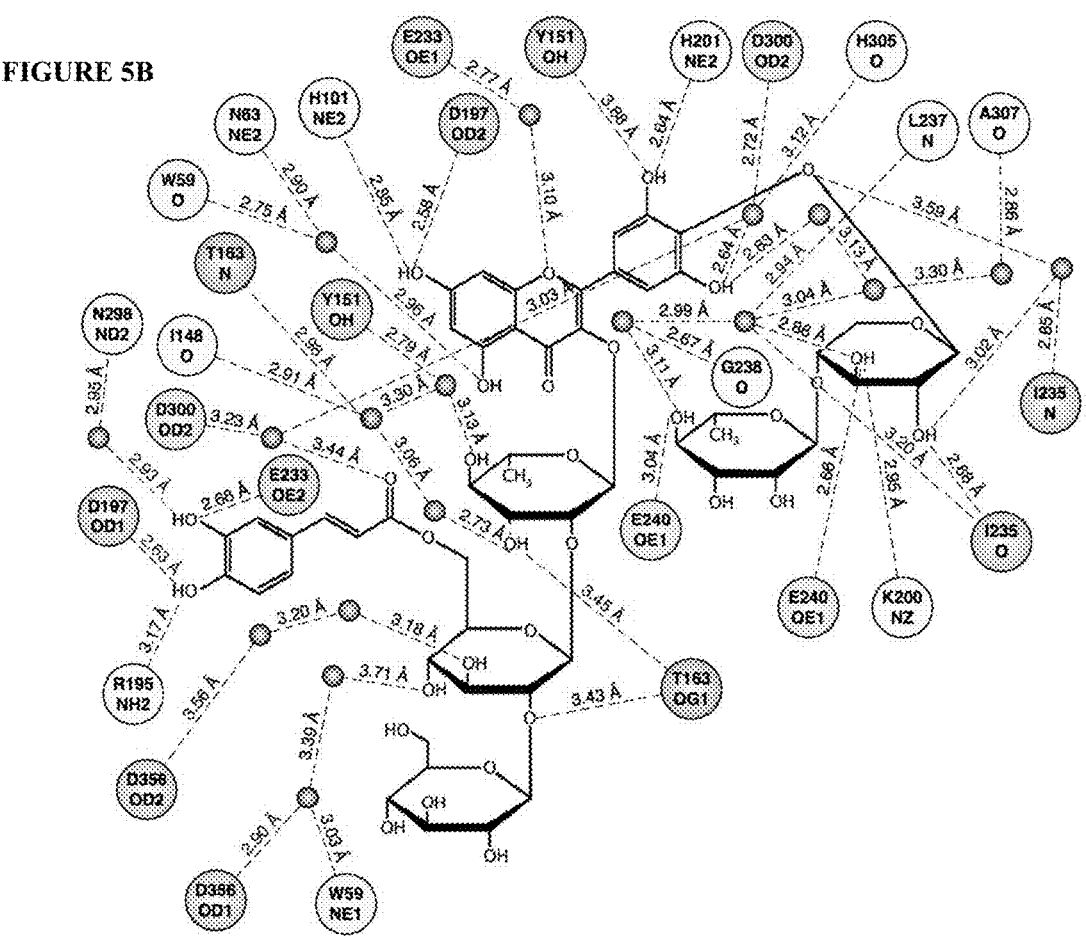

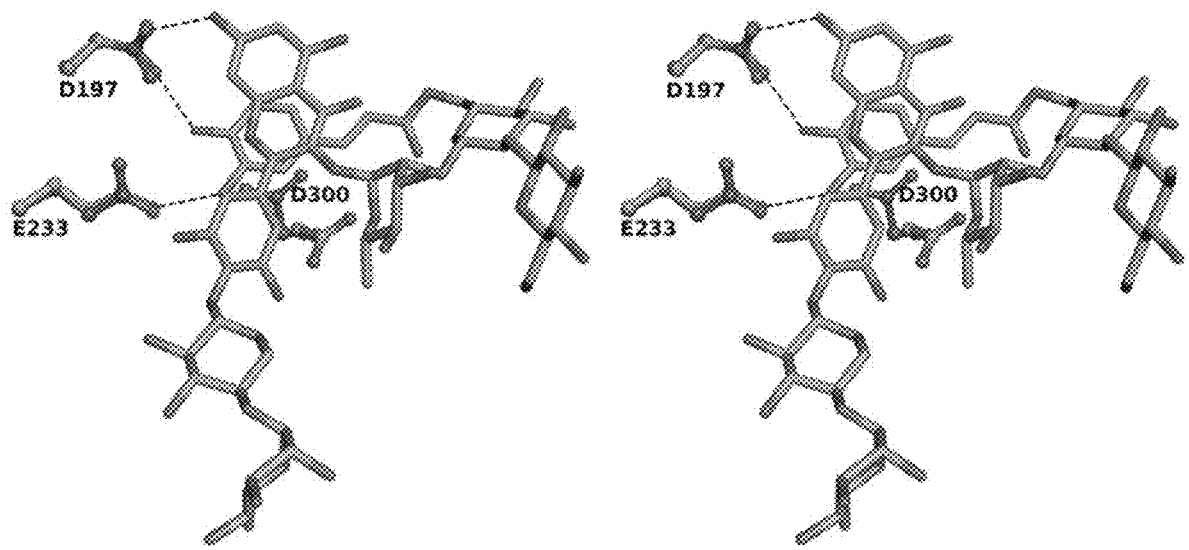
FIGURE 8A MbA Complex and Ligand-Free HPA
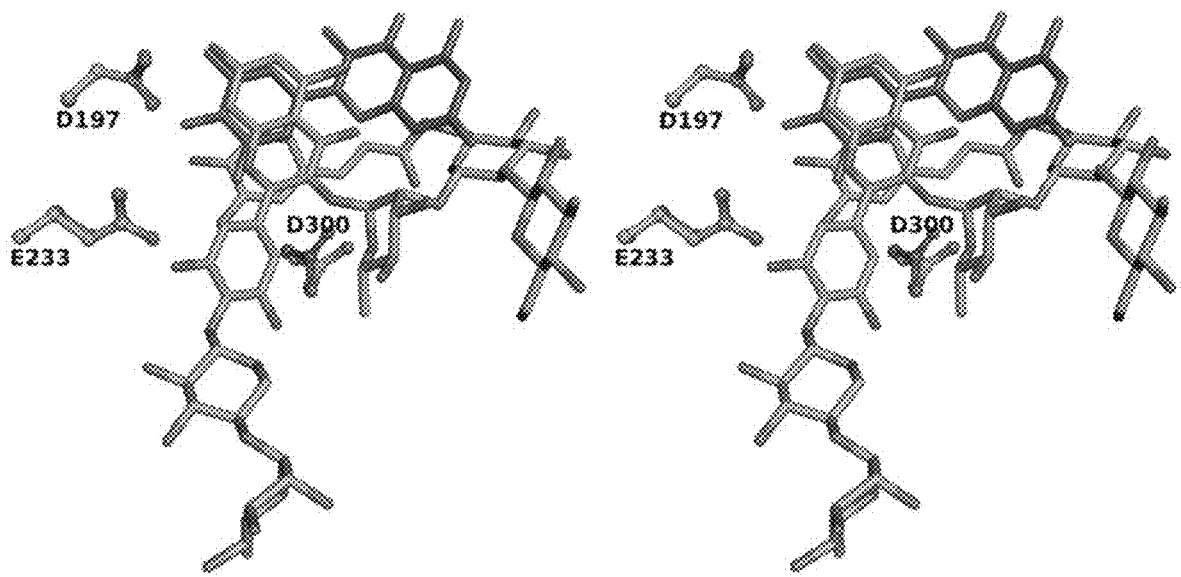
FIGURE 8B MbA and Myricetin Complexes

AMYLASE INHIBITOR COMPOUNDS, METHODS OF THEIR USE AND COMPOSITIONS THEREOF

CROSS REFERENCE TO RELATED APPLICATIONS

This application is a divisional application of U.S. application Ser. No. 15/661,883, filed on Jul. 27, 2017; which claims the benefit of U.S. Provisional Patent Application Ser. No. 62/367,360 filed on 27 Jul. 2016 entitled "AMYLASE INHIBITORS".

FIELD OF INVENTION

The present invention relates to compounds, methods and compositions for the inhibition of amylase. The present invention further provides compounds, methods and compositions for the inhibition of inhibition of mammalian salivary or pancreatic α-amylase for the treatment or prophylaxis of dental caries and/or plaque or for the treatment or prophylaxis of pre-diabetes, diabetes and/or obesity.

BACKGROUND

Human pancreatic α-amylase (HPA) is an endoglycosidase that cleaves the α-1,4 linked glucose molecules within starch to produce maltose and a range of additional small α-1,4 and α-1,6-linked oligosaccharides that are then further broken down into glucose by other glycosidases in the gut. Since this enzyme initiates the process of starch digestion, HPA activity can be directly correlated with blood glucose levels, and its inhibition, along with that of the mammalian gut alpha-glucosidases, is used to treat non-insulin dependent diabetes (2-4). Several α-glucosidase inhibitors, acarbose, miglitol and voglibose, have all been used clinically for the treatment of Type II diabetes, but have disagreeable side effects that interfere with patient compliance (2). This is thought to be due to binding of these inhibitors to the human gut α-glucosidases, which in turn means that normally digested small oligosaccharides are allowed to reach the colon where they can be fermented by bacteria, thereby producing bloating, flatulence and diarrhea (2). Clearly, new inhibitors of greater affinity and specificity for HPA are needed to prevent this currently observed side effect profile.

Screening of HPA with natural extracts has revealed just such a new class of inhibitor that appears to bind both strongly and with exquisite specificity to HPA (5). This family of inhibitors can be isolated from an extract of the corms of *Crocosmia crocosmiflora*, and of the five isoforms (A-E) found, the most potent is montbretin A (MbA). When tested in a diabetic rat model, MbA was shown to be superior to other inhibitors in reducing postprandial glucose spiking and in delaying the onset of diabetes (McNeill, unpublished data).

Montbretin A is a water soluble glycosylated flavonol that binds to HPA with a $K_I$ of 8 nM (5). It consists of a myricetin core attached to two carbohydrate chains at the $O_3$ of the benzopyrone and the C4' of the phenyl moieties. One chain is made up of a xylose and a rhamnose, while the other contains another rhamnose, and two glucoses. A caffeic acid moiety is also attached to the C6 of the first glucose in the chain. This caffeic acid moiety plays a key role in the inhibition of HPA since substitution of even one of its hydroxyl groups to either a hydrogen or a methoxy group produces an inhibitor that is almost a thousand-fold weaker (5).

Previously, many smaller and differently substituted flavonols have been shown to be inhibitors of HPA, although all of these demonstrate considerably weaker affinity and specificity than MbA for this enzyme (6-8). Indeed, the myricetin core of montbretin A is, by itself, an α-glucosidase inhibitor that exhibits a $K_I$ of 110 μM against HPA using a competitive inhibition model (5). Furthermore, the caffeate extension of MbA has also been shown to be an HPA inhibitor with a $K_I$ of 1.3 mM.

SUMMARY OF THE INVENTION

Montbretin A is a highly glycosylated flavonol with unprecedented inhibitory activity and specificity for human pancreatic α-amylase. To define the functional features that lead to these extraordinary characteristics, both substructure kinetic and high resolution X-ray structural analyses of the montbretin A human amylase inhibitory complex have been completed. Surprisingly, a key element in inhibitor activity was found to be the self-association of an internal π-stacking interaction between its myricetin and ethyl caffeate groups. Further ROSEY NMR studies suggest this core structure conformation is largely preformed in solution before montbretin A binds in the active site of human amylase. Substructure analyses confirm that a simpler molecule containing the myricetin and ethyl caffeate groups linked via their bridging glucose and rhamnose sugars, could by itself be a very effective inhibitor of human amylase. Structural studies show that montbretin A utilizes a completely different mode of HPA inhibition from that observed for substrate-like transition state mimics like acarbose. Montbretin A inhibitory activity involves the perpendicular insertion of the hydrophobic π-stacked core of montbretin A directly into the catalytic center of human amylase, with the ring hydroxyls of the myricetin and ethyl caffeate groups hydrogen bonding to the catalytic residues D197 and E233, while at the same time displacing other essential substrate binding elements. The central hydrophobic core of montbretin A is further tightly held in place by an extensive array of hydrogen bonds and hydrophobic interactions formed by peripheral sugar groups to the surface of human amylase. Notably, however, none of these peripheral sugars occupy the normal substrate binding subsites found in the extended human amylase substrate binding cleft. These results clearly demonstrate that montbretin A represents a new class of human amylase inhibitor, whose unique characteristics make this inhibitor potentially useful as a therapeutic to control blood glucose levels in diabetes and obesity. Furthermore, derivatives of montbretin A, which are able to similarly bind may also provide similar inhibitory activity.

In accordance with another aspect there is provided a compound, wherein the compound has the structure of Formula I,

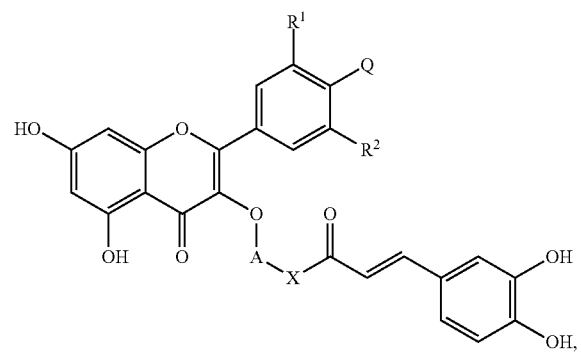

I wherein, Q may be H, OH or a monosaccharide; $R^1$ may be H or OH; $R^2$ may be H or OH; X may be O or NH; and A may be a disaccharide, a trisaccharide,

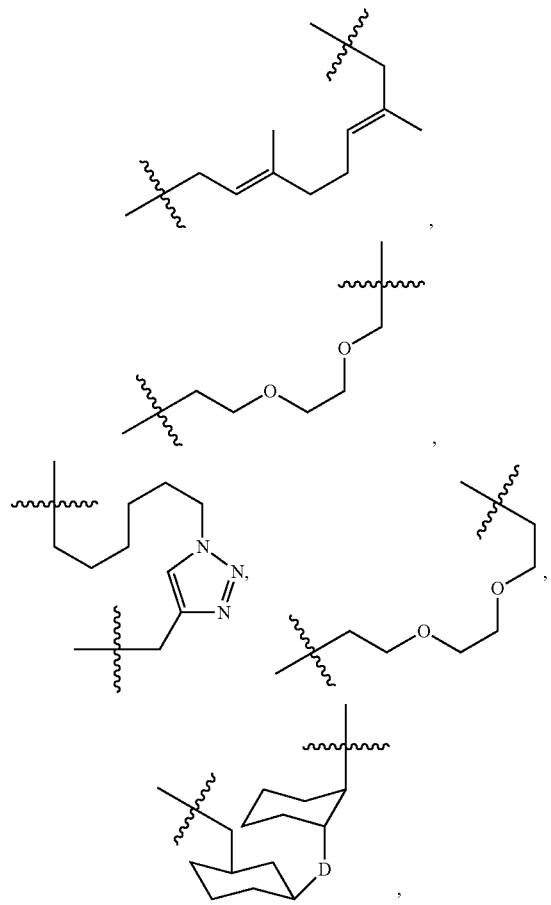

a polyethylene glycol comprised of $CH_2CH_2O$ subunits; a polyprenyl chain; or a 3-15 carbon alkyl; wherein D may be $CH_2$, O, S, or NH; and provided that when A may be a trisaccharide, Q may be H or a monosaccharide.

In accordance with another aspect there is provided a compound, wherein the compound has the structure of Formula I,

I

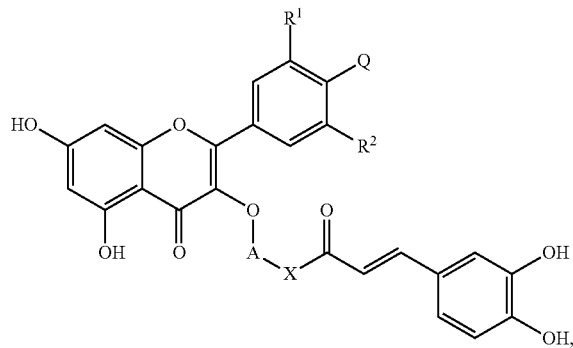

wherein, Q may be H, OH or a monosaccharide; $R^1$ may be H or OH; $R^2$ may be H or OH; X may be O or NH; and A may be a disaccharide, a trisaccharide, a polyethylene glycol comprised of $CH_2CH_2O$ subunits; or a 3-15 carbon alkyl; and wherein D may be $CH_2$, O, S, or NH. In accordance with another aspect there is provided a method inhibiting a mammalian α-amylase, including administering a compound of Formula I or a salt thereof to a subject in need thereof,

I

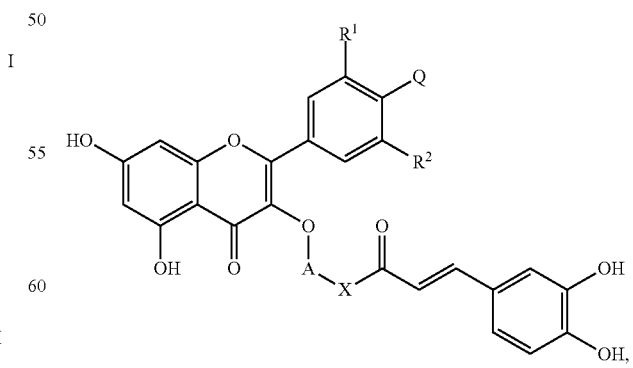

wherein, Q may be H, OH or a monosaccharide; $R^1$ may be H or OH; $R^2$ may be H or OH; X may be O or NH; and A may be a disaccharide, a trisaccharide,

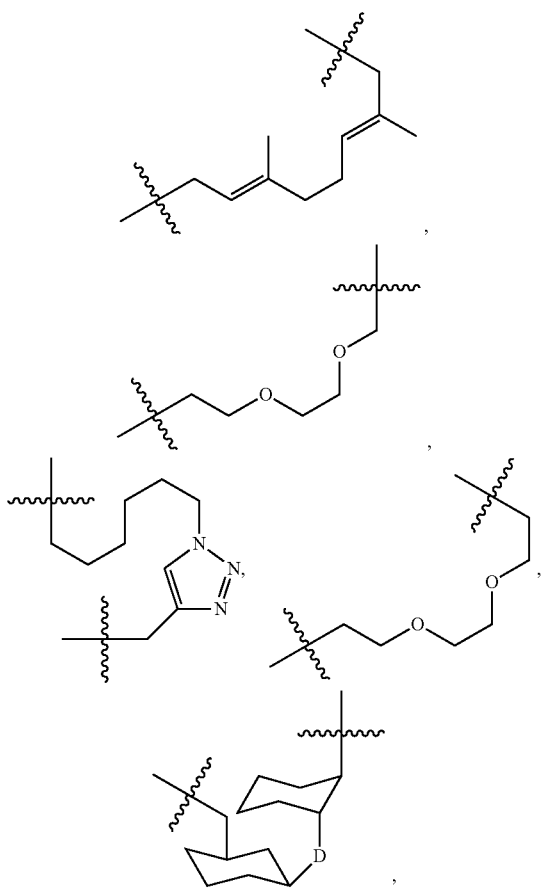

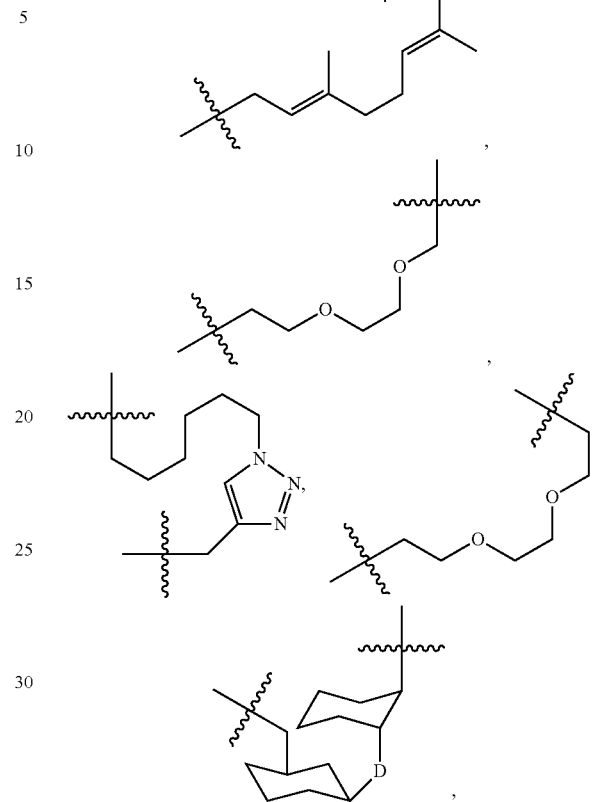

a polyethylene glycol comprised of CH₂CH₂O subunits; a polyprenyl chain; or a 5-15 carbon alkyl; and wherein D may be $CH_2$, O, S, or NH.

In accordance with another aspect there is provided a food composition, a beverage composition, a nutritional supplement composition, a pharmaceutical composition, an oral rinse composition, a tooth paste composition, or a chewing gum composition, including:

(a) a compound or salt of Formula I,

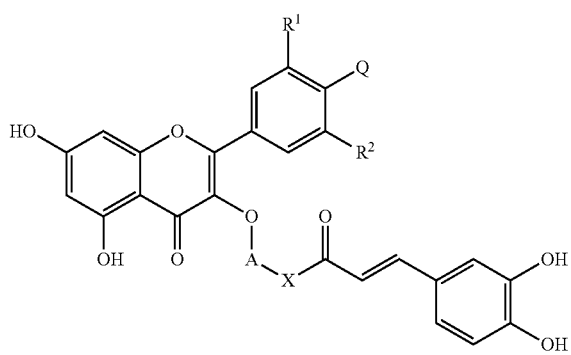

I wherein, Q may be H, OH or a monosaccharide; $R^1$ may be H or OH; $R^2$ may be H or OH; X may be O or NH; and A may be a disaccharide, a trisaccharide, a polyethylene glycol comprised of CH₂CH₂O subunits; a polyprenyl chain; or a 5-15 carbon alkyl; and wherein D may be $CH_2$, O, S, or NH; and (b) one or more physiologically acceptable carriers or excipients.

In accordance with another aspect there is provided a food composition which includes a compound described herein.

In accordance with another aspect there is provided a beverage composition which includes a compound described herein.

In accordance with another aspect there is provided a nutritional supplement composition which includes a compound described herein.

In accordance with another aspect there is provided a pharmaceutical composition which includes a compound described herein.

In accordance with another aspect there is provided an oral rinse composition which includes a compound described herein.

In accordance with another aspect there is provided a tooth paste composition which includes a compound described herein.

In accordance with another aspect there is provided a chewing gum composition which includes a compound described herein.

The disaccharide may be selected from the following: sucrose; lactose; maltose; lactulose; maltose; trehalose; cellobiose; kojibiose; nigerose; isomaltose; sphorose; laminaribiose; gentiobiose; turanose; maltulose; palatinose; gentiobiulose; mannobiose; melibiose; rutinose; rutinulose; and xylobiose.

The trisaccharide may be selected from the following: isomaltotriose; nigerotriose; maltotriose; melezitose; maltotriulose; raffinose; and kestos.
The trisaccharide may be
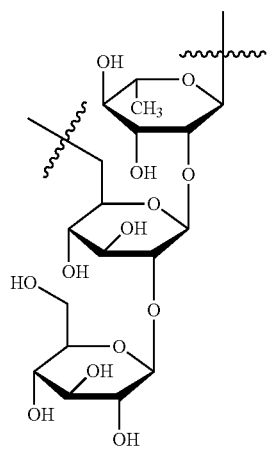
or
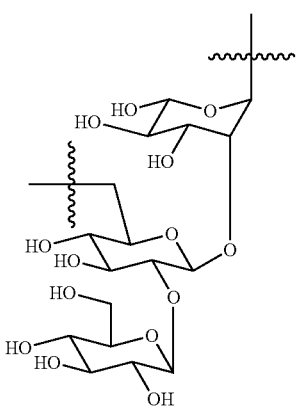
The disaccharide may be
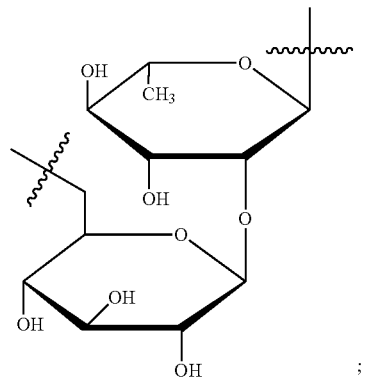
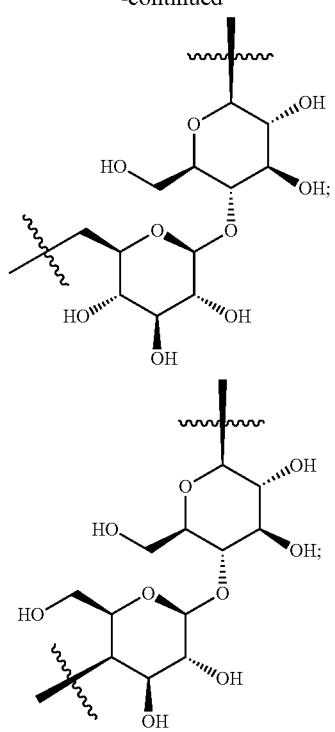
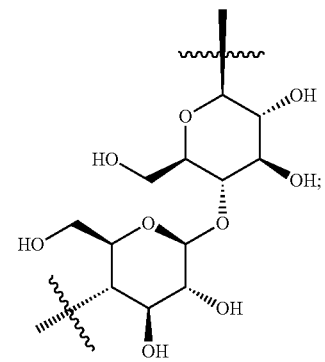
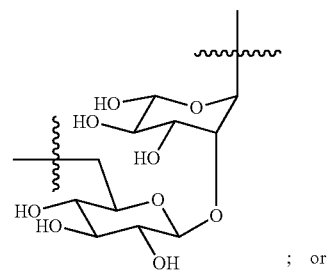
; or
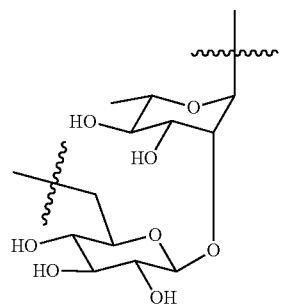

A may be selected from the following:
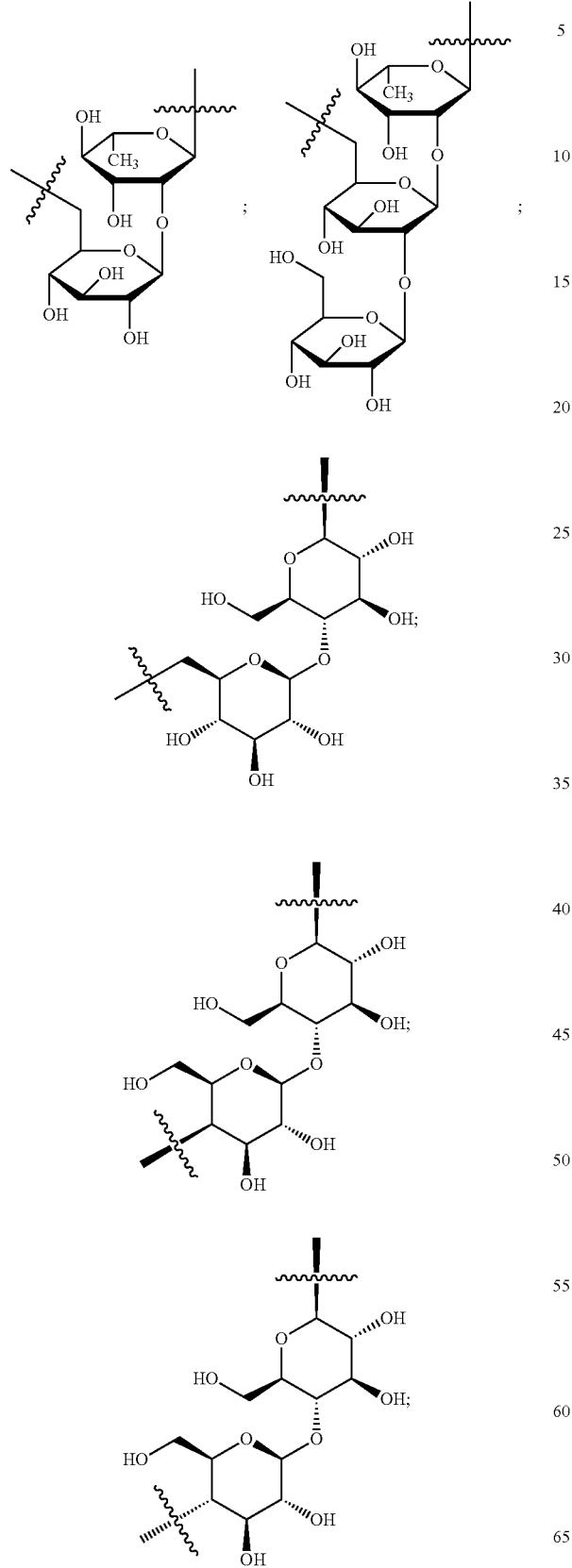
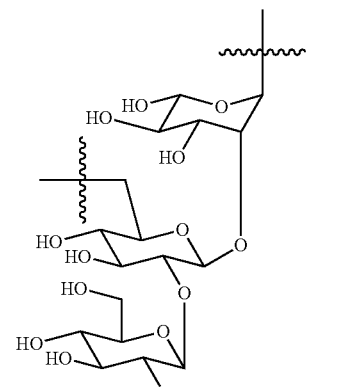
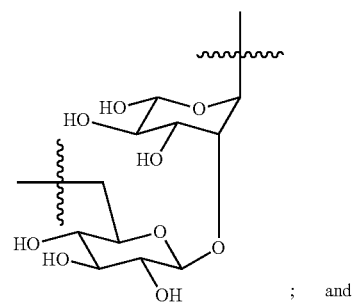
; and
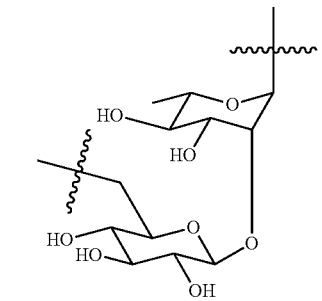
A may be selected from the following:
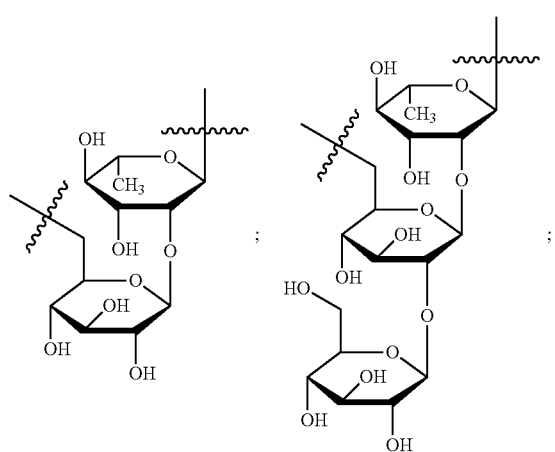

-continued
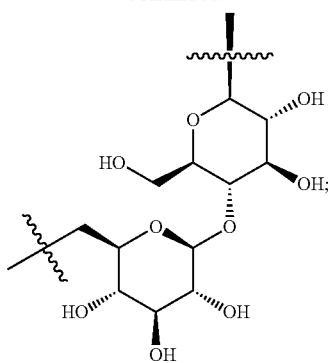
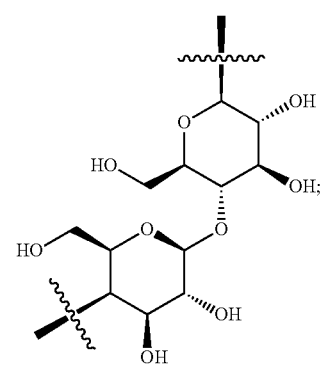
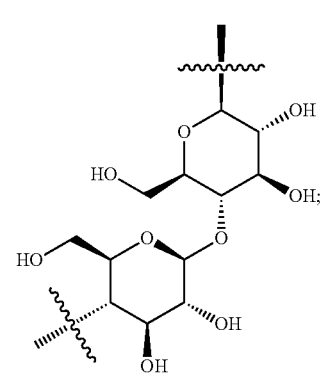
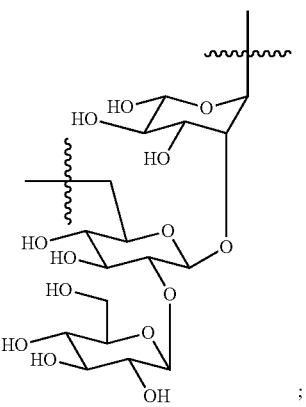
; and
-continued
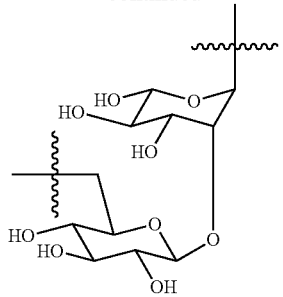
A may be selected from the following:
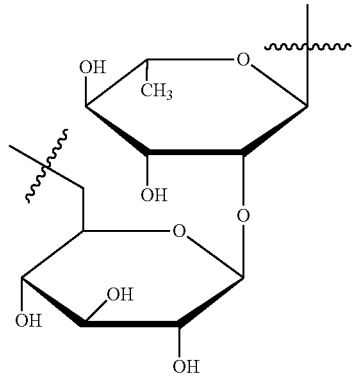
;
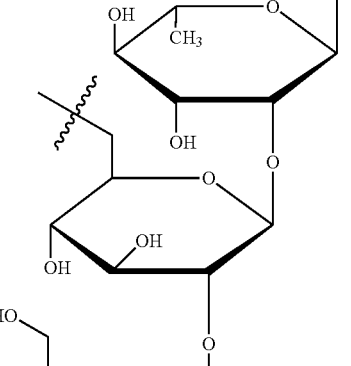
;
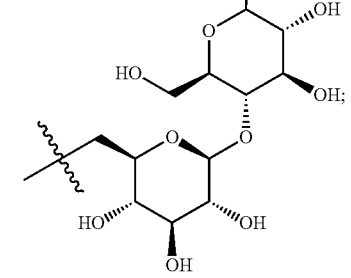

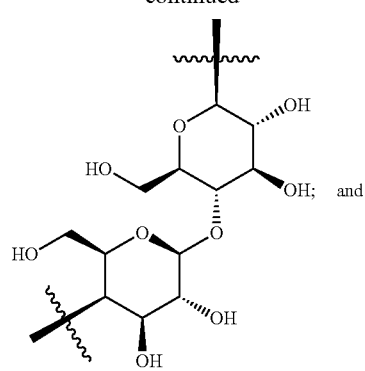
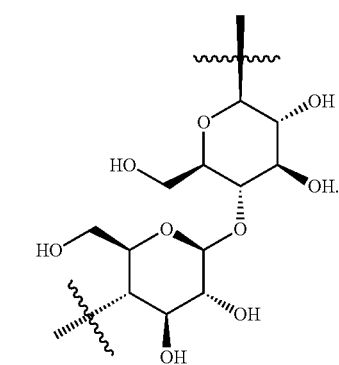
A may be selected from the following:
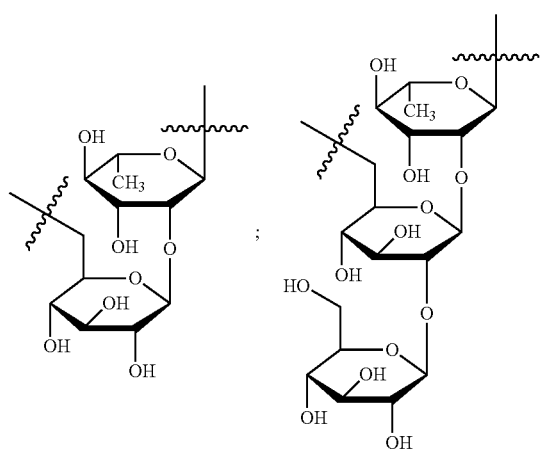
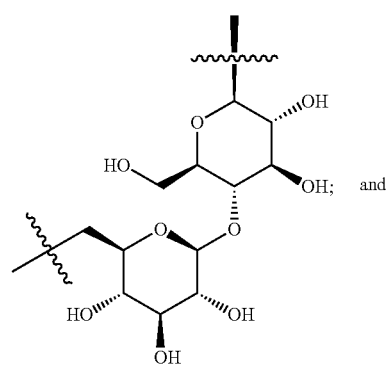
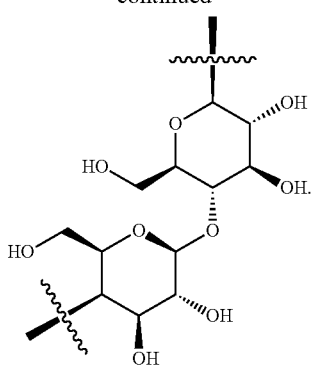
A may be selected from the following:
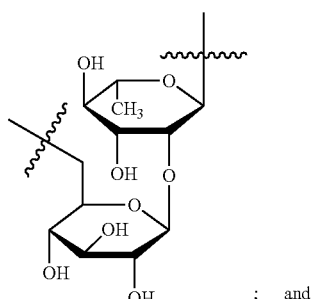
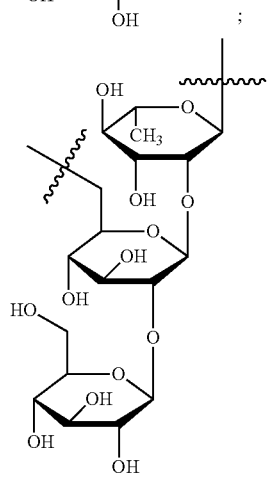
A may be
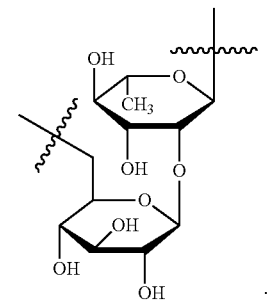

A may be

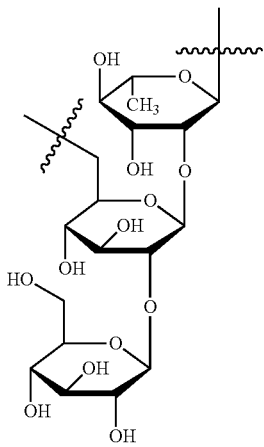

A may be

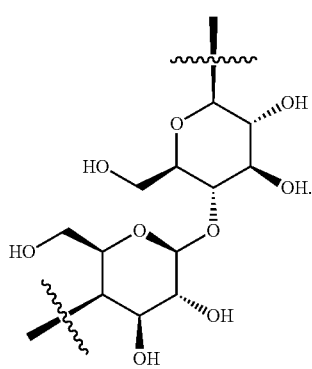

A may be

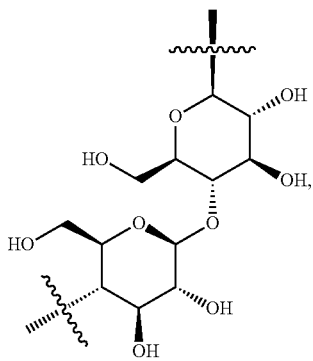

The polyprenyl chain may be 1-3

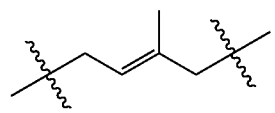 [SMILES: *C/C=C(\C)C*]

subunits. The polyprenyl chain may be 1-10

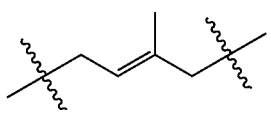 [SMILES: *C/C=C(\C)C*]

subunits. The polyprenyl chain may be 1-5

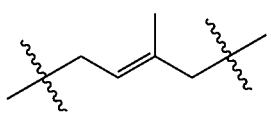 [SMILES: *C/C=C(\C)C*]

subunits.
The polyethelene glycol may be 1-5 CH$_2$CH$_2$O subunits. The polyethelene glycol may be 2-3 CH$_2$CH$_2$O subunits. The polyethelene glycol may be 2-4 CH$_2$CH$_2$O subunits. The polyethelene glycol may be 2-5 CH$_2$CH$_2$O subunits. The polyethelene glycol may be 1-4 CH$_2$CH$_2$O subunits. The polyethelene glycol may be 1-3 CH$_2$CH$_2$O subunits. The polyethelene glycol may be 1-1 CH$_2$CH$_2$O subunits. The polyethelene glycol may be 1 CH$_2$CH$_2$O subunit. The polyethelene glycol may be 2 CH$_2$CH$_2$O subunits. The polyethelene glycol may be 3 CH$_2$CH$_2$O subunits. The polyethelene glycol may be 4 CH$_2$CH$_2$O subunits. The polyethelene glycol may be 5 CH$_2$CH$_2$O subunits.

Q may be selected from glucose, fructose, arabinose, ribose, lyxose, rhamnose, xylose, allose, altrose, mannose, gulose, iodose, galactose and talose. Q may be selected from glucose, fructose, arabinose, ribose, lyxose, rhamnose, xylose, allose, mannose, gulose, iodose, galactose and talose. Q may be selected from glucose, fructose, arabinose, ribose, rhamnose, xylose, altrose, mannose, gulose, iodose, galactose and talose. Q may be selected from glucose, fructose, arabinose, ribose, lyxose, rhamnose, xylose, allose, altrose, mannose, iodose, galactose and talose. Q may be selected from glucose, fructose, arabinose, ribose, lyxose, rhamnose, xylose, allose, altrose, mannose, gulose, galactose and talose. Q may be selected from glucose, fructose, arabinose, ribose, lyxose, rhamnose, xylose, allose, altrose, mannose, gulose, iodose and galactose. Q may be selected from glucose, fructose, arabinose, ribose, rhamnose, xylose, mannose and galactose. Q may be a glucose. Q may be a xylose. Q may be a fructose. Q may be an arabinose. Q may be a ribose. Q may be a lyxose. Q may be a rhamnose. Q may be an allose. Q may be an altrose. Q may be a mannose. Q may be a gulose. Q may be an iodose. Q may be a galactose. Q may be a talose. The compound of claim 1, wherein Q may be H. The compound of claim 1, wherein Q may be OH.

A may be a 3-15 carbon alkyl, wherein the carbon alkyl has a structure selected from the following:

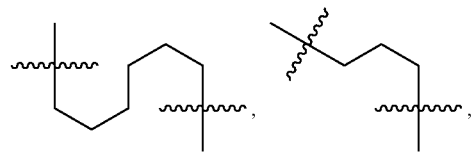

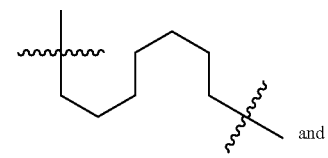 and

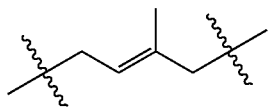 [SMILES: *C/C=C(\C)C*].

The 5-15 carbon alkyl may be a polyprenyl chain comprised of

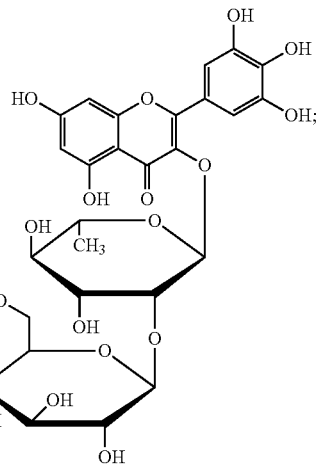

subunits. The polyethelene glycol may include 1-5 CH$_2$CH$_2$O subunits. The polyethelene glycol may include 2-3 CH$_2$CH$_2$O subunits. The Q may be a xylose. Q may be H. Q may be OH.

The compound may be selected from one or more of the following:

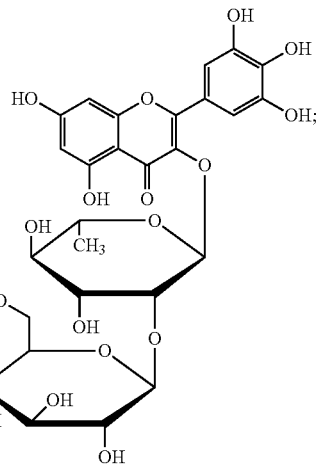

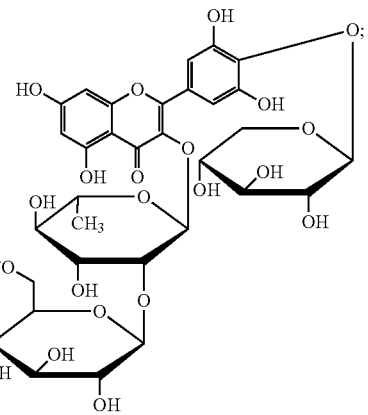

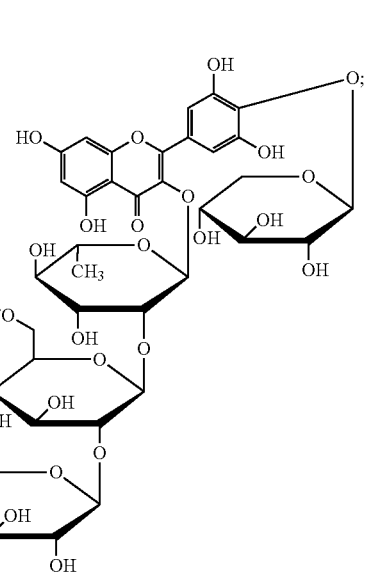

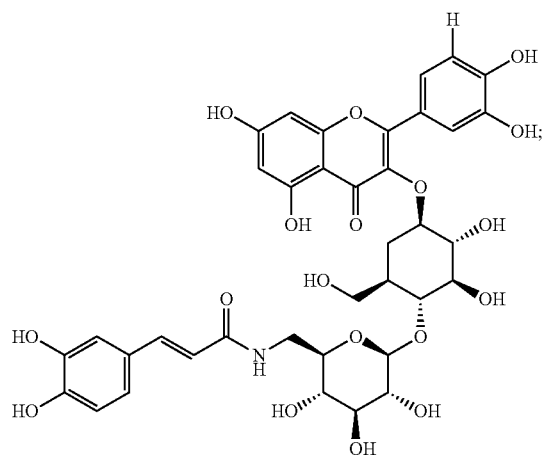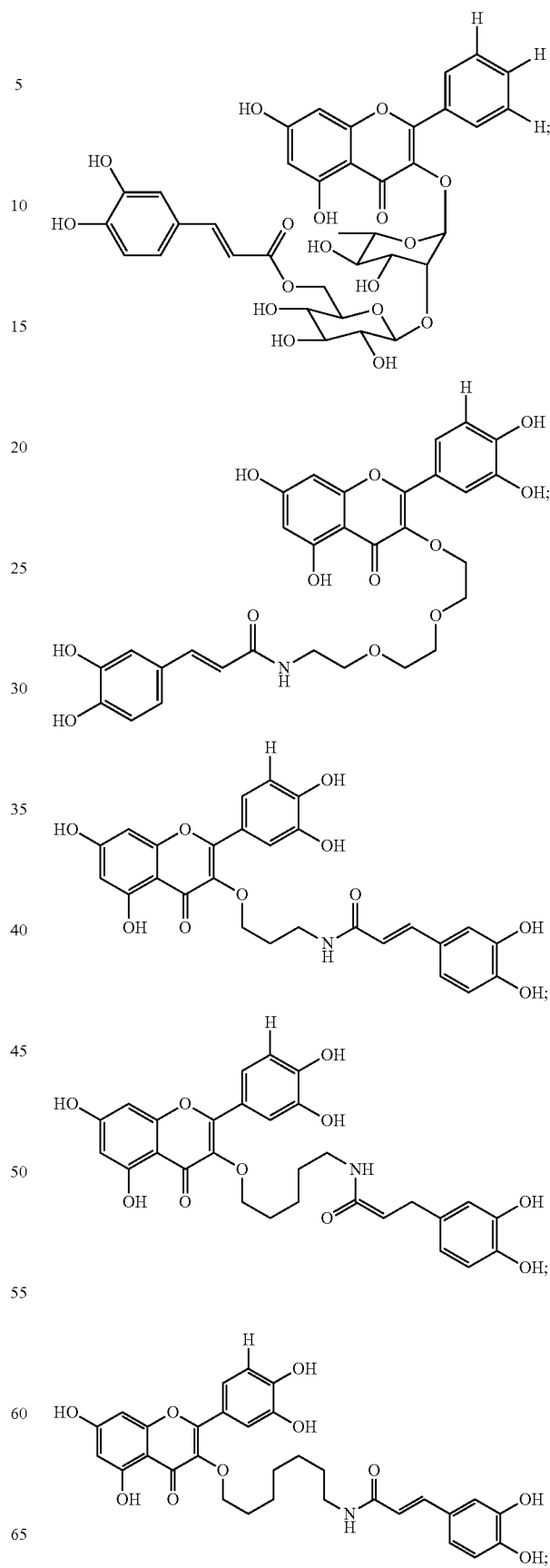

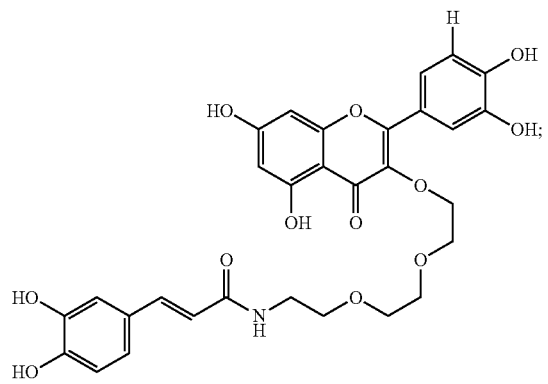
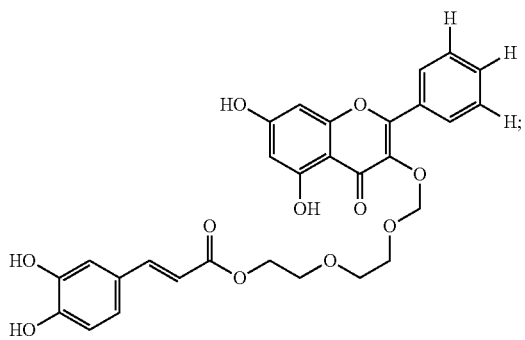
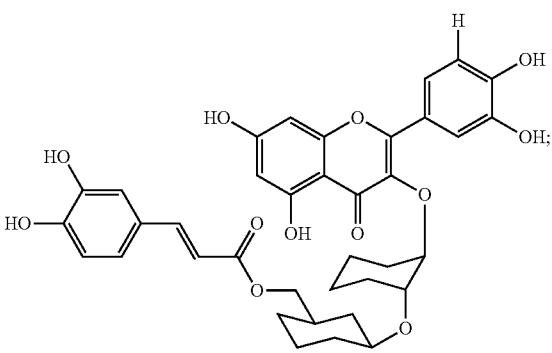
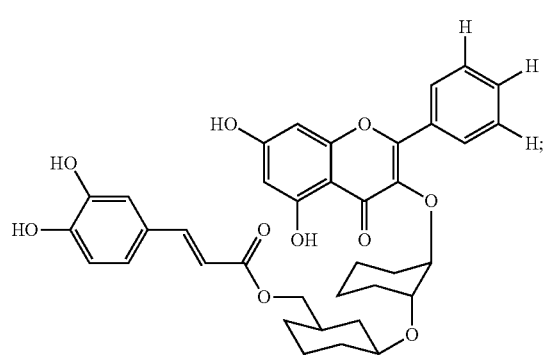
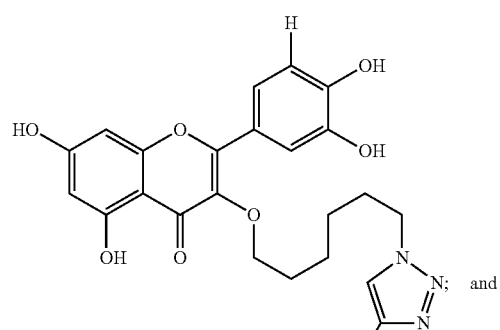

23
-continued
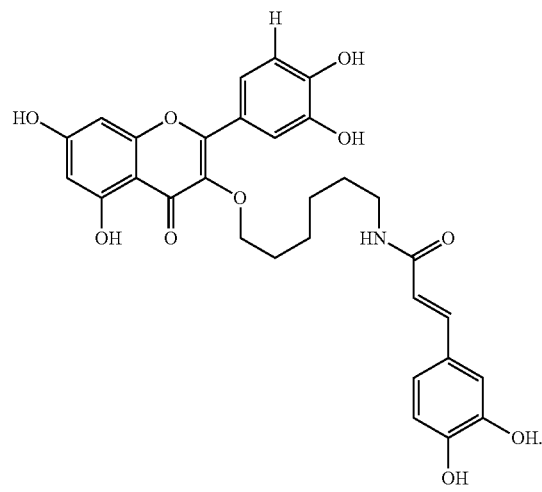
24
-continued
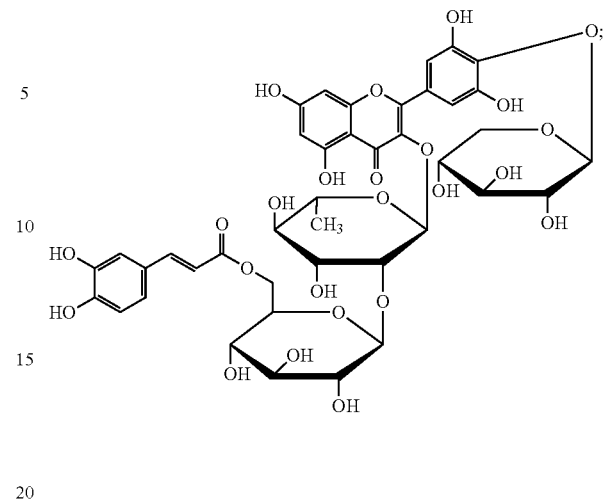
The compound may be selected from one or more of the following:
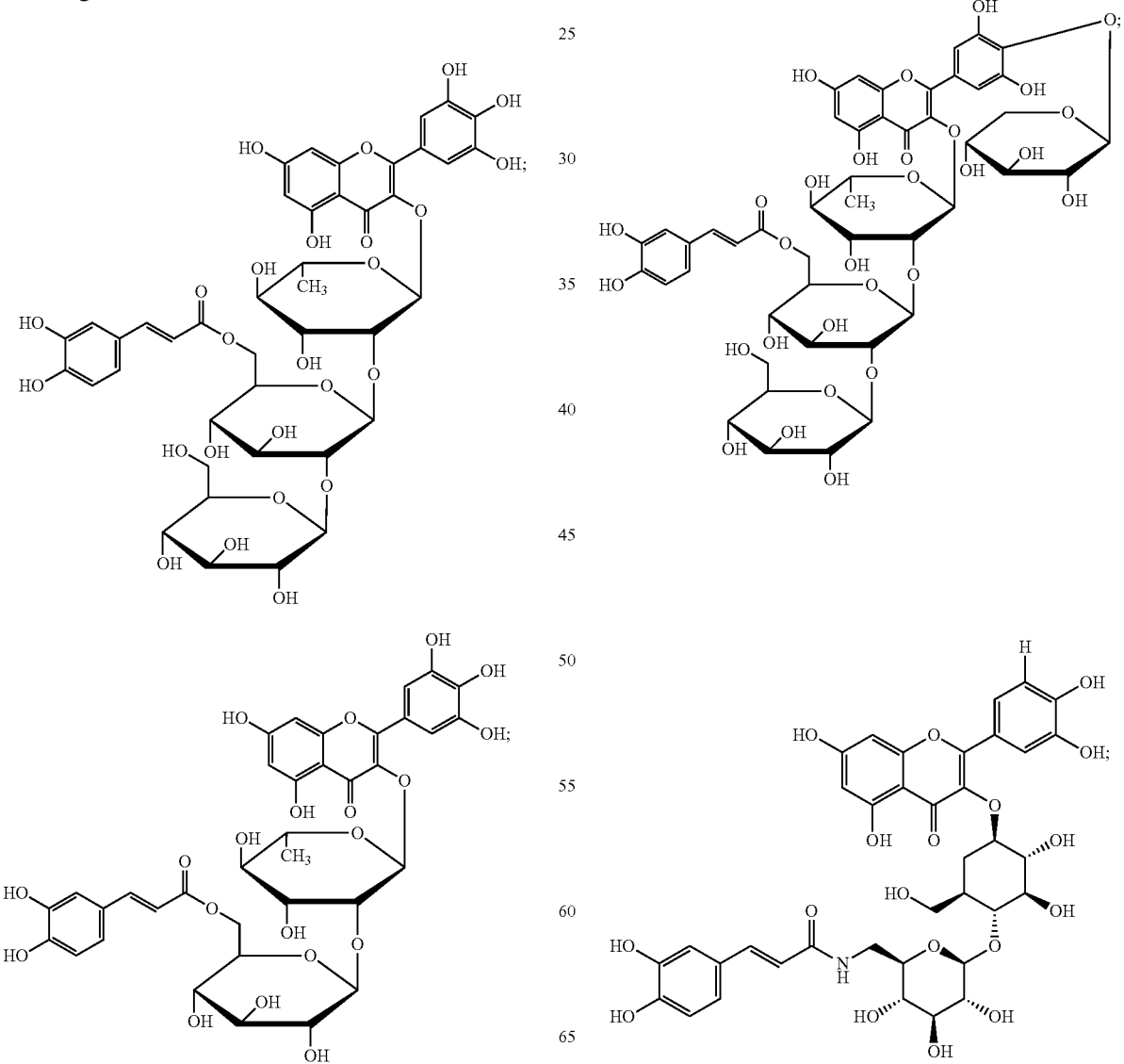

25
-continued
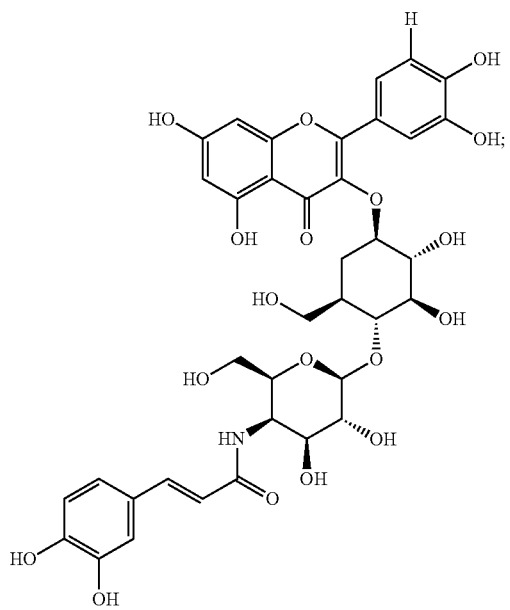
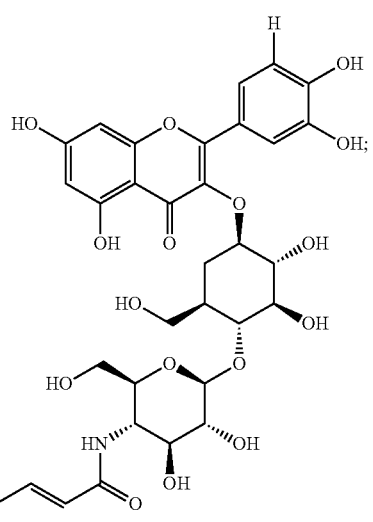
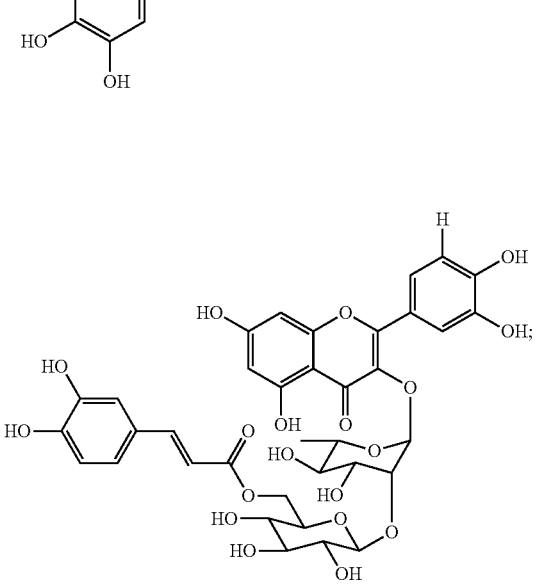
26
-continued
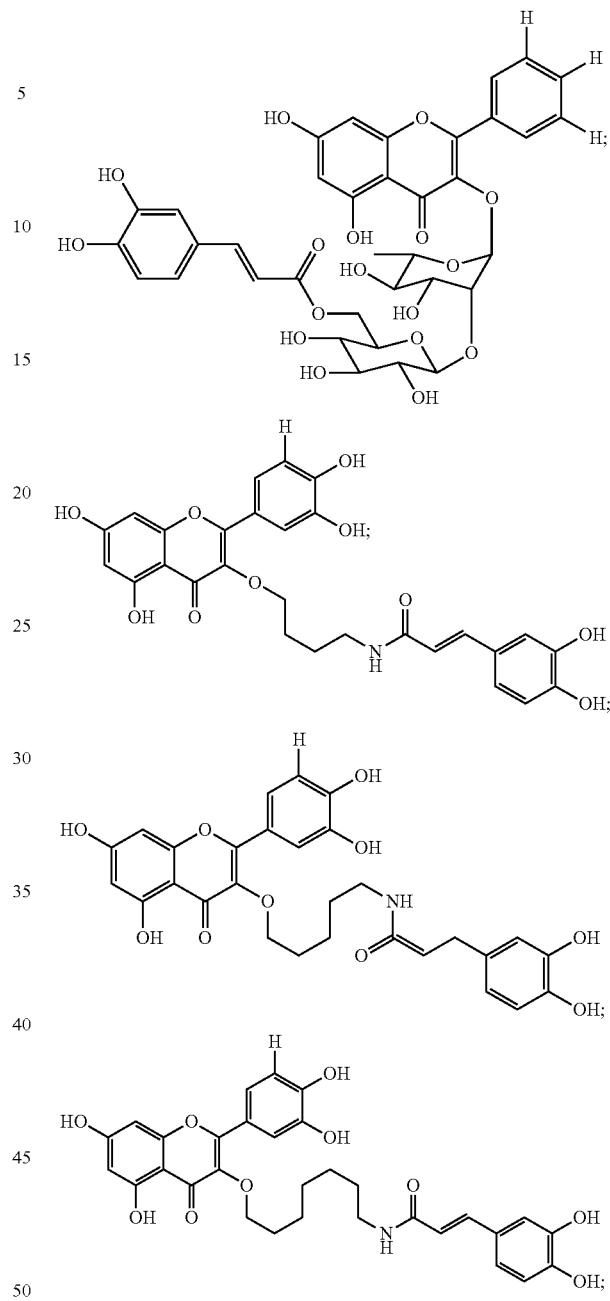
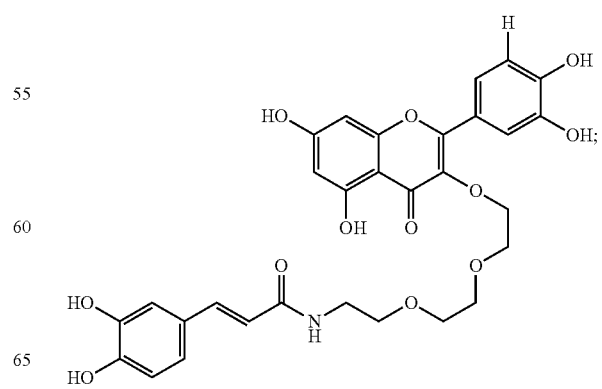

27
-continued
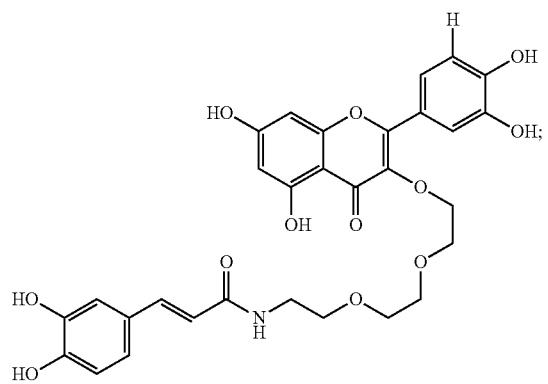
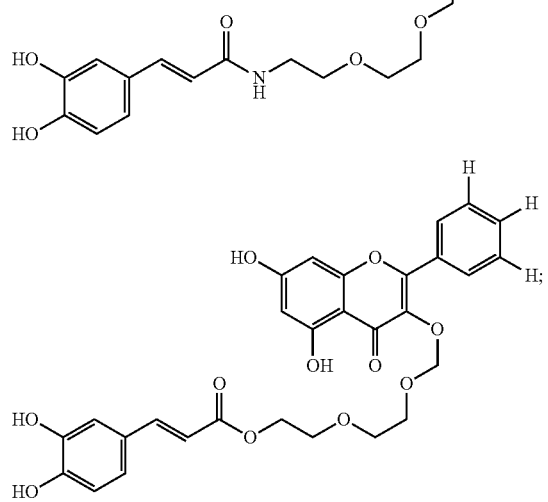
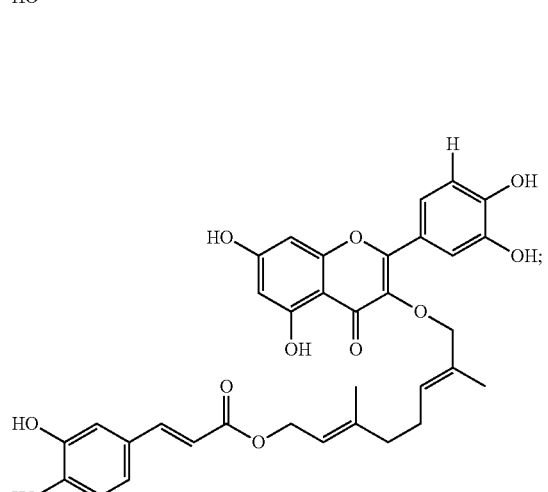
28
-continued
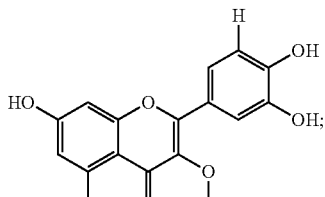
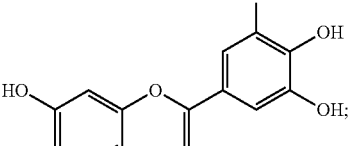
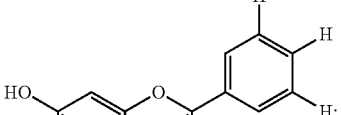
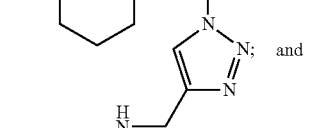 and 29
-continued
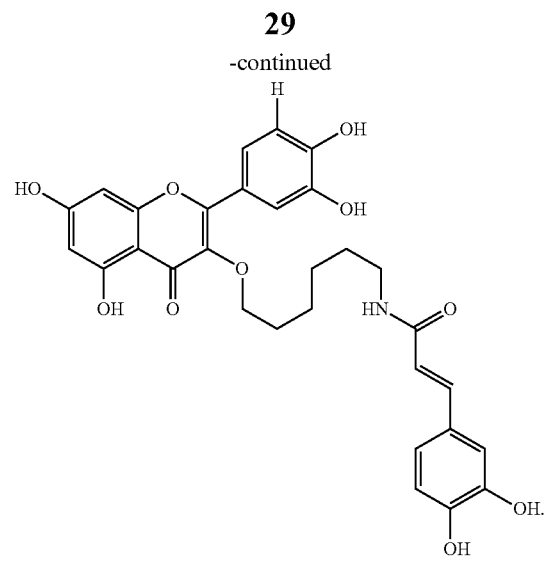
The compound may be selected from one or more of the following:
30
-continued
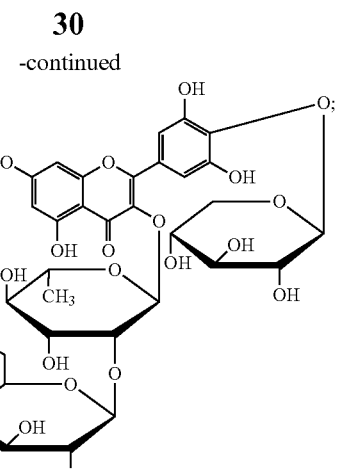
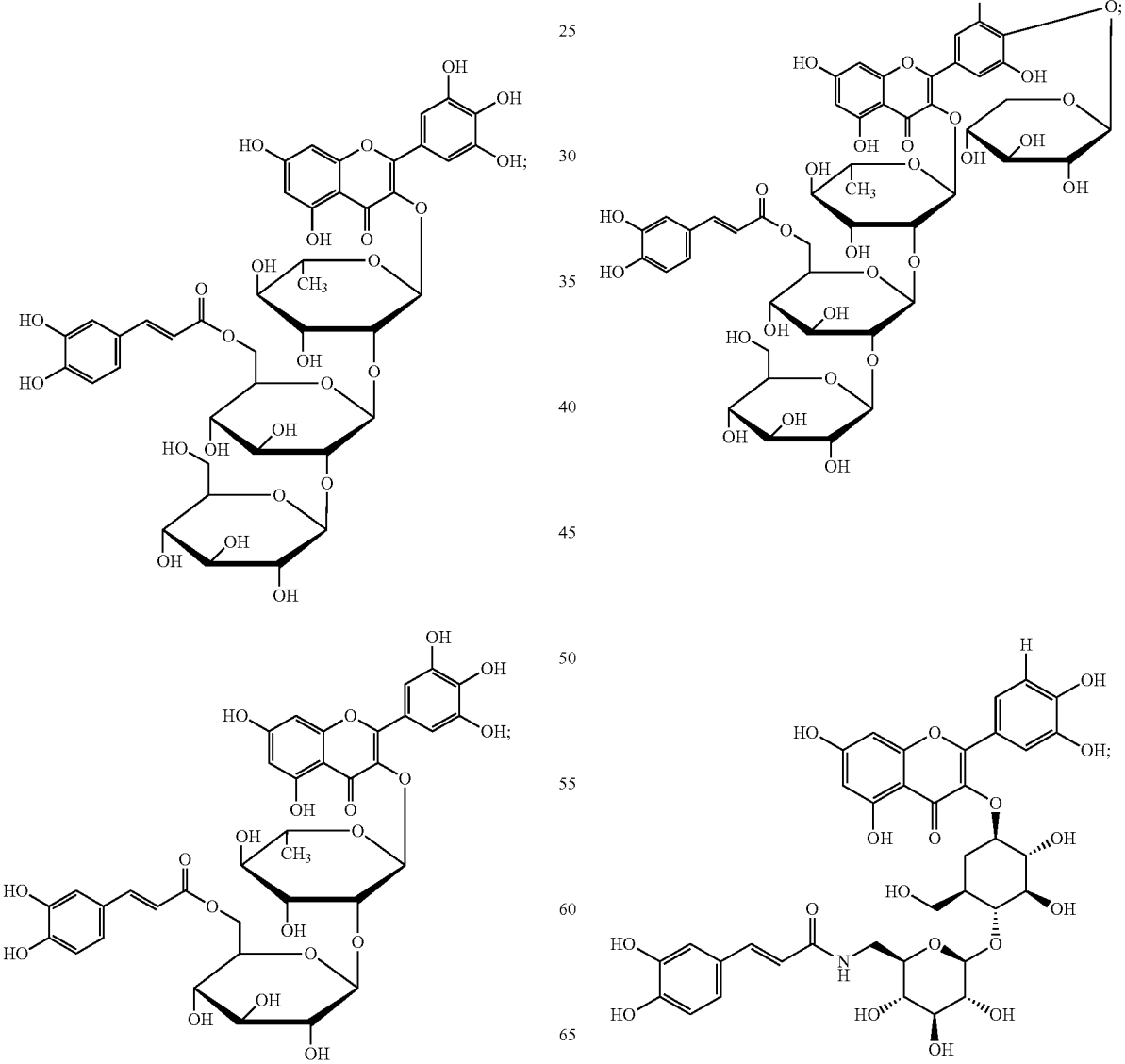

-continued
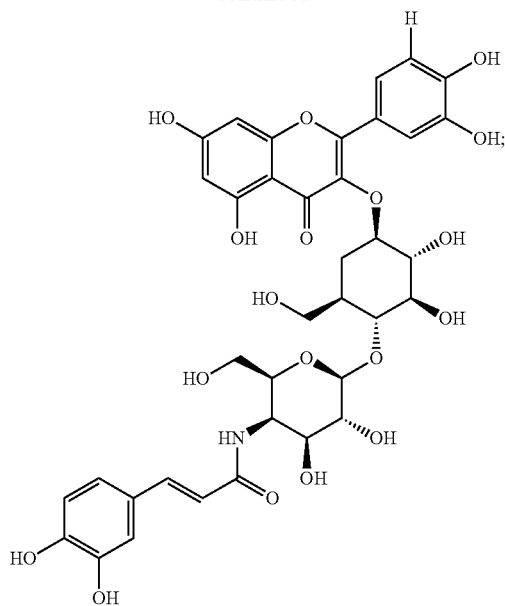
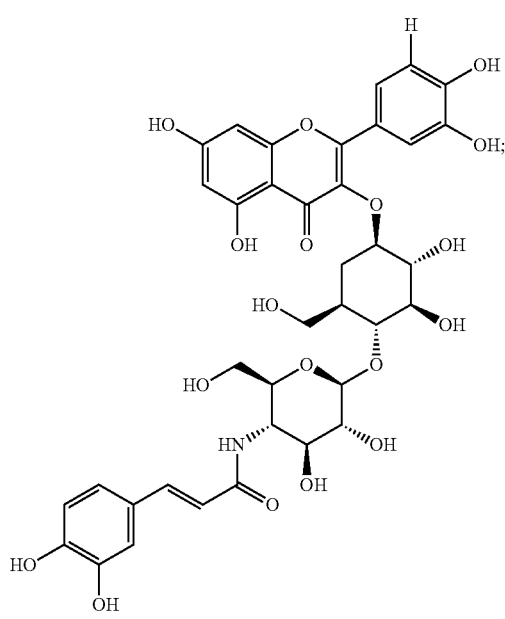
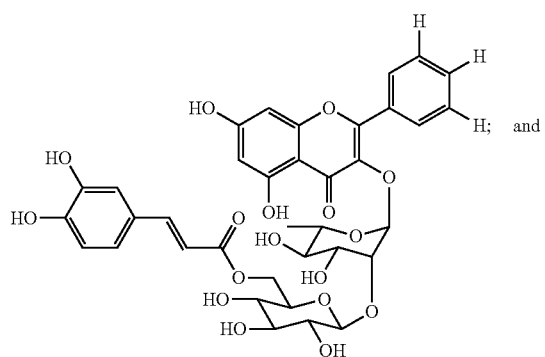
and
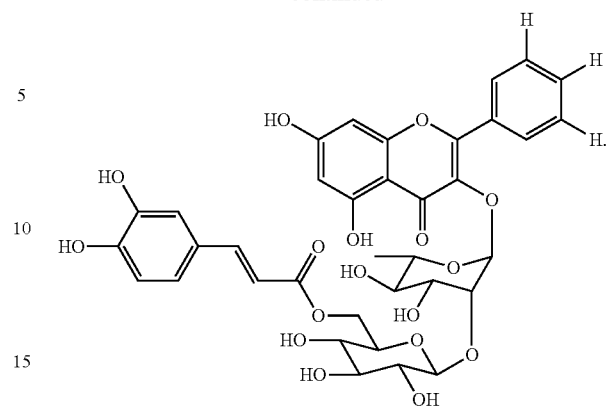
The compound may be selected from one or more of the following:
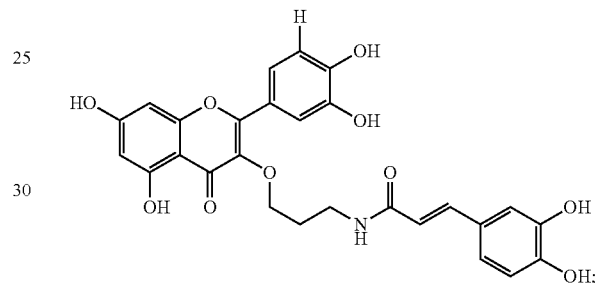
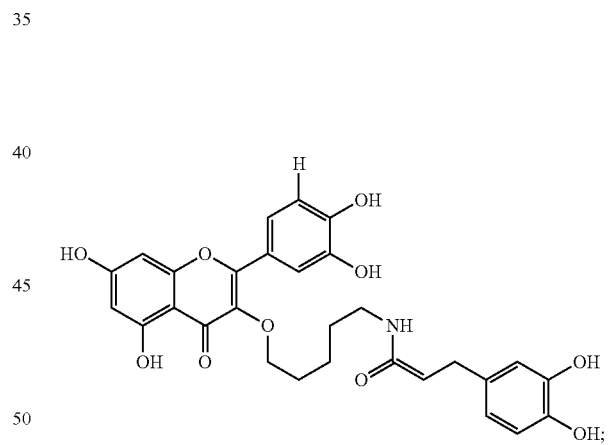
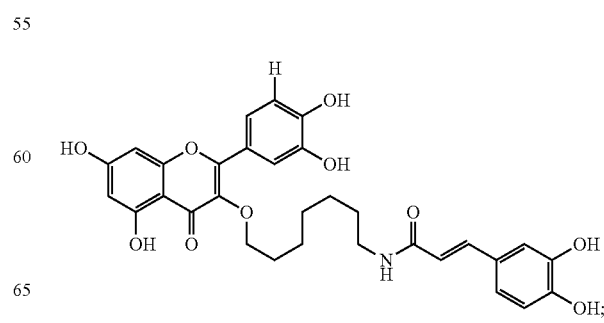

33
-continued
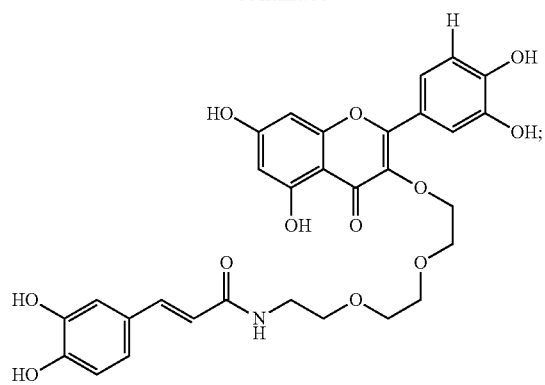
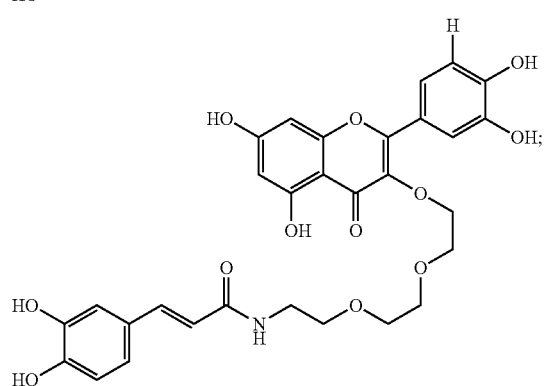
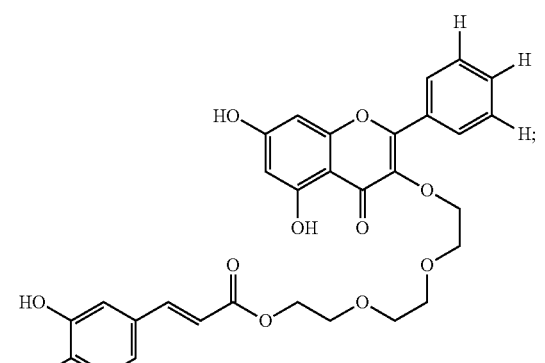
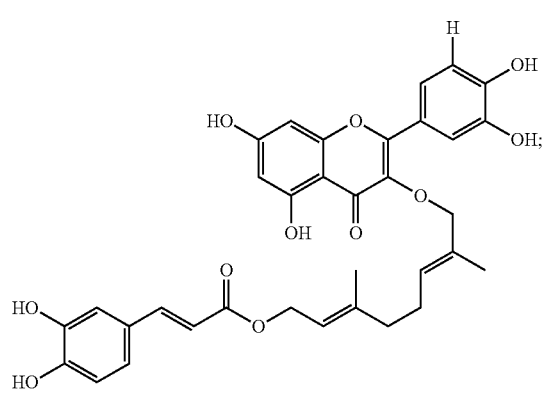
34
-continued
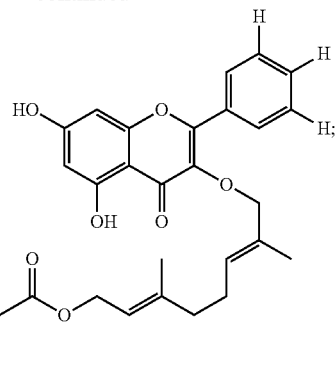
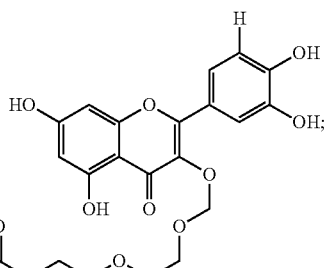
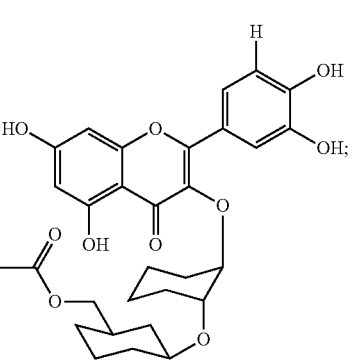
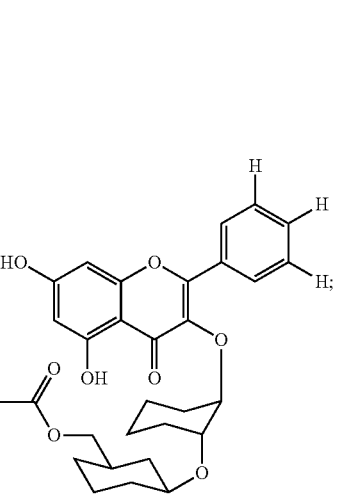

-continued

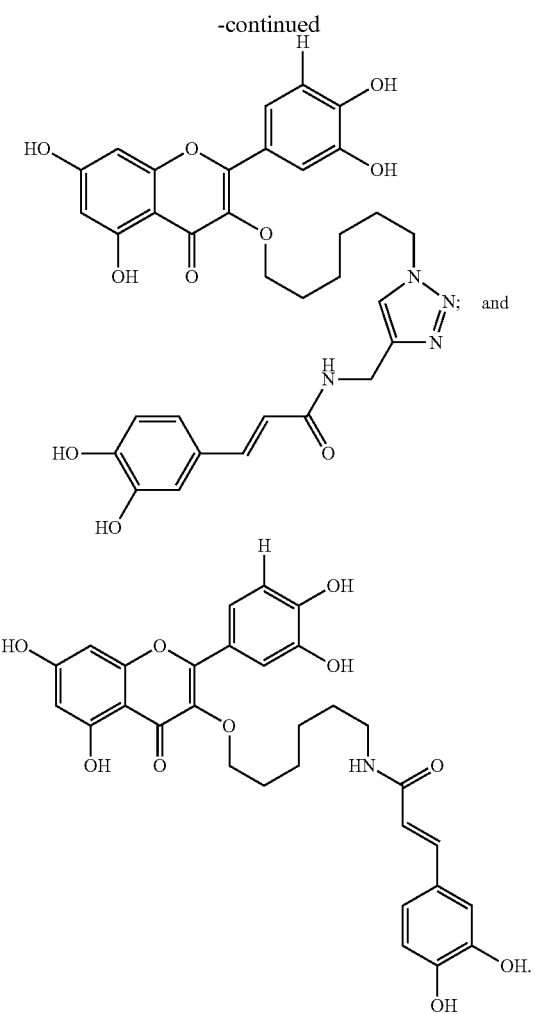

The mammalian α-amylase may be a salivary α-amylase or pancreatic α-amylase. The subject may be a human. The inhibition of the mammalian α-amylase may be for the treatment or prophylaxis of dental caries or plaque. The, inhibition of the mammalian α-amylase may be for the treatment or prophylaxis of pre-diabetes, diabetes or obesity. The administering of the compound of Formula I or a salt thereof to a subject in need thereof may be in an effective amount for the treatment or prophylaxis of pre-diabetes, diabetes or obesity or for the treatment or prophylaxis of dental caries or plaque.

Other aspects and features of the present invention will become apparent to those ordinarily skilled in the art upon review of the following description of specific embodiments of the invention in conjunction with the accompanying figures.

Abbreviations

HPA, human pancreatic α-amylase; MbA, montbretin A; Glc, D-glucose; CNPG3, 2-chloro-4-nitrophenyl α-maltotrioside; MPD, 2-methylpentane-2,4-diol. HPA amino acid numbering is according to the sequence alignment of reference (1).

BRIEF DESCRIPTION OF THE DRAWINGS

FIG. 4A shows plots from a ROESY NMR experiment used to model the conformation of the free form of MbA in solution, whereby the data in FIG. 4B indicates that the myricetin and ethyl caffeate ring moieties participate in π-stacking in solution, with identifiable strong interactions between groups have been drawn with dashed lines, while FIG. 4C shows a the bound conformation of MbA in the active site of HPA, whereby a strong correlation with the solution conformation, but with the major difference being a 180° flip of the plane of the caffeate ring (top of structures in FIGS. 4B and 4C).

FIG. 5B shows a schematic drawing of this hydrogen bonding network with distances shown in Ångstroms and protein residues with more than one hydrogen bond to MbA have been shaded the same when either two different atoms form hydrogen bonds or the same atom hydrogen bonds to disparate parts of the inhibitor, with water molecules shown with small grey spheres.

FIGS. 8A-8B show composite drawings of bound MbA and the catalytic residues D197, E233 and D300, overlaid with the structures of (FIG. 8A) wild-type HPA (1), and (FIG. 8B) the HPA/myricetin complex (Brayer, unpublished data)), and also drawn as dashed lines are hydrogen bonds between the catalytic residues and bound inhibitors, while notably the side chains of D197 and E233 are comparably positioned in all structures, in both of the complexes of MbA and myricetin, D300 is displaced away from that observed for uncomplexed HPA.

DETAILED DESCRIPTION

Definitions

Figure 1:
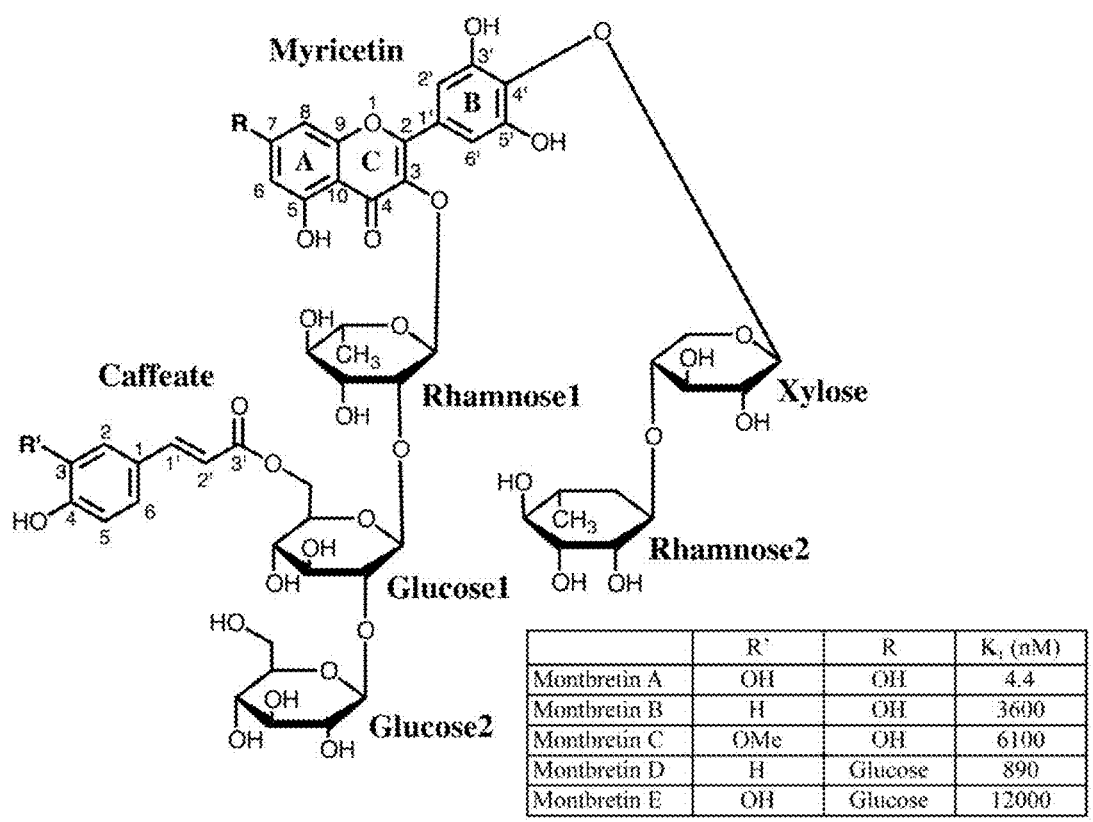
FIG. 1 shows the chemical structure of MbA and the related isoforms, montbretins B-E, as isolated from *crocosmia* sp. (5, 13). The identities of sugar rings present are labeled, and ring designations and atom numbering are indicated for the myricetin and caffeate moieties. The substituent identities specific to montbretins A-E and $K_I$ values measured for the inhibition of HPA by montbretins A-E are indicated in the inset table (5, 35, 36).

The term "monosaccharide" as used herein is meant to encompass any sugar having the general formula $C_x(H_2O)_y$, wherein x≥3 (i.e. triose (3) tetrose (4), pentose (5), hexose (6), heptose (7)). Alternatively, a monosaccharide may be considered any sugar that cannot be hydrolyzed to give a simpler sugar. For example, glucose, fructose, arabinose, ribose, lyxose, rhamnose, xylose, allose, altrose, mannose, gulose, iodose, galactose or talose. Furthermore, the monosaccharide may alternatively be in either the D or L configuration.

The term "disaccharide" as used herein is meant to encompass any sugar formed when two monosaccharides are joined by glycosidic linkage. Disaccharides may be any combination of monosaccharides as described herein (for example sucrose, lactose, maltose, lactulose, maltose, trehalose (for example β,β or α, β), cellobiose, kojibiose, nigerose, isomaltose, sphorose, laminaribiose, gentiobiose, turanose, maltulose, palatinose, gentiobiulose, mannobiose, melibiose, rutinose, rutinulose, xylobiose or any of the examples described herein, and wherein two monosaccharides may be joined by any number of possible linkages).

The term "trisaccharide" as used herein is meant to encompass any sugar formed when three monosaccharides are joined by glycosidic linkages. Disaccharides may be any combination of monosaccharides as described herein (for example, isomaltotriose, nigerotriose, maltotriose, melezitose, maltotriulose, raffinose, kestose or any of the examples described herein, and wherein three monosaccharides may be joined by any number of possible linkages). Furthermore, where the trisaccharide forms the linker X, the bond joining the linker X to A may from the middle sugar moiety.

The term "polyprenyl chain" as used herein is meant to encompass any number of repeating

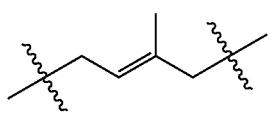 [SMILES: *C/C=C(\C)C*]

subunits, for example

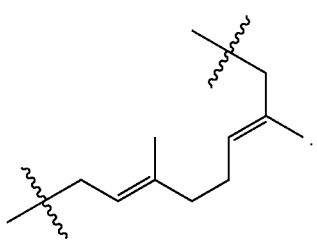 [SMILES: *C/C=C(\C)CC/C=C(\C)C*]

The polyprenyl chain may be 3-10 repeating

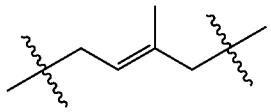 [SMILES: *C/C=C(\C)C*]

subunits. The polyprenyl chain may be 3-5 repeating

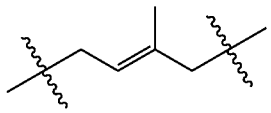 [SMILES: *C/C=C(\C)C*]

subunits.

The term "polyethylene glycol" (PEG) is also known as polyethylene oxide (PEO) or polyoxyethylene (POE), and is a polyether compound. As used herein, PEG is meant to encompass any number of $CH_2CH_2O$ subunits, for example

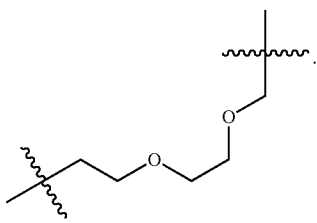 [SMILES: *CCOCCOC*]

PEG has the structure H—(O—CH2—CH2)n-OH. The PEG chain may be 3-10 repeating subunits. The PEG chain may be 3-5 repeating subunits.

The term "carbon alkyl" as used herein is meant to encompass a carbon chain that is either linear or branched or cyclic or a combination thereof, where the carbon chain comprises carbon atoms and associated hydrogens.

The term "α-amylase" as used herein is meant to encompass an enzyme that hydrolyses alpha bonds of large, alpha-linked polysaccharides, such as starch and glycogen, yielding glucose and maltose. There are two main human α-amylases, a salivary α-amylase and pancreatic α-amylase Alpha-amylase is the major form of amylase found in humans and other mammals.

In earlier work we have studied the three-dimensional structures of the complexes of both myricetin and ethyl caffeate with HPA using protein crystallographic techniques (Brayer, unpublished data). These results show that these two inhibitors have very different modes of action, with myricetin binding directly in the active site adjacent to catalytic residues, whereas, unexpectedly, ethyl caffeate binds in multiple surface pockets outside the active site region and yet demonstrates the unique ability to disorder the elongated substrate binding cleft. From a subsequent comparison of these structural results with the chemical structure of MbA, it is clear that MbA must bind in a different manner from that observed for these two related smaller inhibitors.

Figure 2:
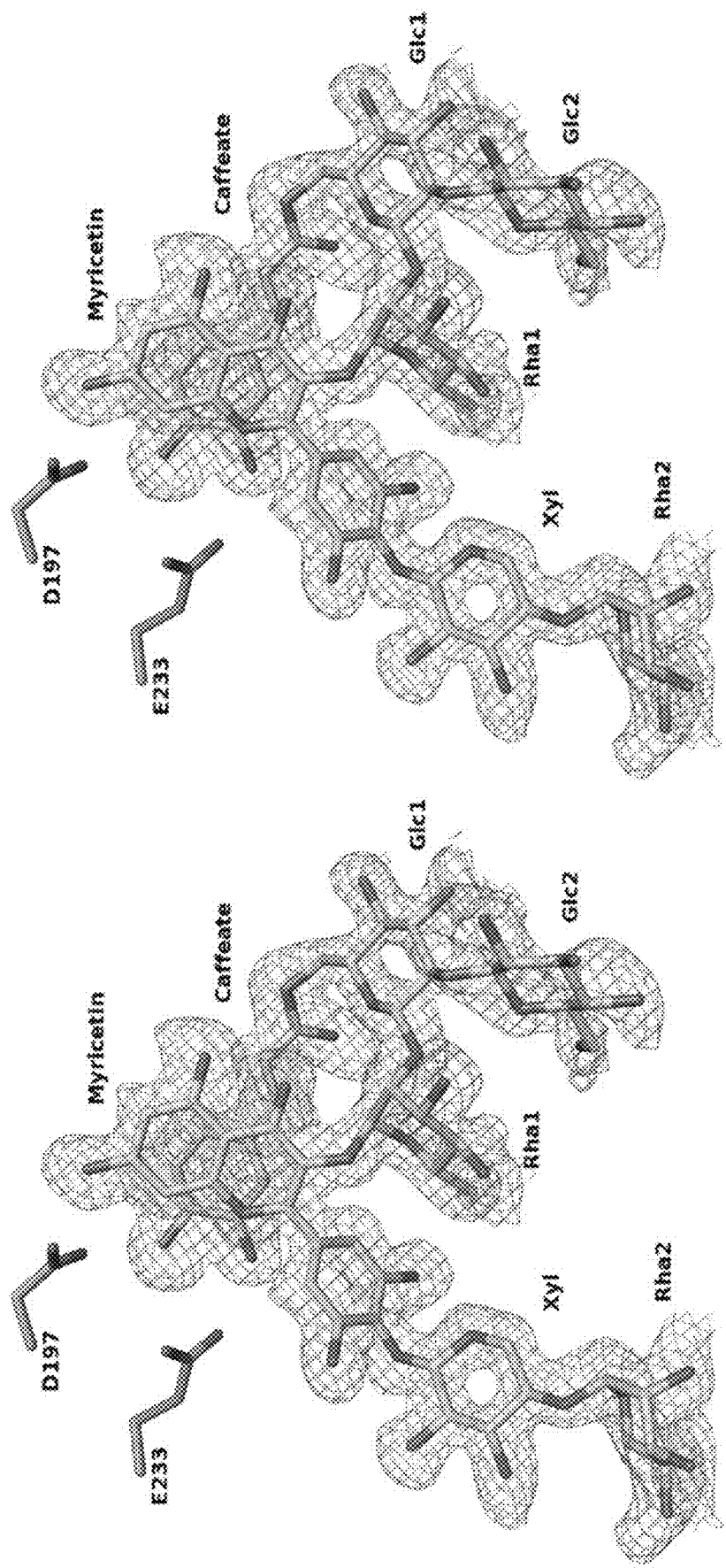
FIG. 2 shows a stereo representation of the bound conformation of montbretin A (MbA) situated in the active site of H299N human pancreatic α-amylase (HPA), wherein the accompanying omit map is contoured at the 2σ level, and the catalytic nucleophile, D197, and the acid-base catalyst, E233, of HPA are shown for reference.

MbA is a large and chemically complex inhibitor ($C_{53}H_{64}O_{33}$; MW=1228.3 daltons) with a variety of different functional groups (see FIG. 1). As TABLE 1 indicates, high quality 1.75 Å resolution X-ray diffraction data was obtained from the co-crystallized complex of this inhibitor bound in the active site of HPA. Exceptionally well-defined electron density in subsequent electron density maps clearly indicated the nature of the non-covalently bound conformation of MbA adjacent to the HPA active site residues D197, E233 and D300 (FIG. 2). As is evident from FIG. 3, bound MbA fills in the majority of the volume of the extended active site binding cleft of HPA and thereby completely occludes catalytic residues from access to bulk solvent. MbA remains unmodified by HPA, an enzyme known for carrying out promiscuous hydrolysis and trans-glycosylyation reactions with other inhibitors whose structures more closely mimic those of substrates (29-32).

TABLE 1

Summary of Structure Determination Statistics

| Complex Structure | Montbretin A/<br>HPA Inhibitor Complex |
|---|---|
| Data Collection Parameters | |
| Space group | $P2_12_12_1$ |
| Unit cell dimensions (Å) | |
| a | 52.69 |
| b | 74.74 |
| c | 135.48 |
| No. of unique reflections | 52965 |
| Mean I/σI [a] | 18.8 (10.2) |
| Multiplicity [a] | 5.0 (5.2) |
| Merging R-factor (%) [a] | 5.6 (10.5) |
| Maximum resolution (Å) | 1.75 |
| Structure Refinement Values | |
| Number of reflections | 52813 |
| Resolution range (Å) | 37.4-1.75 |
| Completeness (%) [a] | 96.9 (99.5) |
| No. protein atoms | 3943 |
| No. inhibitor atoms | 86 |
| No. solvent atoms | 566 |
| Average thermal factors (Å$^2$) | |
| Protein atoms | 13.6 |
| Inhibitor atoms | 22.7 |
| Solvent atoms | 35.5 |
| Overall | 25.6 |
| Final R-free value (%) [b] | 21.6 |
| Final R-factor (%) | 18.6 |
| Structure Stereochemistry | r.m.s. deviations |
| bonds (Å) | 0.014 |
| angles (°) | 1.76 |

[a] Values in parentheses refer to the highest resolution shell: 1.84-1.75 Å.
[b] 5% of the data was set aside to calculate R-free.

Surprisingly, one of the most important interactions that would appear to facilitate inhibitor/HPA complexation is in fact internal to the MbA inhibitor structure itself. This is the purely hydrophobic π-stacking interaction observed between the planar A-ring of the myricetin group and the ring of the caffeate group (FIG. 2). It is this substructure complex that appropriately positions the hydroxyl groups at the edges of these planar groups next to catalytic groups with the subsequent formation of strong hydrogen bonds.

Figure 4A:
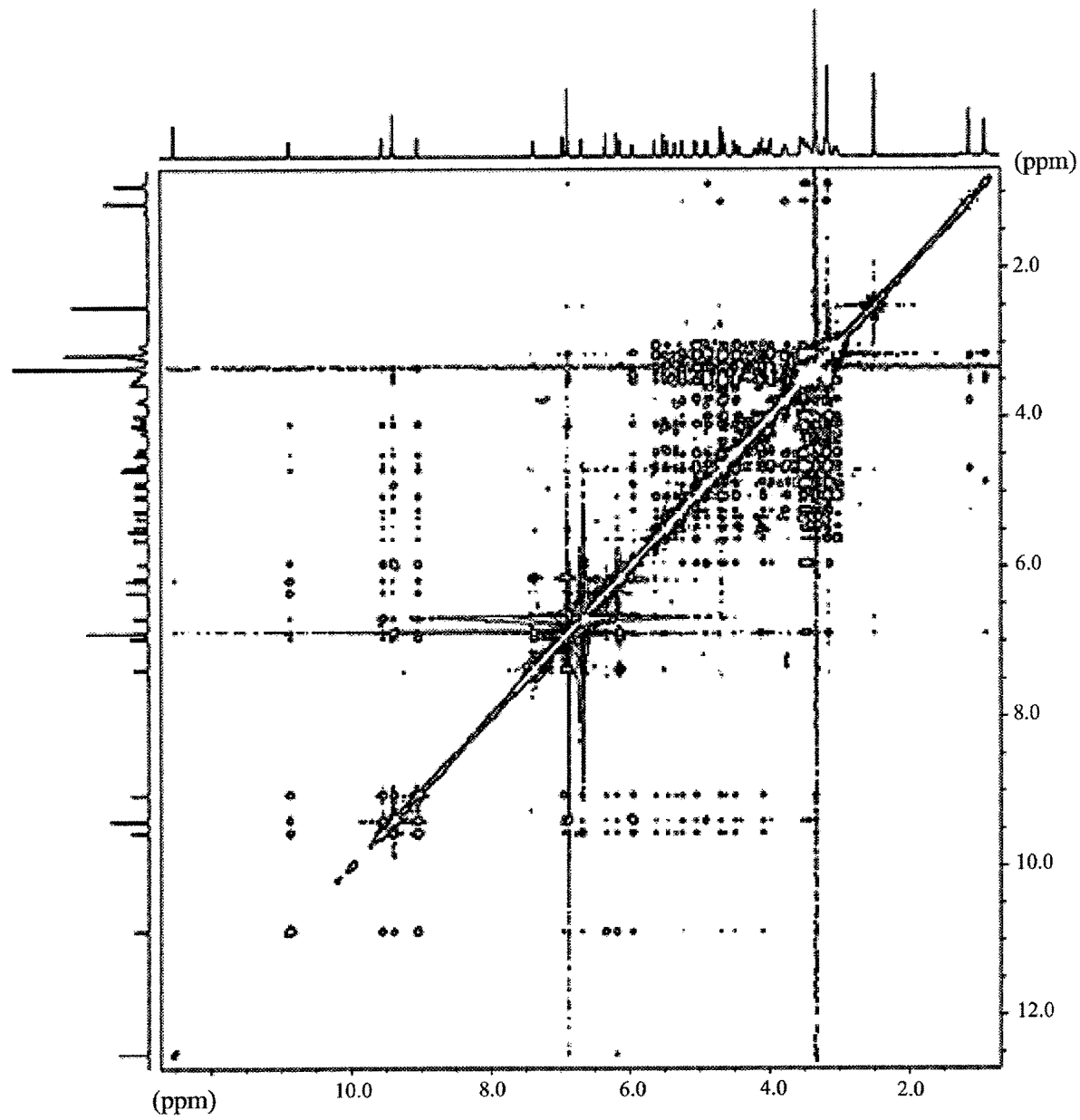
Figure 4A:
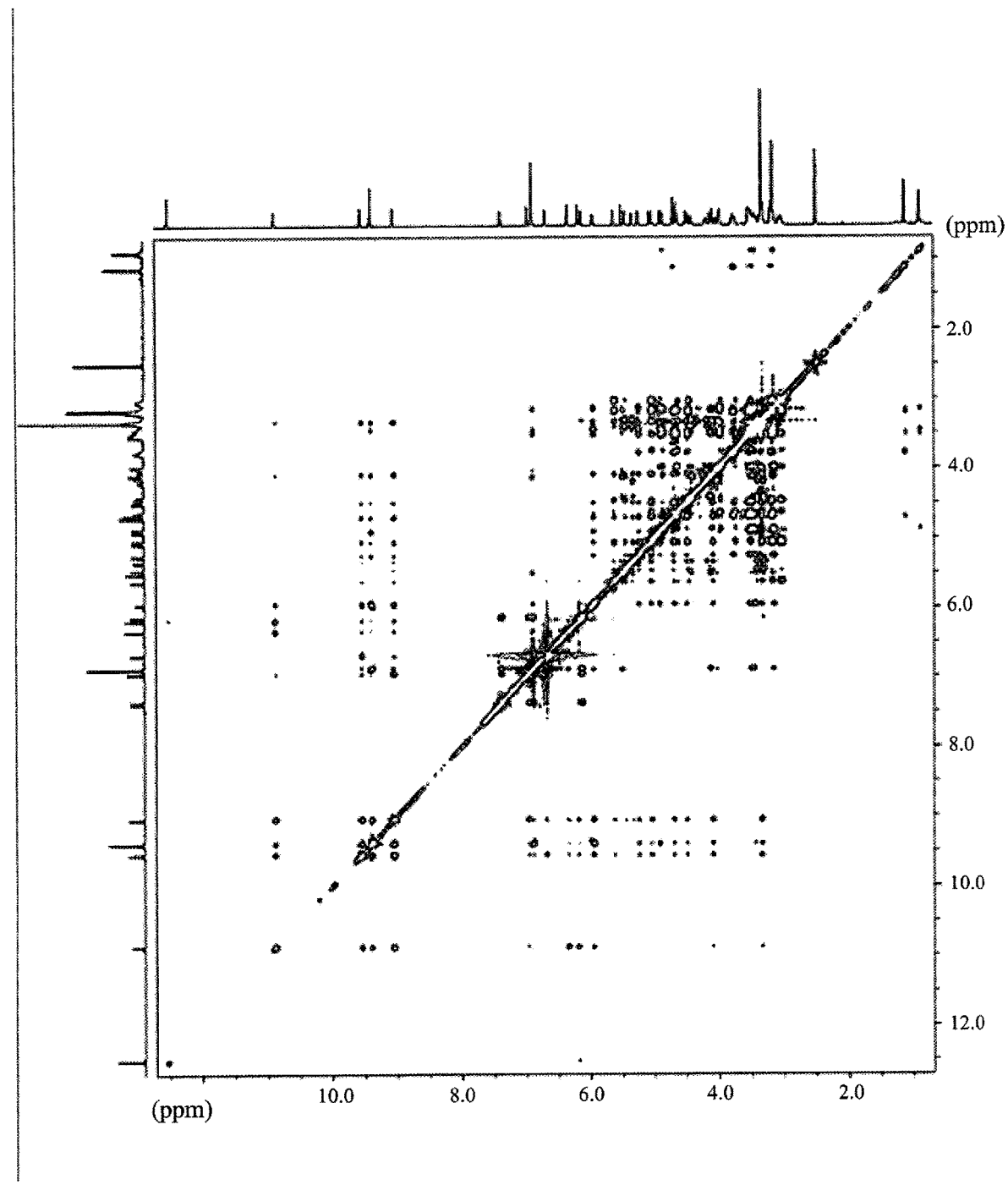
Figure 4A:
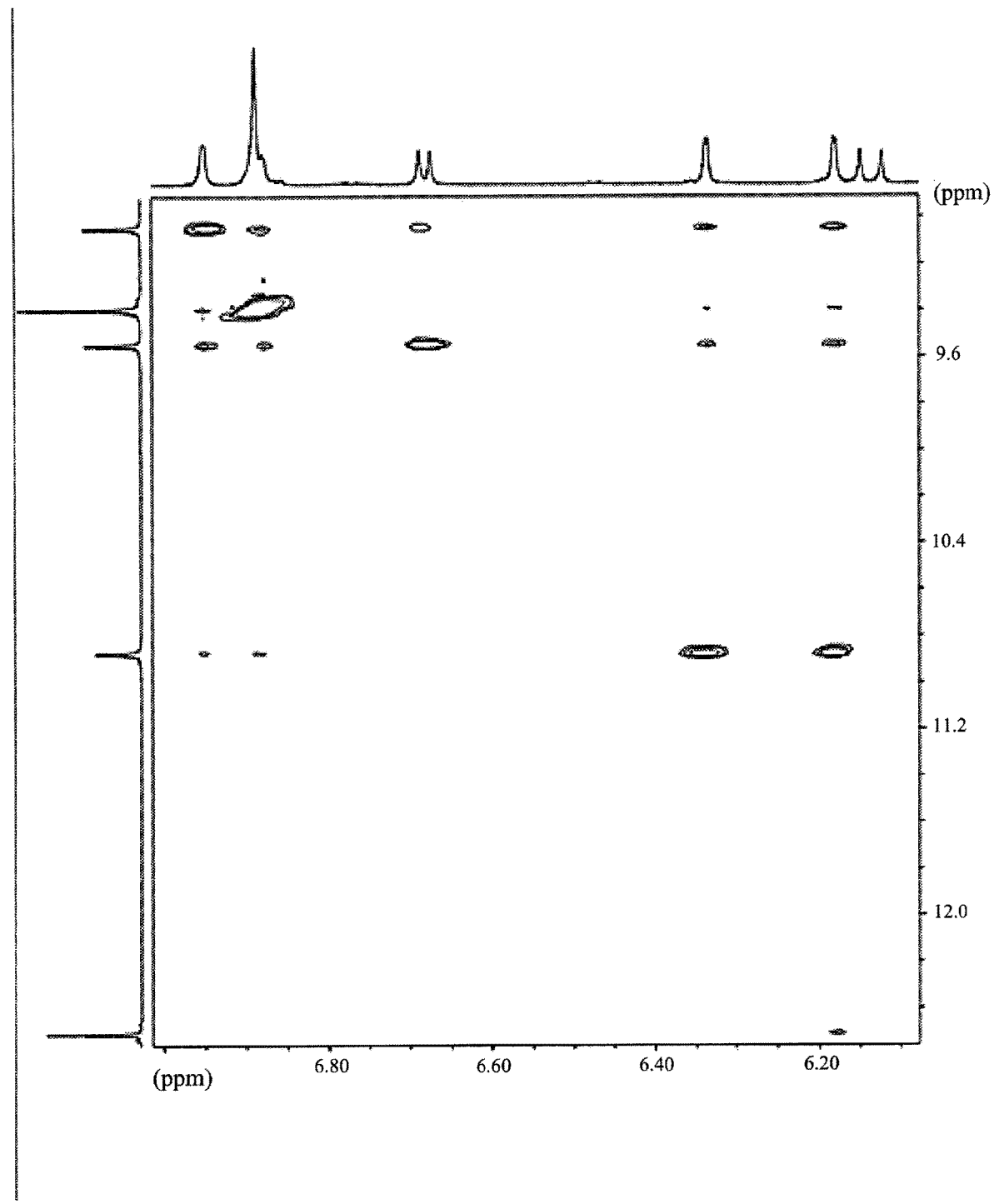

Interestingly, the results of a ROSEY NMR analysis suggested that this observed plane/plane interaction of MbA in the active site of HPA, is for the most part preformed when MbA is unbound and free in solution. As illustrated in FIG. 4, in this free unbound solution state, strong correlations were found between the H6 of myricetin (FIGS. 1, 4) and the 3OH of the caffeate ring, with peaks at 6.18 ppm and 9.05 ppm, respectively. Another strong correlation was found between the same hydrogen of the caffeoyl moiety (9.05 ppm) and the H8 of the myricetin group (6.34 ppm). Moderate strength correlations were also found between both H6 (6.18 ppm) and H8 (6.34 ppm) of myricetin and the 4OH of the caffeate (9.55 ppm). Further weak correlations were found between H2 of the caffeate ring (6.95 ppm) and the 7OH of myricetin (10.88 ppm), and between the 2' and 6' hydrogens of myricetin (6.89 ppm) and the methyl doublet of rhamnose 1 (0.88 ppm). All of these interactions are shown as dashed lines in FIG. 4B. Taken together these interactions serve to fix the required core inhibitor conformation of MbA as it approaches the active site of HPA. Nonetheless, as evident in FIG. 4, one adjustment would be necessary in the observed solution structure to obtain optimal correspondence with the HPA bound conformation. This would involve a 180° flip of the plane of the caffeate ring, presumably a conformational change easily accomplished by the free inhibitor in solution.

Figure 5A:
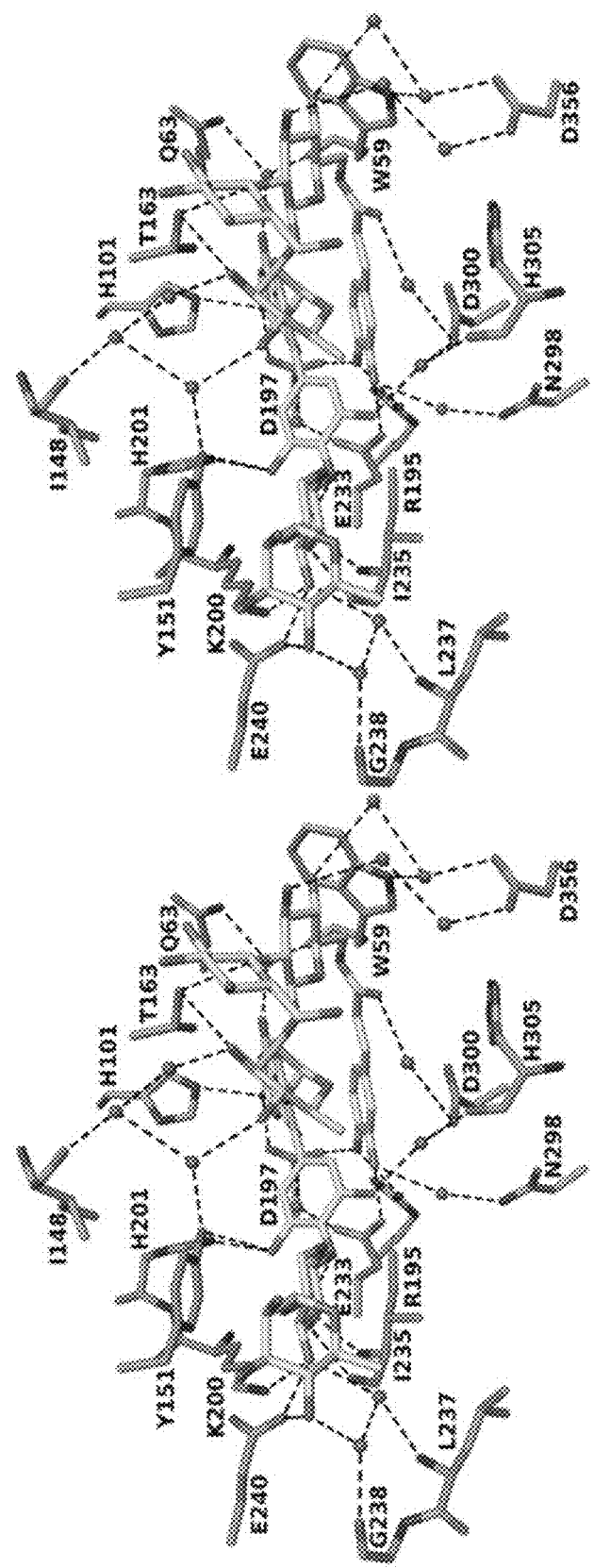
FIG. 5A shows the stereo diagram of the hydrogen bonding network formed upon the binding of MbA (center) to HPA (surrounding), with water molecules are drawn as small spheres

As evident from FIG. 5A, further strongly contributing factors to the nanomolar affinity that MbA demonstrates for the active site of HPA, is the impressive complement of hydrogen bonds formed between this inhibitor and the surface of HPA. The ring hydroxyls of the myricetin and caffeate groups play particularly important roles in binding through hydrogen bonds to the side chains of the catalytic residues D197 and E233. Additional water mediated interactions to these ring groups further serve to immobilize the side chain of the catalytic residue D300. Overall, the complementary fit of the MbA and HPA binding surfaces is apparent from the 14 direct hydrogen bonds formed, the additional 10 hydrogen bonds formed that are mediated by one water molecule and another 4 hydrogen bonds that involve 2 water molecules. A schematic diagram summarizing the full extent of the hydrogen bonding interactions present is shown in FIG. 5B.

Also important in establishing the specificity and affinity of MbA for HPA, are the presence of multiple well defined hydrophobic interactions. Prominent among these involve W58, which interacts with the plane of the caffeate ring, and Y62 which is at nearly a 90° angle to this ring. In addition, the side chains of L162 and L165 pack against the benzopyrone of myricetin, with the phenyl moiety of this latter group also packing against the side chain of I235. Notably, MbA sugar residues take further advantage of the placement of hydrophobic residues in the active site. For example, the hydrophobic side of the side chain of T163 packs against the C1 carbon of Rhamnose 1, while its side chain oxygen hydrogen bonds to Glucose1, and the side chain of Y151 packs against the Xylose residue (FIG. 5). These hydrophobic interactions, while fairly weak individually, help create an extremely tight fit of MbA in the enzyme's active site, and undoubtedly contribute to its specificity for HPA.

Figure 6A:
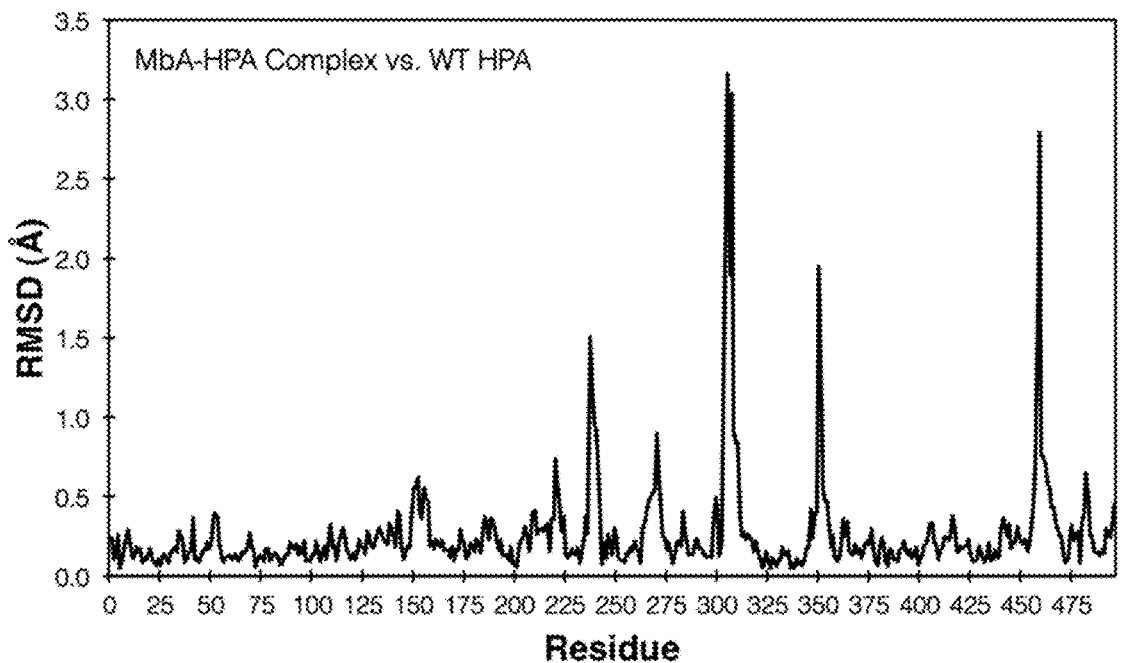
FIG. 6A shows plots of the average root mean square differences and FIG. 6B shows the normalized average thermal factors for main chain atoms of the H299N HPA-MbA complex and wild-type HPA (PDB ID 1 BSI), wherein the mean thermal factor B-value for the main chain of the polypeptide backbone in the MbA complex structure is drawn as a thin black line.

From a structural perspective it would seem that neither the complexation of MbA in the active site of HPA, nor the use of the H299N variant for these studies, significantly affects the protein fold of HPA. The average root mean square distance between corresponding main chain atoms of the MbA/H229N HPA complex and the inhibitor-free wild-type enzyme is only 0.26 Å. A residue-by-residue analysis of main chain positional shifts is shown in FIG. 6A, and identifies the largest displacements as occurring around residues 240, 305, 350 and 459.

Figure 6B:
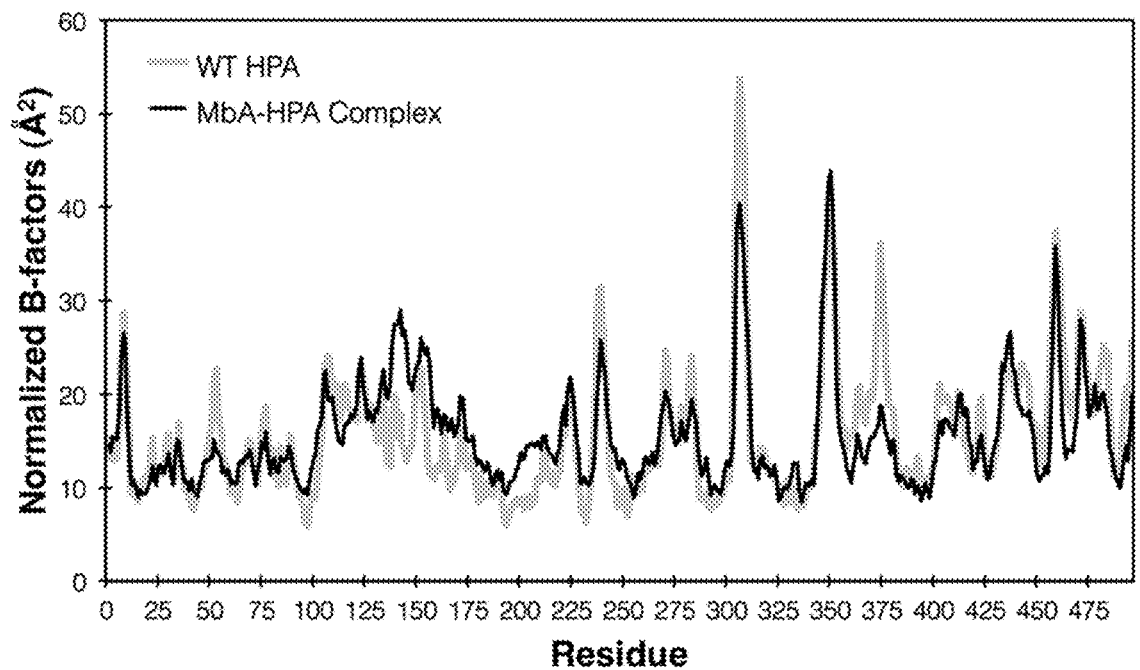

Polypeptide chain shifts in the region of E240 would appear to be the result of optimizing hydrogen bond interactions between the side chain of this residue and the Rhamnose2 and Xylose groups of MbA (FIG. 5). Also clearly affected by bound MbA, is the active site region in the vicinity of H305. In inhibitor-free wild-type HPA, residues 305-310 comprise a substrate-binding loop, but are substantially disordered (FIG. 6B; (1)). Nonetheless, this loop is found to become ordered and coalesce about bound inhibitors that mimic carbohydrate substrates (16). In such complexes, the side chain of H305 is found to shift towards bound inhibitor and directly hydrogen bound sugar residues in the S-2 binding subsite. The unique binding mode of MbA causes quite a different response, with H305 being shifted away from the active site region to avoid steric conflicts with the larger bulk of the MbA inhibitor. Indeed the whole substrate-binding loop comprised of residues 303-310 is similarly affected (FIG. 6A).

Coincident with the shift of polypeptide chain about H305, is an ~90° reorientation of the side chain of the catalytic residue D300, which would also form steric conflicts with bound MbA if it retained its wild-type enzyme conformation. Interestingly, in its new orientation, the side chain of D300 can now form a hydrogen bond with the shifted position of the side chain of H305 (FIG. 5). This is a new interaction not previously observed in inhibited or inhibitor-free wild-type enzymes.

The two regions of polypeptide chain displacements more remote from the active site region of HPA (FIG. 6A), primarily involve a flipped peptide bond at N350 and a β-turn variation at residue 459. However the significance of these two displacements is questionable given that these occur in regions of high polypeptide chain mobility (FIG. 6B) and are therefore poorly determined in electron density maps.

Our structural analyses also show that MbA does not interact with the site of the introduced H299N variant. The nearest approach the substituted asparagine residue has to MbA, occurs to the caffeate group which is ~6 Å distant. The void created between them is filled by well-spaced water molecules. Based on comparisons with wild-type HPA, there would seem to be more than sufficient space to accommodate a histidine side chain at this position when MbA is bound in the active site. Indeed, in this case the closest contact with MbA would remain >4 Å. The poorer $K_I$ of 124 nM observed for MbA inhibition of the H229N HPA variant enzyme, may reflect the less structured, more hydrated region adjacent to N299 in this variant, and the resultant looser fit of MbA to HPA in this area of the inhibitor-enzyme interface.

These structural studies clearly show the essential nature of the caffeate moiety of MbA in the specificity and affinity of this inhibitor for HPA. As FIG. 5 illustrates, when bound, this group is closely interfaced with the surface of HPA, forming multiple hydrogen bond interactions with nearby residues. These include the side chains of the catalytic residues D197 and E233; the side chain of the third catalytic residue D300 through a water molecule; the side chain of R195, a residue previously shown to modulate enzymatic activity (11, 32); and, the side chain of N298 through a water molecule, a residue notable for binding the allosteric chloride ion of HPA and stabilizing a nearby loop (11). Furthermore, beyond the π-stacking planar interaction formed with the myricetin ring of MbA, the caffeate group forms additional planar interactions with the side chains of W59 and Tyr62.

As such, the combined hydrophilic and hydrophobic contacts formed by the caffeate group serve to highly constrain its orientation in the active site next to catalytic residues, thereby providing an explanation for the large differences in kinetic results observed for naturally occurring caffeate variants found in montbretin isoforms B-E. For example, the exchange of the 3OH of caffeate in MbA for a hydrogen atom in MbB (FIG. 1) leads to an ~1000× decrease in inhibitory activity (5). From a structural perspective this is consistent with the expected loss of strong hydrogen bonding interactions to the side chains of E233 and N298 (through a water molecule) in MbB (FIG. 5). Even more difficult to accommodate would be the OMe of MbC (FIG. 1), where the dual effects of hydrogen bond loss and steric hindrance at the closely packed inhibitor/HPA interface would be expected to be significant. Not surprisingly, this MbC variant demonstrates a further 2× lower inhibition for HPA than MbB (FIG. 1). Interestingly, MbD and MbE, with 3H and 3OH on the caffeate ring, respectively, incorporate a further glucose residue at the 7OH position of the myricetin group (FIG. 1). As evident in FIG. 5, this additional glucose molecule would sterically clash with many other groups on the surface of HPA. These include the side chains of H101 and D197 to both of which the original 7OH of the myricetin forms strong hydrogen bonds, as well as the nearby side chains of Y62, A198 and the caffeate group of the inhibitor itself. This inability to accommodate an additional glucose residue at the inhibitor/HPA binding interface would serve to explain the poor inhibitory activity of both MbD and MbE (FIG. 1). Indeed, these results suggest that these two variants of MbA likely exhibit quite different binding modes on the surface of HPA. Overall, given the tight fit of MbA to the surface of HPA and the multitude of interactions formed as a result, it is hard to imagine isoforms of this inhibitor that would further enhance the binding observed for MbA.

Functional Analyses of MbA Substructures

Figure 7:
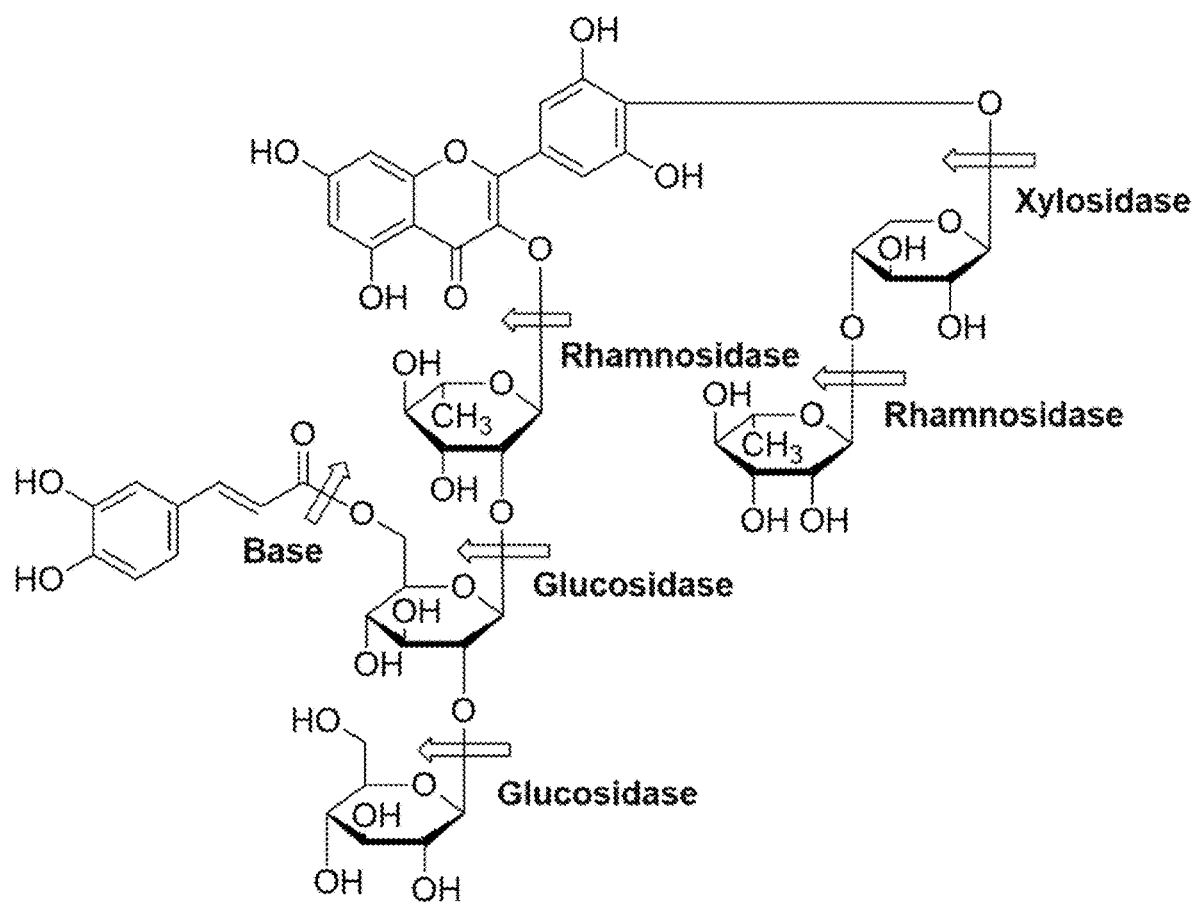
FIG. 7 shows an illustration of the specific points and agents of chemical and enzymatic cleavages used to fragment the structure of MbA to study the functional attributes of the various groups that comprise this inhibitor.

In an effort to clearly define all of the key characteristics that contribute to the specificity and affinity of MbA for HPA, we have examined the inhibitory properties of a series of MbA substructures. These smaller derivatives were generated by carrying out cleavages at specifically targeted bonds in MbA by chemical or enzymatic means (FIG. 7). The standard for inhibitory activity comparisons of the substructures obtained, was the benchmark $K_I$ value of 4.4 nM observed for intact MbA (FIG. 1, TABLE 2).

TABLE 2 below shows schematic diagrams of intact MbA and derivative products, with associated $K_I$ inhibition values for the binding of these compounds to HPA, wherein MbA groups are indicated by 'G' for glucose; 'C' for ethyl caffeate; 'R' for rhamnose; 'M' for myricetin; and, 'X' for xylose.

TABLE 2

| Structures | $K_i$ of HPA (nM) |
|---|---|
| MbA  C–G–G–R–M–X–R | 4.4 ± 0.4 |

TABLE 2-continued
| | Structures | $K_i$ of HPA (nM) |
|---|---|---|
| MbA-1 | 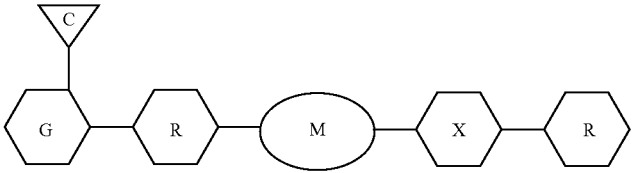 | 9.1 ± 0.8 |
| MbA-R | 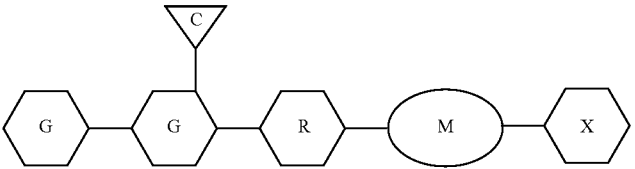 | 21.3 ± 2.2 |
| MbA-RX | 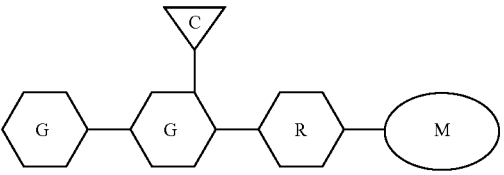 | 42.4 ± 5.3 |
| MbA-1GR | 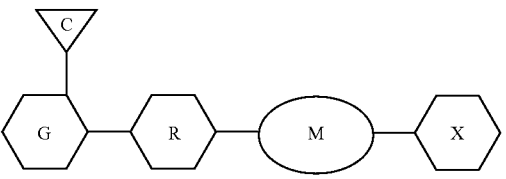 | 79.3 ± 9.5 |
| MbA-1GRX | 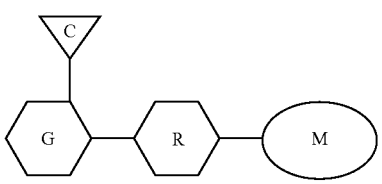 | 93.3 ± 7.6 |
| MbA-2 | 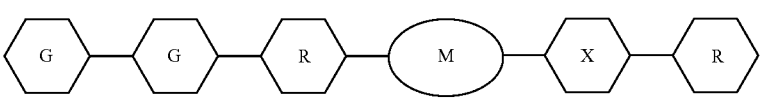 | 730 ± 90 |
| MbA-3 | 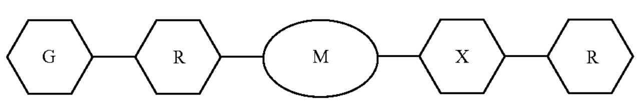 | 2240 ± 200 |
| MbA-2R | 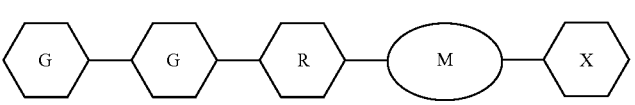 | 46800 ± 3900 |
| MbA-3GR | 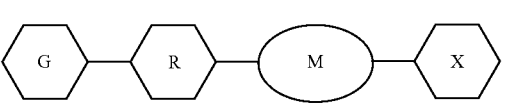 | 128000 ± 15000 |

Figure 3A:
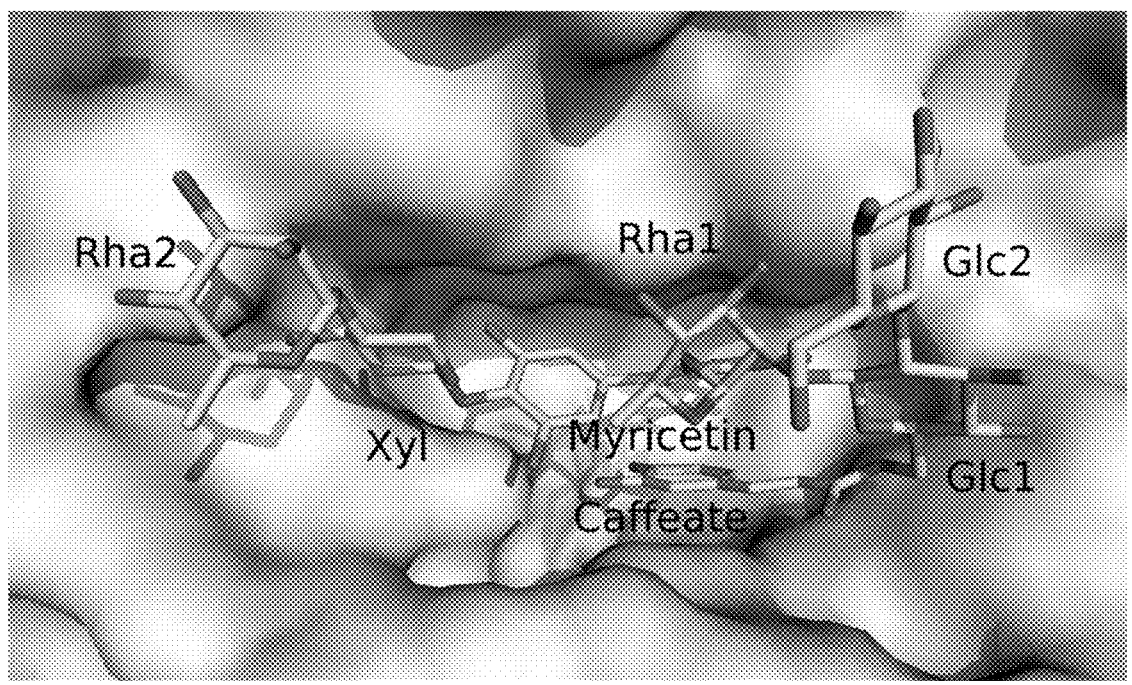
FIGS. 3A-3B show a solid surface model of the HPA active site region with the bound conformation of MbA drawn two ways: stick (FIG. 3A) and space-filling modes (FIG. 3B), wherein the inhibitor binds near all three catalytic residues and completely occludes substrate access to the active site of HPA.
Figure 3B:
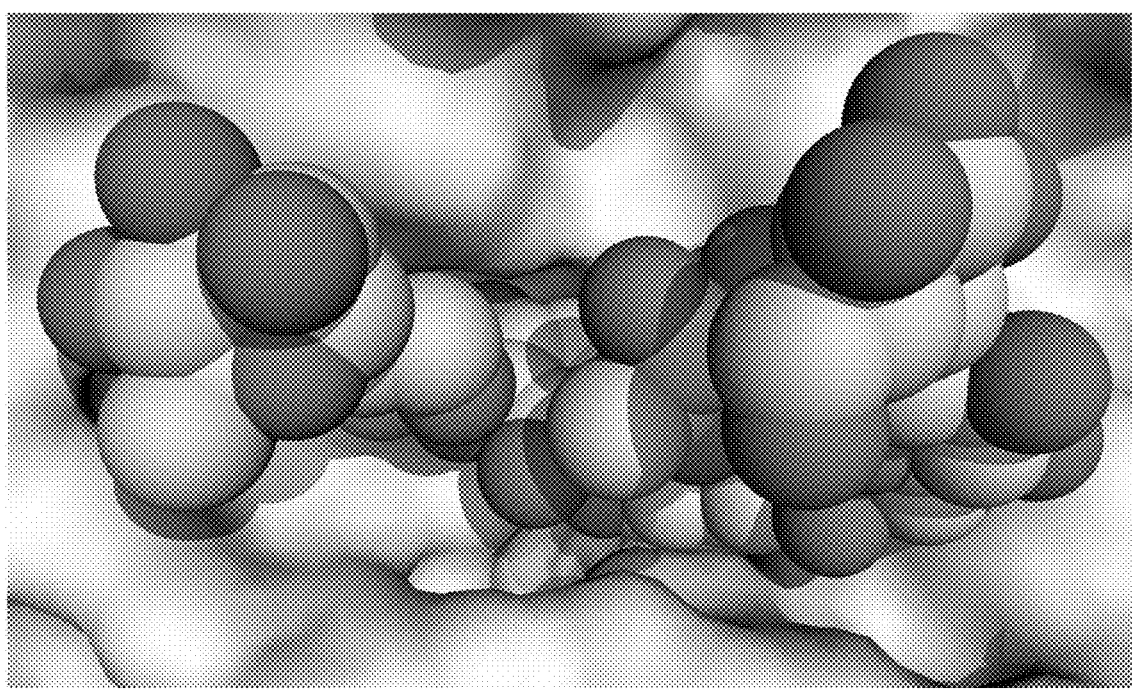

It is evident from these analyses that removal of the terminal Glucose2 (substructure MbA-1; TABLE 2) has only a marginal effect on overall MbA inhibition, with $K_I$ now becoming 9 nM. Our structural studies are consistent with this conclusion, given that Glucose2 is projected largely away from the protein surface (FIG. 3). In fact, this group's only interaction with the surface of HPA is a weak hydrogen bond from the β-link formed to the adjacent Glucose1, to the side chain of T163 (FIG. 5). The limited interaction of Glucose2 with the surface of HPA is also reflected in the average thermal B factor value of 41.5 $Å^2$ observed for the non-hydrogen atoms of this group, compared to this value for MbA as a whole (22.7 $Å^2$).

Nonetheless, examination of further MbA substructures indicates it is possible that the primary role of Glucose2 may be in assisting the formation of the productive conformation of bound MbA through an intramolecular bond from its O5 to the O3 OH of Rhamnose1. However, as discussed later herein, this effect would appear to be further dependent on the presence of the Rhamnose2 residue. Notably ROSEY NMR results also indicate that Rhamnose1 further interacts with the B-ring of the myricetin group in forming a productive inhibitory complex in the active site of HPA (FIG. 4).

Removal of only the terminal Rhamnose2 residue at the other extremity of MbA (substructure MbA-R; FIG. 7; TABLE 2) also has a minimal impact on inhibitory activity with $K_I$ measured as 21 nM in this case. Like Glucose2, Rhamnose2 has minimal contact with the protein surface (FIGS. 3 and 5), interacting only through a hydrogen bond to the side chain of E240 and a weaker water mediated interaction to the carbonyl of G238. Thermal analyses of the average B value of the atoms of this sugar (29.6 $Å^2$) also indicate a weaker association with the protein surface compared to that of MbA as a whole (22.7 $Å^2$).

Additional removal of the Xylose residue next to Rhamnose2, has a much larger impact on observed HPA inhibition (substructure MbA-RX; $K_I$=43 nM), reflecting the stronger interactions this residue forms to the enzyme surface. This is also apparent in the lower average thermal B value of 16.6 $Å^2$ for the atoms of the Xylose residue. In total three hydrogen bonds are formed to this residue, two of which involve the charged side chains of E240 and K200.

Interestingly, removal of both the terminal Glucose2 and Rhamnose2 residues (substructure MbA-1GR, FIG. 7; TABLE 2), has a much larger cumulative effect on inhibitory activity than expected, with $K_I$ reduced to 79 nM. It would seem that although observed protein surface interactions are minimal, these two residues work in synergy to assist in the productive inhibitory orientation/conformation of the full MbA structure in the active site of HPA. Subsequent removal of all three of the outer residues, Glucose2, Rhamnose2 and Xylose (substructure MbA-1GRX), has little additional impact on $K_I$ (79 vs. 93 nM). Remarkably this minimal core structure is only ~25× poorer at binding to the active site of HPA than the full structure of MbA ($K_I$=4.4 nM).

Attesting to the critical contribution of the caffeate group to the inhibitory activity of MbA, further analyses of more linear substructures (FIG. 7; TABLE 2), in which the caffeate group has been removed, show these to be uniformly very poor inhibitors. For example, substructure MbA-2, which retains all the structural features of MbA, except for the caffeate group, results in a $K_I$ of 730 nM. This no doubt reflects the removal of the key core π-stacking arrangement between the caffeate and myricetin groups, and the loss of the many hydrogen bonds formed directly to the caffeate group (FIG. 5). As TABLE 2 indicates, further removal of flanking residues in substructures without the caffeate group, lead to even poorer inhibitors.

MbA Derivative Structures

A number of compounds derived from MbA and having various linker (A) configurations are shown in TABLE 3 below.

TABLE 3

| Compound Identifier | Compound Structure |
|---|---|
| MbA-1GRX | 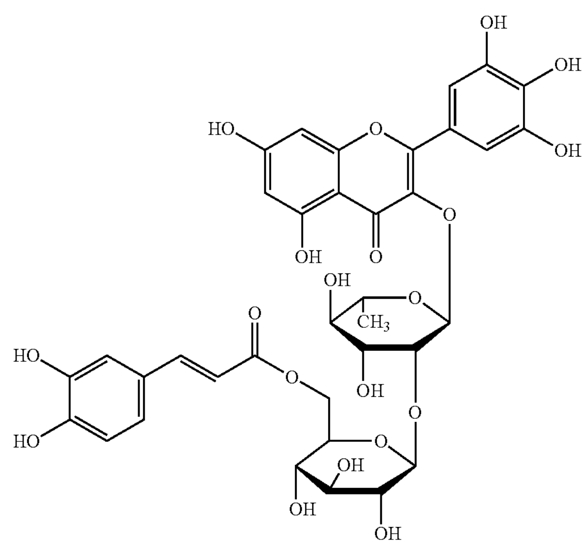  |

TABLE 3-continued
| Compound Identifier | Compound Structure |
|---|---|
| MbA-1GR | 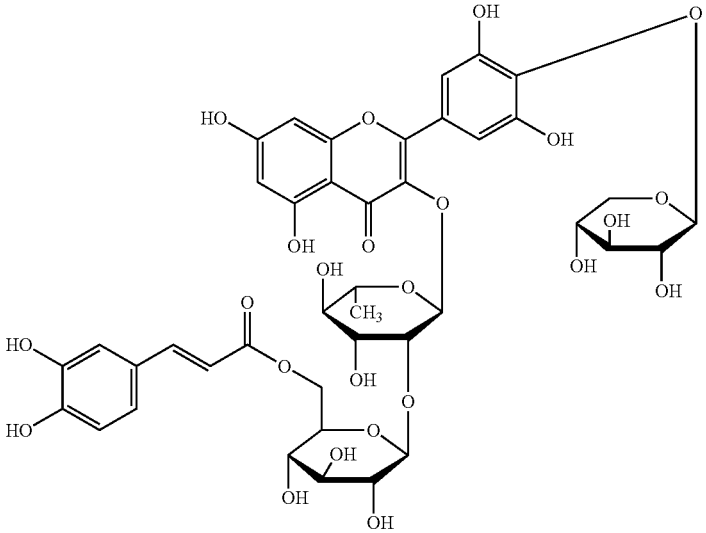 |
| MbA-RX | 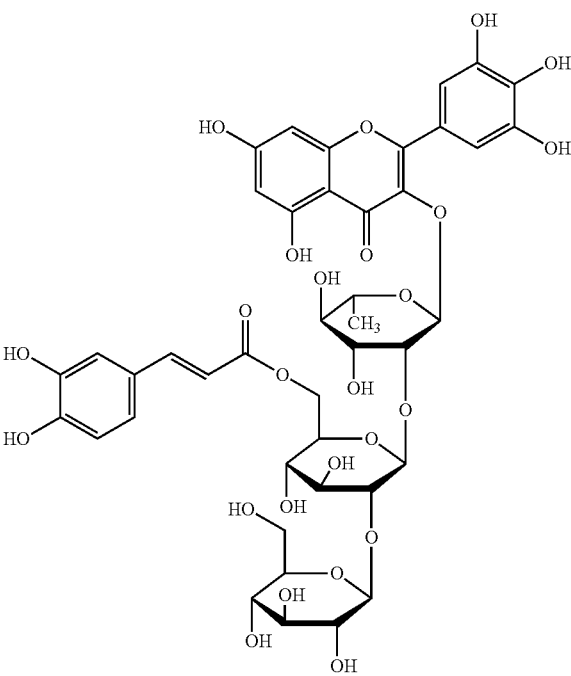 |

TABLE 3-continued
| Compound Identifier | Compound Structure |
|---|---|
| MbA-R | 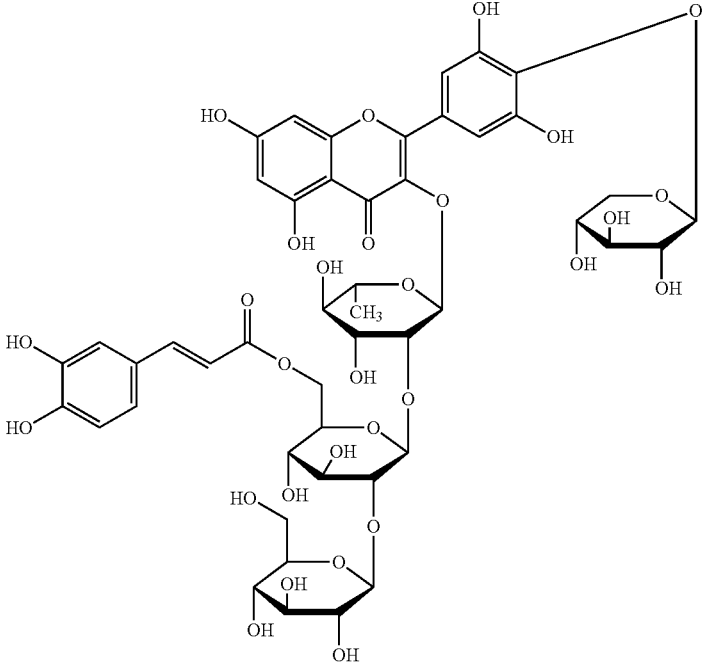 |
| 11 (6-aminoGlc) | 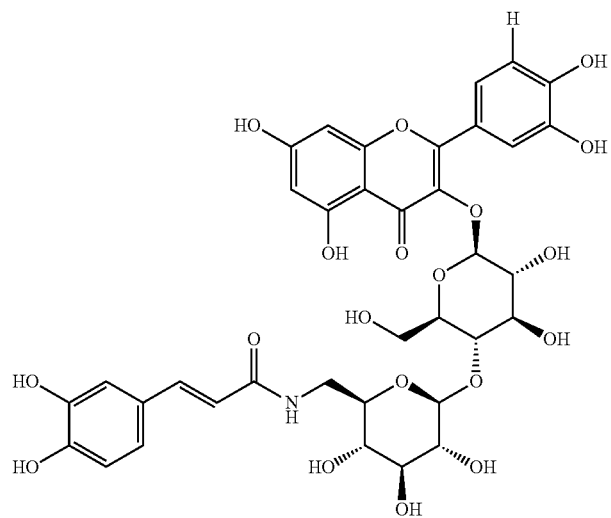 [SMILES: O=C(/C=C/c1ccc(O)c(O)c1)NC[C@H]1O[C@@H](O[C@H]2[C@H](O)[C@@H](O)[C@H](Oc3c(-c4ccc(O)c(O)c4)oc4cc(O)cc(O)c4c3=O)O[C@@H]2CO)[C@H](O)[C@@H](O)[C@@H]1O] |

TABLE 3-continued
| Compound Identifier | Compound Structure |
|---|---|
| 12 (4-aminoGal) | 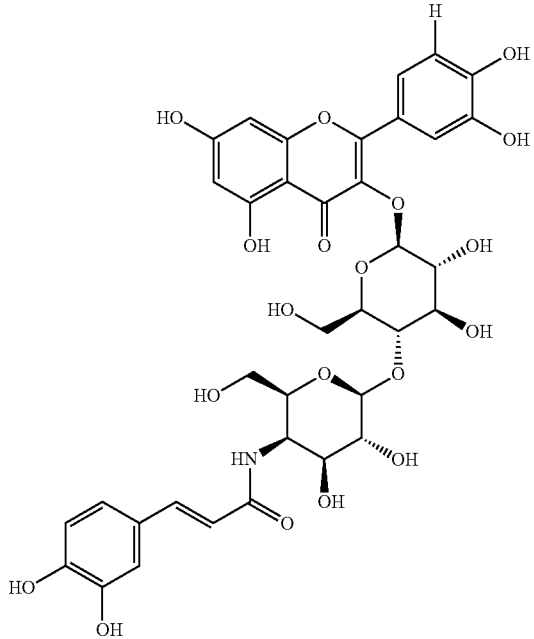 [SMILES: O=C(/C=C/c1ccc(O)c(O)c1)N[C@@H]1[C@H](O)[C@@H](O)[C@H](O[C@H]2[C@H](O)[C@@H](O)[C@H](Oc3c(-c4ccc(O)c(O)c4)oc4cc(O)cc(O)c4c3=O)O[C@@H]2CO)O[C@@H]1CO] |
| 13 (4-aminoGlc)) | 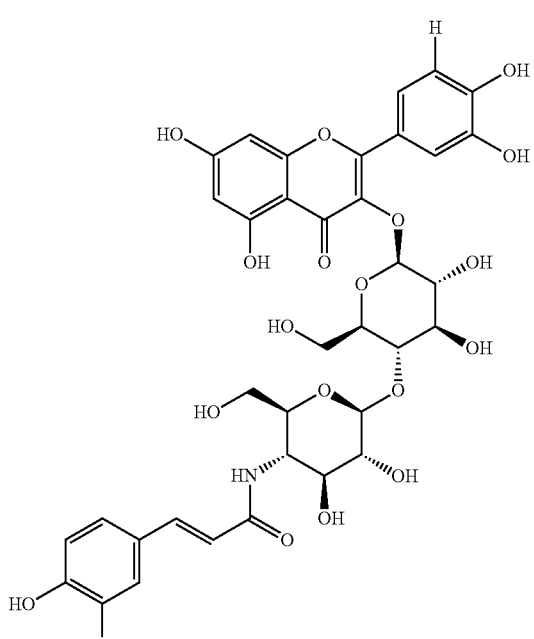 |

TABLE 3-continued

| Compound Identifier | Compound Structure |
| --- | --- |
| 5a* | 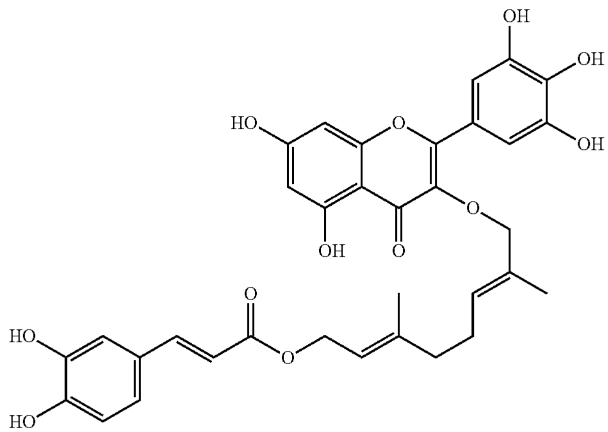 [SMILES: C/C(=C\COC(=O)/C=C/c1ccc(O)c(O)c1)CC/C=C(\C)COc1c(-c2cc(O)c(O)c(O)c2)oc2cc(O)cc(O)c2c1=O] |
| 5b* | 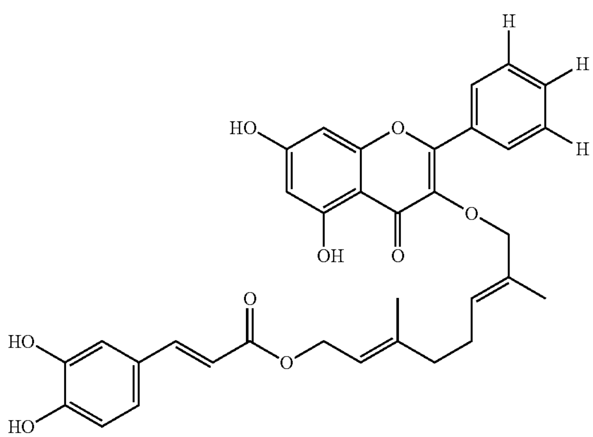 [SMILES: C/C(=C\COC(=O)/C=C/c1ccc(O)c(O)c1)CC/C=C(\C)COc1c(-c2ccccc2)oc2cc(O)cc(O)c2c1=O] |
| 4a* | 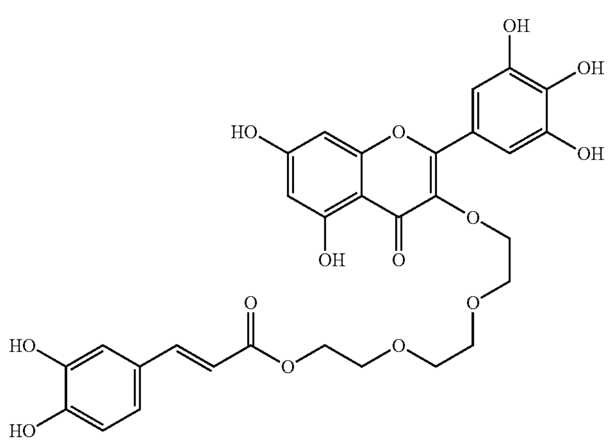 [SMILES: O=C(/C=C/c1ccc(O)c(O)c1)OCCOCCOCCOc1c(-c2cc(O)c(O)c(O)c2)oc2cc(O)cc(O)c2c1=O] |

TABLE 3-continued
| Compound Identifier | Compound Structure |
|---|---|
| 4b* | 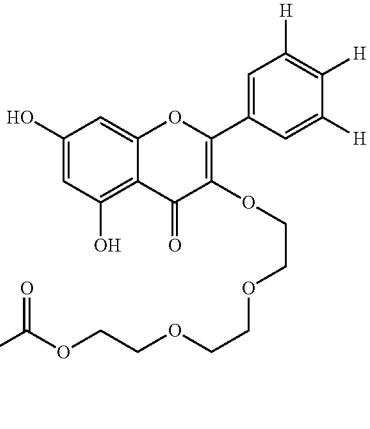 |
| awm-teg | 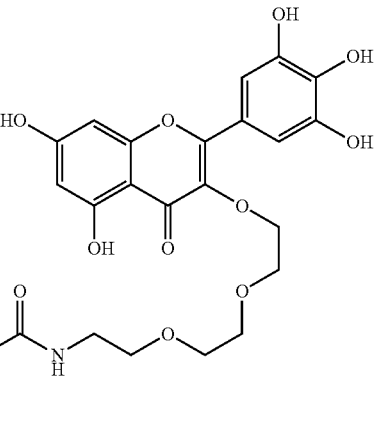 |
| 3a* | 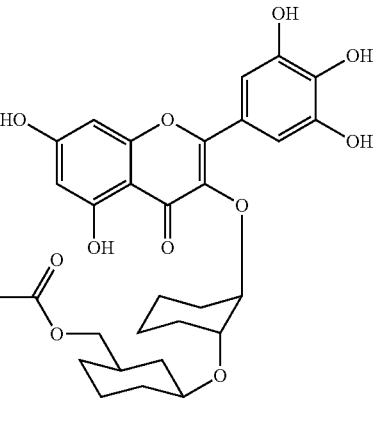 |

TABLE 3-continued

| Compound Identifier | Compound Structure |
|---|---|
| 3b* | 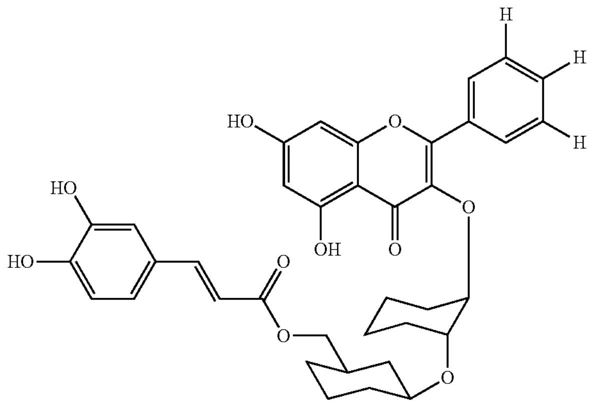 [SMILES: O=C(/C=C/c1ccc(O)c(O)c1)OCC1CCCC(OC2CCCCC2Oc2c(-c3ccccc3)oc3cc(O)cc(O)c3c2=O)C1] |
| 2b* | 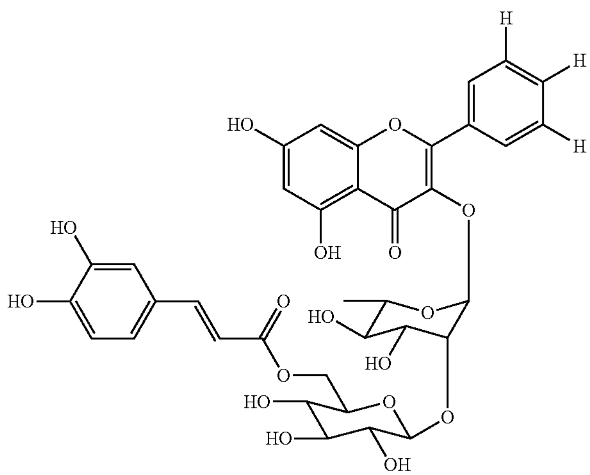 [SMILES: CC1OC(Oc2c(-c3ccccc3)oc3cc(O)cc(O)c3c2=O)C(OC2OC(COC(=O)/C=C/c3ccc(O)c(O)c3)C(O)C(O)C2O)C(O)C1O] |
| 10 | 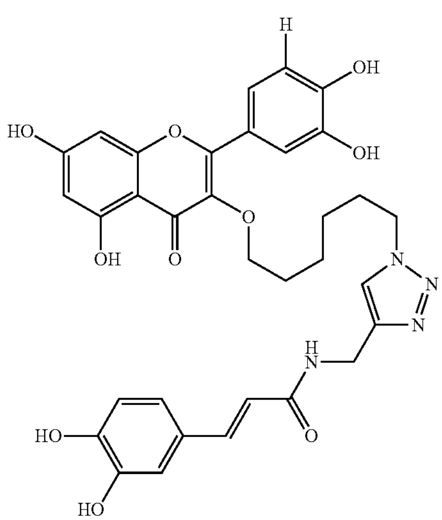 [SMILES: O=C(/C=C/c1ccc(O)c(O)c1)NCc1cn(CCCCCCOc2c(-c3ccc(O)c(O)c3)oc3cc(O)cc(O)c3c2=O)nn1] |

TABLE 3-continued
| Compound Identifier | Compound Structure |
|---|---|
| 6 | 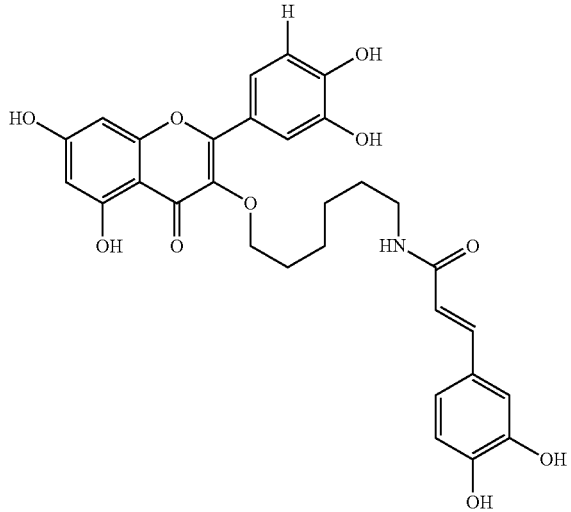 [SMILES: O=C(/C=C/c1ccc(O)c(O)c1)NCCCCCCOc1c(-c2ccc(O)c(O)c2)oc2cc(O)cc(O)c2c1=O] |
| 02 | 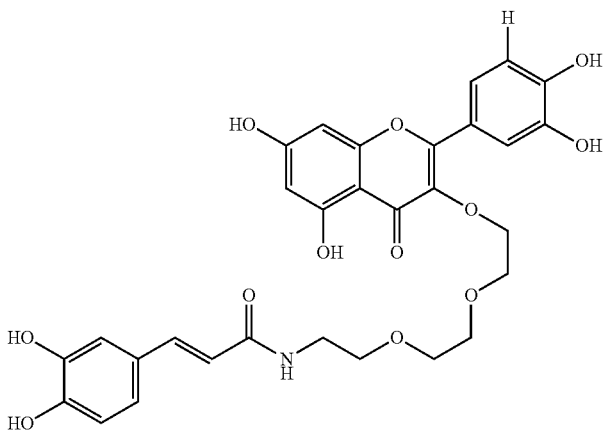 [SMILES: O=C(/C=C/c1ccc(O)c(O)c1)NCCOCCOCCOc1c(-c2ccc(O)c(O)c2)oc2cc(O)cc(O)c2c1=O] |
| 03 | 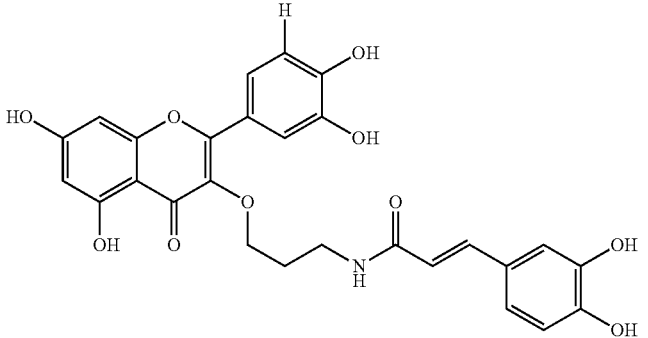 [SMILES: O=C(/C=C/c1ccc(O)c(O)c1)NCCCOc1c(-c2ccc(O)c(O)c2)oc2cc(O)cc(O)c2c1=O] |

TABLE 3-continued

| Compound Identifier | Compound Structure |
|---|---|
| 04 | *(chemical structure: myricetin core with O-linked pentyl chain terminating in NH-C(=O)-CH=CH-(3,4-dihydroxyphenyl) caffeate amide)* |
| 05 | *(chemical structure: myricetin core with O-linked hexyl chain terminating in NH-C(=O)-CH=CH-(3,4-dihydroxyphenyl) caffeate amide)* |

*compounds were not made nor tested

Comparative Analyses: MbA and Myricetin/Ethyl Caffeate Inhibition

Many different flavonols and their substituted counterparts have been shown to be inhibitors of the highly homologous human pancreatic and salivary α-amylases, albeit with considerably less affinity and specificity than observed for MbA (7, 33). Included in this group is the myricetin core of MbA, which by itself, is an α-glucosidase inhibitor with a measured $K_I$ of 110 μM against HPA (5). As illustrated in FIG. 8, it is clear from our past work in solving the structure of the myricetin/HPA inhibitory complex (Brayer, unpublished data), and our current studies of MbA complexation, that while the binding modes of these two inhibitors do share some common characteristics, overall they are markedly different.

Notably in common, the flavonol groups of both of these inhibitors are bound adjacent to catalytic residues and significantly, along the same conformational plane (FIG. 8). Also similar in both cases, is the displacement of the active site residues D300 and H305, as well as the outward movement of the flexible substrate-binding loop of HPA. However, the orientations of the three aromatic rings of myricetin in each case, is very distinctive. For bound myricetin alone, the absence of additional ring substitutions allows for considerably more flexibility in binding mode and this appears to lead to the unique binding orientation observed. In this case, the B-ring of the myricetin group occupies the comparable position of the C-ring of MbA (FIGS. 1 and 8). This reorientation, coupled with an ~120° rotation of the myricetin group as a whole, would seem to be favored since it places an additional ring hydroxyl group in the active site adjacent to catalytic residues. Another result of this unique binding mode by myricetin alone, is that it's A/C-rings are now projected into a new area of the active site cleft of HPA (FIG. 8), that more closely follows the path of inhibitors that mimic normal carbohydrate substrates (subsites −1 and −2). For MbA, this conformation of its myricetin group is disallowed, since its orientation is highly constrained by the presence of the other bulky groups that make up this inhibitor and by the manner in which these latter groups interact with each other and the active site surface of HPA.

It has also been found that ethyl caffeate by itself, can act as an inhibitor of HPA with a $K_I$ of 1.3 mM (5). As part of the structure of MbA, ethyl caffeate is an integral component of the inhibitory complex with HPA, participating in both a key π-stacking interaction with the myricetin group and being involved in direct hydrogen bonding to catalytic residues (FIGS. 5 and 8). In contrast, when ethyl caffeate is bound alone, its mode of inhibition of HPA is via a very different mechanism (Brayer, unpublished data). Specifically, three ethyl caffeates are found to bind simultaneously on the surface of HPA, all remotely from the active site region in individual binding pockets. Collectively these inhibitor molecules have been shown to promote disorder in the four polypeptide chain segments that make up the majority of the extended substrate binding cleft of HPA. Surprisingly, none of the identified ethyl caffeate binding sites are near that for this group in the MbA inhibitory complex, nor are any of these sites in common with any other known HPA inhibitors. Clearly, ethyl caffeate by itself demonstrates a uniquely novel inhibitory mechanism when unrestrained by being part of a larger inhibitor such as MbA.

The Uniqueness of MbA Inhibition

Our structural studies clearly show that MbA utilizes a completely different mode of HPA inhibition from that previously observed. This is particularly evident in FIG. 9A, which compares the conformation of bound MbA with that of the pseudo-pentasaccharide inhibitor acarbose. This latter transition state based inhibitor has been shown to be a good model for the expected binding mode of polymeric glucose substrates in the active site of HPA (10, 16, 29-31). In the acarbose/HPA inhibitor complex, individual inhibitor sugar residues are each found bound in one of the five well formed, high affinity binding subsites that line the extended HPA substrate binding cleft (16). This binding mode in turn, positions the putative scissile bond between the −1 and +1 binding subsites adjacent to the catalytic residues D197, E233 and D300. Coincident with acarbose binding, there is a rearrangement of the nearby flexible substrate binding loop to optimize protein/inhibitor interactions, particularly for the side chains of D300 and H305, which each form direct hydrogen bonds to bound sugars.

Figure 9A:
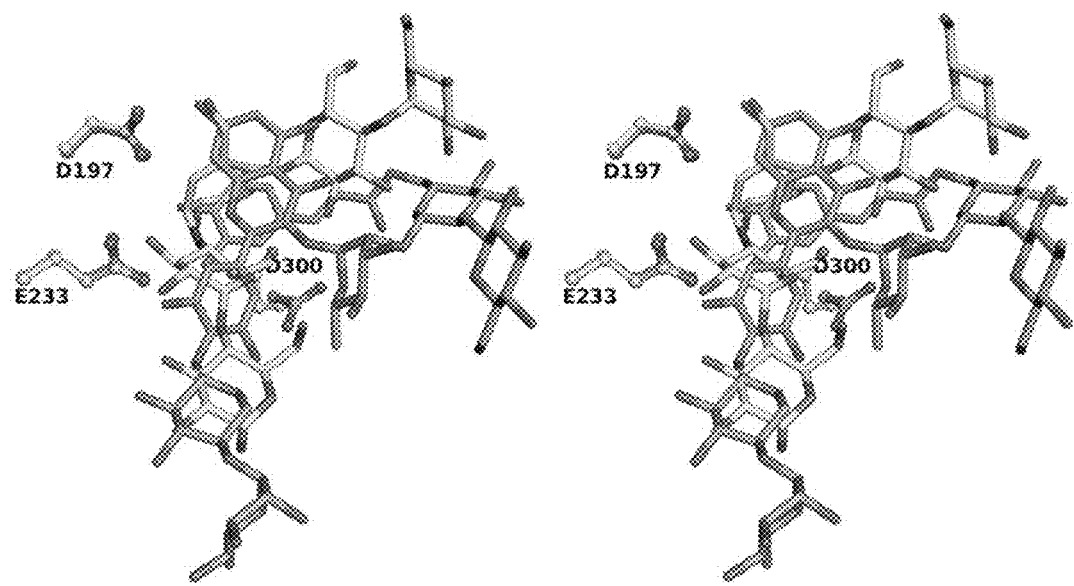
FIG. 9A shows stereo drawings of the overall conformations of the bound inhibitors MbA (medium grey) and acarbose (light grey (16)) in the active site of HPA.
Figure 9B:
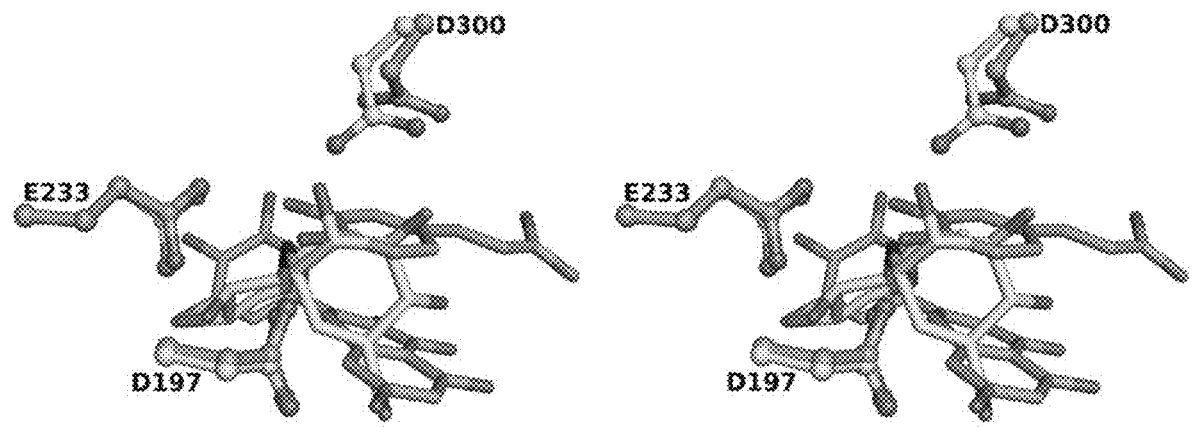
FIG. 9B shows a close-up view of the myricetin and caffeate moieties of enzyme bound MbA (medium grey), overlaid with the non-covalently bound conformation of the N-linked valienamine and 6-deoxyglucose rings of acarbose (light grey). These drawings clearly illustrate the very different modes of binding exhibited by these inhibitors adjacent to catalytic residues. Notably, the spacing of the π-stacked MbA caffeate and myricetin groups closely approximates the diameter of the valienamine ring.

In contrast, MbA binds HPA in a distinctly different manner. Surprisingly, given its high affinity and specificity for HPA, the mode of MbA inhibition does not appear to be mechanism based, either as a mimic of the catalytic transition state like acarbose, or of any other step in normal polymeric glucose cleavage. Indeed as FIG. 9A shows, none of the sugar residues that make up MbA are positioned near catalytic residues and none of these occupy the usual glucose binding subsites as defined by inhibitors like acarbose. Instead, the valienamine residue of acarbose that acts as a transition state analogue of a normal glucose in subsite −1, is substituted by the two stacked and perpendicularly oriented planar groups of MbA (myricetin and ethyl caffeate) with multiple ring hydroxyl groups to fully engage the hydrogen bonding potential of catalytic residues. Notably, these planar groups bracket the diameter of a bound valienamine and thereby fill the available space in the −1 and +1 binding subsites, across which lies the normal positioning of a scissile bond (FIG. 9B). The inhibitory aspect of this binding mode is additionally enhanced by the displacement of two other elements key to substrate binding, namely D300 and H305. The central planar hydrophobic core of MbA is further held in place by an array of novel hydrogen bonds and hydrophobic interactions formed by peripheral sugar groups (FIGS. 3 and 5). Taken together, the inhibitory features of MbA can be characterized more as an exercise in substrate exclusion through high affinity binding in the active site of HPA, rather than an attempt to mimic the catalytic process carried out by this enzyme.

Comparative Analyses: MbA and Disaccharide Linkers

Montbretin A is compared to Quercetin/Myricetin and 3 disaccharide linker compounds (6-aminoGlc), 12 (4-aminoGal) and 13 (4-aminoGlc) as shown in TABLE 4 below.

TABLE 4

| Comparative Analyses of MbA and Disaccharide Linkers | |
|---|---|
| Molecule | $K_i$ (HPA Inhibition) |
| Montbretin A | 8 nM |
| Quercetin/Myricetin | 100 μM |
| 11 (6-aminoGlc) | 70 μM |

TABLE 4-continued

| Comparative Analyses of MbA and Disaccharide Linkers | |
|---|---|
| Molecule | $K_i$ (HPA Inhibition) |
| 12 (4-aminoGal) | 45 μM |
| 13 (4-aminoGlc) | — |

Although the inhibitory activities for the disaccharide compounds 11 (6-aminoGlc) and 12 (4-aminoGal) is not as potent as montbretin A, there is a significant improvement over Quercetin/Myricetin alone. Furthermore, these compounds verify the flexibility in selecting a linker (A).

Comparative Analyses: MbA and Non-saccharide Linkers

Montbretin A is compared to Quercetin/Myricetin and 5 non-saccharide linker compounds 10, 02, 03, 04 and 05 as shown in TABLE 5 below.

TABLE 5

| Comparative Analyses of MbA and Non-saccharide Linkers | |
|---|---|
| Molecule | $K_i$ (HPA Inhibition) |
| Montbretin A | 8 nM |
| Quercetin/Myricetin | 100 μM |
| 10 | 14 μM |
| 02 | 82 μM |
| 03 | 145 μM |
| 04 | 5 μM |
| 05 | 4 μM |

As shown in TABLE 5, the activities of non-saccharide linker compounds (compounds 10, 02, 03, 04 and 05) are shown in comparison to montbretin A, which still shows greater inhibition of HPA. Interestingly, the non-saccharide linker compounds, for the most part, show a significant improvement over Quercetin/Myricetin. Furthermore, these compounds verify the flexibility in selecting a linker (A). The drop in activity for 03 may reflect the linker length of only 3 carbons, whereas 5 linker carbons in compound 04 and 7 linker carbons showed a vast improvement in activity. Also, interestingly, the addition of linker chain oxygens in to the linker of 02 seemed to decrease inhibitory activity, despite having a length of 6 carbons and 2 oxygens. These compounds also show a change from an ester linkage (X) to an amide linkage (X) which is meant to improve stability of the compounds.

Comparative Analyses: Inhibition of HPA and other α-glycosidases by MbA and Disaccharide Linkers Although previous studies with a range of largely commercially available glycosidases had demonstrated that MbA was a specific amylase inhibitor (5), no data were collected on the inhibition of intestinal α-glucosidases or amylases found in gut bacteria in those early studies. Accordingly, a determination of whether MbA showed the requisite specificity between human enzymes was undertaken. Neither the human maltase-glucoamylase (MGAM) nor the human sucrose isomaltase (SI) was inhibited by MbA, even at concentrations up to 500 μM (TABLE 6), thereby clearly showing the desired specificity. This may, in part, be due to the fact that these human brush border α-glucosidases are all members of CAZy (Carbohydrate-Active Enzymes Database) family GH31, which is distinct in sequence and structure from the GH13 family to which HPA belongs (37, 38). Further, the analysis of representative gut bacterial amylases revealed that one of them was not inhibited at all, and the other only relatively weakly (Ki=1.6 µM). Since it was possible that the 'terminal' sugars (Glc, Rha and Xyl) might be providing the specificity for HPA over the α-glucosidases by sterically occluding the binding of the core structure containing the two aromatics, inhibition studies were also performed on these enzymes with MbA-GRX. No inhibition of maltase-glucoamylase was observed, and although inhibition of sucrose-isomaltase could now be seen, it remained very weak, at an IC50 of 75.5 µM as shown in TABLE 6 below.

TABLE 6

Comparative Analyses of MbA and Disaccharide Linkers

| Enzyme | GH Family | $K_i$ with MbA (nM) | $K_i$ With MbA-GRX (nM) |
| --- | --- | --- | --- |
| HPA | 13 | 8.1 ± 0.4 | 93.3 ± 7.6 |
| Roseburia inulinivorans Amy A | 13 | NI[a] | NI[b] |
| Butyrivibrio fibrisolvens Amy B | 13 | 1,600 ± 170 | ND[c] |
| Homo sapiens ntMGAM | 31 | NI[a] | NI[b] |
| H. sapiens ctMGAM | 31 | NI[a] | NI[b] |
| H. sapiens ctSI | 31 | NI[a] | IC$_{50}$ = 75,500 ± 2,500 |

[a]No inhibition at concentrations of 500 µM.
[b]No inhibition at concentrations of 100 µM.
[c]Not determined.
Amy, amylase; ntMGAM, N-terminal domain of maltase glucoamylase; ctMGAM, C-terminal domain of maltase-glucoamylase; ctSI, C-terminal domain of sucrose-isomaltase. Ki values represent mean values ± s.d. and derive from at least 20 data points in each case, determined in duplicate.

Experimental Procedures

All buffer chemicals and reagents were obtained from Sigma/Aldrich Canada™ unless otherwise stated. 2-Chloro-4-nitrophenyl α-maltotrioside (αCNP-G3) was a kind gift from GelTex Pharmaceuticals.

Bacterial Strain, Media, and Plasmids. Escherichia coli DH$_5$R subcloning efficiency competent cells were obtained from Gibco BRI™ and were used for all transformations and DNA manipulations according to standard procedures (9). Pichia pastoris strain GM5011 was used for the expression of wild-type and H299N variant proteins. Growth and expression media were prepared as published in the Pichia expression kit (Invitrogen™). Methods for the construction of expression vectors for wild-type HPA and the H299N variant have been described previously (10, 11).

HPA Expression and Purification. Transformation of HPA plasmids into P. pastoris cells and cell selection were carried out according to the directions in the Pichia expression kit (Invitrogen™) (10, 11). Wild-type and variant HPAs were deglycosylated and purified by passing the cell growth supernatant through phenyl-Sepharose and Q-Separose columns (Pharmacia™) The mass and purity of the isolated protein were confirmed by electrospray mass spectrometry and SDS-PAGE. Enzyme concentrations were determined spectrophotographically using an $A^{0.1\%}$ of 2.2 at 280 nm for both wild-type and variant HPA. Detailed purification protocols for HPA have been reported previously (10-12).

Isolation of Montbretins. To obtain sufficient material for kinetic, structural and fragmentation analyses, we have locally grown and harvested corms of Crocosmia "Emily Mackenzie". In a simplified isolation procedure from that previously described (5), corms were minced and extracted two times with methanol overnight, after which this collective extract was dried by rotary evaporation. The crude material thus obtained was then resuspended in water and adsorbed onto a diaion HP-20 column, after which fractions are collected by eluting with 30% and then 50% aqueous acetone, and finally 100% acetone. Using this approach, montbretin isoforms mainly eluted in the 50% aqueous acetone fraction, reducing the amount of material to be purified down into the range of 1%, by mass of the crude extract. The semi-purified material from the HP-20 extraction was then subjected to further purification by reversed phase UPLC using a gradient from 5% to 90% aqueous acetonitrile over 30 min, with monitoring done by UV absorption at 266 nm. In this way, a number of peaks were collected. These included montbretin A (at Rt=20.2 min) and montbretin B (at Rt=21.0 min), as identified by their molecular weights and $^1$H NMR spectra.

A number of additional minor peaks collected in large scale isolations showed $^1$H NMR resonances and masses characteristic of montbretins (13). Of particular interest were two more polar peaks at Rt=17.6 min and Rt=18.7 min. Although not completely purified, these appeared to be two new montbretin isoforms. Montbretin D was purified from the crude 18.7 min fraction by further reversed phase HPLC using 15% aqueous acetonitrile (Rt=25 min). Montbretin E was purified from the 17.6 min fraction, using a similar approach (Rt=17 min). Note that montbretin C has been isolated previously but was not isolated in this particular extraction, possibly due to the differential expression of minor montbretin analogues in different strains of Crocosmia sp. Notable is the apparently ubiquitous nature of montbretins A and B in all species of Crocosmia sp. tested to date. FIG. 1 shows the detailed chemical structures determined for montbretins A-E.

$^1$H and 2D ROESY NMR. The $^1$H and ROESY spectra of MbA were recorded on a Bruker AV-600 spectrometer with a 5 mm CPTCI cryoprobe, using standard Bruker pulse programmes. $^1$H chemical shifts are referenced to the residual DMSO-d$_6$ signal (δ 2.49 ppm). The 2D ROESY data was obtained with 32 scans using 2K (F2)×256 transients (F1) and a mixing time of 300 ms. A 10 mg sample of montbretin A in 600 µL of DMSO-d$_6$ was used in the experiments.

Preparation of Montbretin A Substructures. The fragmentation of Montbretin A to prepare all key derivatives of interest for functional studies was achieved by a series of sequential chemical and enzymatic degradations. Briefly, alkaline methanolysis of MbA with methanolic sodium methoxide produced the MbA-2 derivative and methyl caffeate. This reaction mixture was neutralized with Amberlite IF-120 (H$^+$) and MbA-2 was purified by HPLC on a Jupiter C18 column using a gradient of 20% to 30% aqueous acetonitrile. The chemical structure of MbA-2 was subsequently confirmed by high resolution mass spectrometry and nuclear magnetic resonance spectroscopy. Incubation of MbA with the β-glucosidase from Agrobacterium sp. at room temperature in sodium phosphate buffer (50 mM, pH 6.8), containing 1% bovine serum albumin, resulted in the cleavage of the β-linked terminal glucose of MbA to give derivative MbA-1. Notably in this case, only this one glucose is cleaved, whereas no further processing of the newly revealed terminal β-glucose that results is observed, presumably due to steric hindrance from the large nearby 6-O-caffeic ester moiety. Further β-glucosidase treatment was directed at MbA-2, but surprisingly, despite the presence of the two freely available glucose residues present in this derivative, once again only the terminal glucose was hydrolyzed. TLC analysis showed that MbA-2 is fully converted to MbA-3. This highly selective cleavage pattern would appear to be a consequence of poor binding of the adjacent rhamnose group in the +1 binding subsite of this β-glucosidase.

Further MbA fragmentation was attempted using the commercial multi-enzyme complex naringinase from *Penicillium decumbens*. Unfortunately this enzyme preparation was found to have rhamnosidase, glucosidase and xylosidase activities, leading to the generation of a range of difficult to separate products. To address this problem, we pre-incubated naringinase with the potent active site inactivator, 2-deoxy-2-fluoro-β-D-glucosyl fluoride (14). This approach specifically inhibited the β-glucosidase activity of this enzyme complex, with minimal effect on rhamnosidase activity. Under these conditions, enzymatic hydrolysis of MbA generated mainly MbA-R, with only trace amounts of side products and thereby greatly facilitating HPLC sample purification. Similarly this approach was applied to the MbA-2 derivative to yield the fragment MbA-2R. Subsequent treatment of MbA-R with *Bacillus halodurans* β-xylosidase efficiently and specifically produced the MbA-RX derivative.

By utilizing additional combinations of base treatment and enzymatic hydrolysis by β-glucosidase, modified naringinase and β-xylosidase, we were able to further generate the nine MbA derivatives shown in TABLE 2 for study of the functionality of MbA and its components in detail.

Enzymology

General procedure for enzymatic hydrolysis by *Agrobacterium sp.* glucosidase. Deglucosylation was performed in sodium phosphate buffer (50 mM, pH 6.8) containing 0.1% bovine serum albumin (BSA), and β-glucosidase from *Agrobacterium sp.* (Abg). The reaction mixture was incubated at 37° C. until completion. Enzyme was precipitated by the addition of MeOH solution, and the solution was filtered using Millex (Millipore, PES Membrane filter unit, 0.22 µM). The reaction mixture was evaporated and redissolved in $H_2O$. The resulting solution was purified by HPLC to yield the deglucosylation product.

General procedure for enzymatic cleavage by Naringinase (rhamnosidase). Naringinase was incubated in 50 mM acetate buffer (pH 6.4) at 60° C. for 2 hours, and was added into the reactant solution (50 mM acetate buffer, pH 5.6). Upon consumption of the starting material, enzyme was precipitated by MeOH and removed by Millex filter. The reaction mixture was evaporated and redissolved in $H_2O$, then purified by HPLC.

General procedure for enzymatic cleavage by Xylosidase. Previously de-rhamnosylated glycoside was dissolved in buffer (50 mM sodium phosphate, 50 mM sodium chloride, pH 6.8), and β-xylosidase was added and left to react at room temperature overnight. Enzyme was precipitated by MeOH and removed by Millex filter. The reaction mixture was evaporated, redissolved in $H_2O$ and purified by HPLC.

Fragment Generation

MbA-G

Removal of glucose was performed according to the general procedure for enzyme hydrolysis by *Agrobacterium sp.* β-glucosidase. MbA (49 mg) was dissolved in 400 µL phosphate buffer with 100 µL of 8 mg/mL Abg. The reaction mixture was incubated at 37° C. with addition of a further 100 µL of enzyme after 24 hours. Upon completion and removal of Abg, the resulting solution was purified by HPLC to yield MbA-G as a light yellow powder in 70% yield. $^1$H NMR (400 MHz, methanol-$d_4$): δ 7.40 (d, J=15.8 Hz, 1H), 6.91 (s, 2H), 6.87 (s, 1H), 6.76 (d, J=8.2 Hz, 1H), 6.68 (d, J=8.1 Hz, 1H), 6.23 (s, 1H), 6.19 (s, 1H), 6.05 (d, J=15.8 Hz, 1H), 5.77 (s, 1H), 4.83 (m, 3H), 4.53 (d, J=2.1 Hz, 1H), 4.49 (d, J=7.8 Hz, 1H), 4.35 (d, J=4 Hz, 1H), 4.14-4.23 (m, 2H), 3.94-4.00 (m, 1H), 3.83-3.86 (m, $^1$H), 3.79 (br.s., $^1$H), 3.70-3.76 (m, 2H), 3.55-3.64 (m, 2H), 3.47-3.54 (m, 1H), 3.42-3.45 (m, $^2$H), 3.36 3.40 (m, 2H), 3.29-3.31 (m, 2H), 1.30 (d, J=6.2 Hz, 3H), 1.08 (d, J=6.0 Hz, 3H) 13C NMR (75 MHz, methanol-$d_4$): δ 179.76, 169.08, 165.97, 163.25, 158.50, 158.10, 151.89 (2C), 149.49, 147.13, 146.83, 137.32, 136.28, 128.82, 127.73, 123.03, 116.40, 115.15, 114.87, 109.94 (2C), 107.41, 107.30, 106.26, 102.71, 100.05, 99.97, 95.00, 83.34, 77.77, 75.76, 75.50, 75.30, 75.24, 75.01, 74.02, 73.59, 72.51, 72.21, 72.07, 71.86, 71.72, 70.24, 64.65, 64.36, 18.09, 17.94 HRMS (m/z): [M]+calcd. For $C_{47}H_{54}O_{28}Na$, 1089.2699; found, 1089.2687.

MbA-R

Removal of rhamnose was carried out according to the general procedure for enzymatic cleavage by Naringinase. Naringinase (30 µL of 5.6 mg/mL) was incubated at 60° C. for 2 hours, then was added to 4 mL 17 mM MbA solution in phosphate buffer, pH 5.6. After one day the reaction mixture was purified by HPLC to give MbA-R in 73% yield. $^1$H NMR (400 MHz, methanol-$d_4$): δ 7.32 (d, J=15.8 Hz, 1H), 6.84 (s, 2H), 6.78 (d, J=1.8 Hz, $^1$H), 6.67 (dd, J=8.2, 2.1 Hz, 1H), 6.58 (d, J=8.2 Hz, 1H), 6.15 (d, J=2.1 Hz, 1H), 6.10 (d, J=1.8 Hz, 1H), 5.97 (d, J=16.1 Hz, 1H), 5.59 (s, 1H), 4.74-4.76 (m, 2H), 4.50 (m, 3H), 4.40 (dd, J=11.9, 2.13 Hz, 1H), 4.23 (d, J=2.7 Hz, 1H), 4.12 (dd, J=11.9, 5.5 Hz, 1H), 3.85-3.94 (m, 2H), 3.64-3.69 (m, 2H), 3.47-3.55 (m, 4H), 3.37-3.42 (m, 3H), 3.27-3.35 (m, 4H), 3.18-3.20 (m, 1H), 1.00 (d, J=6.1 Hz, 3H) $^{13}$C NMR (100 MHz, methanol-$d_4$): δ 179.73, 169.05, 166.26, 163.24, 158.52, 157.95, 151.91 14 (2C), 149.54, 147.20, 146.75, 137.43, 136.22, 128.77, 127.69, 123.07, 116.41, 115.12, 114.83, 109.89 (2C), 107.34, 106.60, 106.17, 105.59, 102.67, 100.16, 95.12, 84.72, 84.38, 79.23, 77.91, 77.35, 77.26, 76.00, 75.46, 74.80, 74.08, 72.30, 71.96, 71.43, 71.04, 70.86, 67.46, 64.21, 62.48, 17.84 HRMS (m/z): [M]+calcd. for $C_{47}H_{54}O_{29}Na$, 1105.2648; found, 1105.2677.

MbA-RX

Xylose cleavage followed the general procedure for enzymatic cleavage by xylosidase. MbA-R (43.7 mg) was dissolved in 6 ml buffer and 15 µL of 3.3 mg/mL β-xylosidase was added and incubated at room temperature overnight. Upon HPLC purification MbA-RX was produced in 40% yield. $^1$H NMR (300 MHz, methanol-$d_4$): δ 7.34 (d, J=16.0 Hz, 1H), 6.92 (s, 2H), 6.83 (dd, J=6.7, 1.8 Hz, 1H), 6.71 (dd, J=8.3, 1.9 Hz, 1H), 6.59 (d, J=8.0 Hz, 1H), 6.18 (d, J=2.3 Hz, 1H), 6.09 (d, J=2.1 Hz, 1H), 6.02 (d, J=15.8 Hz, 1H), 5.40 (s, 1H), 4.52 (d, J=7.5 Hz, 1H), 4.36 (d, J=7.8 Hz, 1H), 4.16-4.20 (m, 3H), 3.85-3.97 (m, 3H), 3.76 (dd, J=9.6, 3.7 Hz, 1H), 3.67 (dd, J=12.5, 4.5 Hz, 1H), 3.50-3.55 (m, 2H), 3.37-3.39 (m, 1H), 3.27-3.34 (m, 4H), 1.01 (d, J=6.2 Hz, 3H) $^{13}$C NMR (75 MHz, methanol-$d_4$): δ 179.92, 169.11, 165.86, 163.29, 158.72, 158.51, 149.58 (2C), 147.21, 147.07, 146.81, 137.89, 137.06, 127.76, 123.17, 122.11, 116.42, 115.04, 114.92, 109.51 (2C), 106.63, 106.02, 105.69, 102.79, 99.91, 94.89, 84.84, 84.58, 79.29, 77.98, 77.83, 76.06, 75.42, 74.22, 72.41, 71.95, 71.05, 70.93, 63.89, 62.48, 17.79 HRMS (m/z): [M]+calcd. for $C_{42}H_{45}O_{25}$, 949.2250; found, 949.2272.

MbA-GR

MbA-GR was synthesized by the general procedure for enzyme hydrolysis by *Agrobacterium* sp. β-glucosidase. MbA-R (13.5 mg) was dissolved in 5 mL phosphate buffer with 80 μL of 8 mg/mL Abg at 37° C. Upon completion of reaction the mixture was purified by HPLC to yield MbA-GR as a light yellow powder in 35% yield. $^1$H NMR (300 MHz, methanol-$d_4$): δ 7.31 (d, J=16.0 Hz, 1H), 6.82 (s, 2H), 6.78 (d, J=2.1 Hz, 1H), 6.67 (dd, J=9.0, 1.8 Hz, 1H), 6.58 (d, J=8.2 Hz, 1H), 6.15 (d, J=2.3 Hz, 1H), 6.10 (d, J=2.1 Hz, 1H), 5.95 (d, J=16.0 Hz, 1H), 5.67 (s, 1H), 4.72-4.74 (m, 1H), 4.37-4.45 (m, 2H), 4.25 (dd, J=3.5, 1.3 Hz, 1H), 4.10 (dd, J=12.0, 5.6 Hz, 1H), 3.91 (dd, J=11.4, 5.0 Hz, 1H), 3.75 (dd, J=9.7, 3.5 Hz, 1H), 3.45-3.54 (m, 3H), 3.34-3.40 (m, 3H), 3.27-3.31 (m, 3H), 3.18-3.21 (m, 1H), 0.99 (d, J=6.2 Hz, 3H) $^{13}$C NMR (75 MHz, methanol-$d_4$): δ 179.85, 169.09, 166.05, 163.34, 158.57, 158.15, 151.34 (2C), 149.55, 147.17, 146.79, 137.41, 136.31, 128.85, 127.77, 123.04, 116.41, 115.16, 114.89, 109.92 (2C), 107.47, 107.38, 106.29, 102.81, 100.05, 95.00, 83.63, 77.80, 77.30, 75.56, 75.32, 74.84, 73.63, 72.11, 71.92, 71.88, 70.89, 67.50, 64.37, 17.94 HRMS (m/z): [M]+calcd. for $C_{41}H_{44}O_{24}Na$, 943.2120; found, 943.2134.

MbA-GRX

MbA-GRX was prepared according to the general procedure for enzyme hydrolysis by *Agrobacterium* sp. β-glucosidase. MbA-RX (13.5 mg) was dissolved in 3 mL phosphate buffer with 100 μL of 8 mg/mL Abg and incubated at 37° C. After 24 hours another 100 μL of enzyme was added, then upon completion, the enzyme was precipitated with methanol and removed by filtration. The reaction mixture was evaporated, re-dissolved in $H_2O$ and purified by HPLC to yield MbA-GRX in 30% yield. $^1$H NMR (300 MHz, methanol-$d_4$): δ 7.41 (d, J=16.0 Hz, 1H), 6.98 (s, 2H), 6.90 (d, J=2.1 Hz, 1H), 6.79 (dd, J=8.2, 1.8 Hz, 1H), 6.68 (d, J=8.2 Hz, 1H), 6.24 (d, J=2.1 Hz, 1H), 6.17 (d, J=2.1 Hz, 1H), 6.09 (d, J=16.0 Hz, 1H), 5.60 (s, 1H), 4.33-4.40 (m, 3H), 4.20-4.24 (m, 2H), 3.85-3.95 (m, 3H), 3.34-3.43 (m, 3H), 1.09 (d, J=6.2 Hz, 3H) $^{13}$C NMR (75 MHz, methanol-$d_4$): δ 179.91, 169.37, 165.92, 163.20, 159.07, 159.01, 151.93 (2C), 149.25, 147.05, 146.81, 137.05, 136.96, 127.80, 127.65, 123.14, 116.67, 115.10, 114.93, 111.79, 109.62(2C), 105.60, 104.22, 102.40, 99.94, 94.89, 85.00, 83.88, 75.50, 75.35, 75.30, 71.60, 71.40, 60.85, 17.87 HRMS (m/z): [M]-calcd. for $C_{36}H_{35}O_{20}$, 787.1722; found, 787.1712

Chemical Synthesis of Minimized Inhibitor Compound 10 as a Mimic of MbA-GRX

Pentafluorophenyl caffeate (11): 0.798 g (4.38 mmol) of caffeic acid was dissolved in 10 mL of DMF. 0.57 mL (7.05 mmol) of pyridine was added, followed by 1.21 mL (7.05 mmol) of pentafluorophenyl trifluoroacetate (39). The reaction was stirred at rt for 2 hours. The reaction mixture was then diluted with DCM and washed 5× with 1 M HCl. The material was dried over $MgSO_4$ and concentrated in vacuo. The crude material was purified by silica gel chromatography using an eluent system of pet. ether/EtOAc (6:4). 1.41 g (4.08 mmol) of pentafluorocaffeic ester 11 was isolated as a pale yellow powder upon evaporation of collected fractions (93% yield); $^1$H NMR (300 MHz, acetone-$d_6$) δ 8.59 (s, 1H), 8.41 (s, 1H), 7.88 (d, J=15.9 Hz, 1H), 7.30 (d, J=1.9 Hz, 1H), 7.21 (dd, J=8.1 Hz, J=2.0 Hz, 1H), 6.93 (d, J=8.2 Hz, 1H), 6.60 (d, J=15.9 Hz, 1H); $^{19}$F NMR (282 MHz, acetone-$d_6$) δ −155.56 (d, J=18.4 Hz, 2F), −161.33 (t, 1F), −165.51 (m, 23 2F); $^{13}$C NMR (150 MHz, acetone-$d_6$) δ 163.7, 151.0, 150.1, 146.4, 143.1, 141.5, 141.0, 139.7, 139.4, 138.0, 126.9, 123.9, 116.5, 115.8, 111.0; ESI-MS: m/z: 345 [M-H]$^−$ Propargyl caffeamide (12): 0.33 g (0.94 mmol) of 11 was dissolved in 10 mL of $CH_3Cl$ and 5 mL of DMF. 0.6 mL (0.94 mmol) of propargylamine and 0.13 mL (0.94 mmol) of triethylamine were added. The reaction was stirred at rt for 4 hours and then diluted with DCM and washed 5× with 1 M HCl. The material was dried over $MgSO_4$ and concentrated in vacuo. The resulting material was recrystallized with ethanol/pet. ether. 0.2 g (0.92 mmol) of 12 was isolated as pale orange crystals (97% yield); $^1$H NMR (300 MHz, acetone-$d_6$) δ 8.63 (s, 1H), 8.49 (s, 1H), 7.94 (d, J=15.3 Hz, 1H), 7.42 (d, J=2.1 Hz, 1H), 7.25 (dd, J=8.2 Hz, J=1.8 Hz, 1H), 6.95 (d, J=8.5 Hz, 1H), 6.71 (d, J=15.5 Hz, 1H), 5.57 (br, 1H), 3.65 (m, 2H), 3.55 (t, 1H); $^{13}$C NMR (100 MHz, acetone-$d_6$) δ165.8, 147.3, 145.5, 140.8, 127.4, 121.0, 117.9, 115.6, 114.1, 80.6, 71.4, 28.4; ESI-MS: m/z: 216 [M-H]$^−$ 3',4'-O-Diphenylmethane quercetin: This synthesis followed the procedure of Li et al. (40). 6.15 g (18.2 mmol) of quercetin hydrate was dried at 110° C. under high vacuum for 1 hour. 250 mL of diphenyl ether was then added, along with 5.4 mL (27.3 mmol) of $Ph_2CCl_2$. The mixture was heated to 180° C. and stirred for 3 hours. The material was precipitated by adding 800 mL of pet ether, then filtered and purified by silica gel chromatography with 5% EtOAc/toluene. The material was further purified by recrystallization in chloroform. 6.02 g (12.91 mmol) of 3',4'-O-diphenylmethane quercetin was isolated as a yellow powder (71% yield). $^1$H NMR (300 MHz, $CDCl_3$; δ 12.10 (s, 1H), 9.70 (br, 1H), 8.22 (br, 1H), 7.34 (m, 12H), 6.96 (d, J=6.9 Hz, 1H), 6.33 (d, J=1.8 Hz, 1H), 6.26 (d, J=1.7 Hz, 1H); $^{13}$C NMR (150 MHz, acetone-$d_6$) δ 176.6, 165.0, 162.3, 157.7, 149.3, 148.2, 145.9, 140.8, 137.1, 130.2, 129.3, 126.9, 126.2, 123.9, 118.4, 109.5, 108.7, 104.1, 99.1, 94.5; ESI-MS: m/z: 467 [M+H]$^+$ 3',4'-O-Diphenylmethane-3-(6-O-chlorohexyl) quercetin (13): 1.44 g (3.07 mmol) of 3',4'-O-diphenylmethane quercetin was dissolved in 40 mL of DMF. 0.55 g (4.0 mmol) of $K_2CO_3$ was added. 0.46 mL (3.07 mmol) of 1-bromo-6-chlorohexane was added (41), and the reaction was stirred at rt overnight. The mixture was then diluted with DCM and washed 6× with 1 M HCl, dried over $MgSO_4$, and concentrated in vacuo. The material was purified by silica gel chromatography with 5% EtOAc/toluene. 0.63 g (1.07 mmol) of 13 was isolated as a yellow oil (35% yield). $^1$H NMR (300 MHz, acetone-$d_6$) δ 12.76 (s, 1H), 9.72 (br, 1H), 7.72 (d, J=2.0 Hz, 1H), 7.63 (dd, J=7.4 Hz, J=1.8 Hz, 1H), 7.45 (m, 8H), 7.17 (m, 3H), 6.50 (d, J=1.9 Hz, 1H), 6.26 (d, J=1.9 Hz, 1H), 4.08 (t, 2H), 3.50 (t, 2H), 1.67 (m, 4H), 1.39 (m, 4H); $^{13}$C NMR (100 MHz, acetone-$d_6$) δ 179.5, 164.9, 163.2, 157.8, 156.2, 149.9, 148.1, 140.8, 138.7, 130.2, 129.3, 126.9, 125.6, 124.9, 118.6, 109.6, 109.4, 104.8, 99.4, 94.5, 73.0, 45.6, 30.5, 28.7, 27.2, 26.0; ESI-MS: m/z: 585 [M+H]$^+$, 607 [M+Na]$^+$ 3',4'-O-Diphenylmethane-3-(6-O-chlorohexyl) quercetin (13): 1.44 g (3.07 mmol) of 3',4'-O-diphenylmethane quercetin was dissolved in 40 mL of DMF. 0.55 g (4.0 mmol) of K$_2$CO$_3$ was added. 0.46 mL (3.07 mmol) of 1-bromo-6-chlorohexane was added (41), and the reaction was stirred at rt overnight. The mixture was then diluted with DCM and washed 6× with 1 M HCl, dried over MgSO$_4$, and concentrated in vacuo. The material was purified by silica gel chromatography with 5% EtOAc/toluene. 0.63 g (1.07 mmol) of 13 was isolated as a yellow oil (35% yield). $^1$H NMR (300 MHz, acetone-d$_6$) δ 12.76 (s, $^1$H), 9.72 (br, 1H), 7.72 (d, J=2.0 Hz, 1H), 7.63 (dd, J=7.4 Hz, J=1.8 Hz, 1H), 7.45 (m, 8H), 7.17 (m, 3H), 6.50 (d, J=1.9 Hz, 1H), 6.26 (d, J=1.9 Hz, 1H), 4.08 (t, 2H), 3.50 (t, 2H), 1.67 (m, 4H), 1.39 (m, 4H); $^{13}$C NMR (100 MHz, acetone-d$_6$) δ 179.5, 164.9, 163.2, 157.8, 156.2, 149.9, 148.1, 140.8, 138.7, 130.2, 129.3, 126.9, 125.6, 124.9, 118.6, 109.6, 109.4, 104.8, 99.4, 94.5, 73.0, 45.6, 30.5, 28.7, 27.2, 26.0; ESI-MS: m/z: 585 [M+H]$^+$, 607 [M+Na]$^+$ 3',4'-O-Diphenylmethane-3-(6-O-azidohexyl) quercetin (14): 0.628g (1.07 mmol) of 13 was dissolved in 25 mL of DMF and 0.14 g (2.14 mmol) of sodium azide was added. The mixture was heated to 40° C. and stirred overnight, then diluted with DCM and washed 6× with 1 M HCl, dried over MgSO$_4$, and concentrated in vacuo. The material was purified by silica gel chromatography with 30% EtOAc/toluene. 0.54 g (0.91 mmol) of 14 was isolated as a yellow oil (85% yield). $^1$H NMR (300 MHz, acetone-d$_6$) δ 12.77 (s, 1H), 9,68 (s, 1H), 7.72 (d, J=3.1 Hz, 1H), 7.63 (dd, J=7.6 Hz, 1.7 Hz, 1H), 7.43 (m, 6H), 7.20 (m, 5H), 6.50 (d, J=2.0 Hz, 1H), 6.26 (d, J=1.7 Hz, 1H), 3.50 (t, 2H), 3.22 (t, 2H), 1.67 (m, 4H), 1.37 (m, 4H); $^{13}$C NMR (100 MHz, acetone-d$_6$) δ 179.5, 164.9, 163.2, 157.8, 156.2, 149.9, 148.1, 140.8, 138.7, 130.2, 129.3, 126.9, 125.6, 124.8, 118.6, 109.6, 109.3, 104.8, 99.4, 94.5, 73.1, 51.8, 30.5, 29.3, 27.0, 26.2; ESI-MS: m/z: 592 [M+H]$^+$, 614 [M+Na]$^+$ 3-O-(6-(4-(Caffeamidomethyl)-triazolyl)hexyl) quercetin (10): This click reaction was performed under conditions previously described by Lee et al. (42) 0.11 g (0.18 mmol) of 14 and 0.04 g (0.18 mmol) of 12 were added to a 25 mL RB flask. 4 mL of t-BuOH and 2 mL of DCM were added to dissolve the material. 0.007 g (0.03 mmol) of copper sulfate and 0.016 g (0.08 mmol) of sodium ascorbate were dissolved in 2 mL of H$_2$O and the resulting solution was added to the reaction flask. The mixture was stirred vigorously overnight. The DCM was evaporated in vacuo and the solution was diluted with water. The product was extracted with EtOAc, dried over anhydrous magnesium sulfate, and concentrated in vacuo. This material was then dissolved in 4 mL of acetic acid and 1 mL of water, and the solution was refluxed for 2 hours. The reaction was cooled, diluted with water and the product was extracted with EtOAc, dried over anhydrous magnesium sulfate, and concentrated in vacua. The material was then purified using silica gel chromatography with 50% EtOAc/toluene followed by HPLC with a C18 reverse phase column. 0.046 g (0.07 mmol) of 10 was isolated as a yellow film (40% yield). $^1$H NMR (300 MHz, DMSO-d$_6$) δ 8.54 (s, 1H), 7.83 (d, J=15.7 Hz, 1H), 7.70 (d, J=2.0 Hz, 1H), 7.56 (dd, J=8.1 Hz, 1.9 Hz, 1H), 7.44 (d, J=2.0 Hz, 1H), 7.21 (dd, J=8.0 Hz, 2.0 Hz, 1H), 7.02 (d, J=8.2 Hz, 1H), 6.87 (d, J=8.0 Hz, 1H), 6.65 (d, J=15.5 Hz, 1H), 6.47 (d, J=1.7 Hz, 1H), 6.21 (d, J=1.9 Hz, 1H), 5.45 (br, 1H), 4.10 (t, 2H), 3.57 (t, 2H), 2.85 (m, 2H), 1.75 (m, 4H), 1.44 (m, 4H); $^{13}$C NMR (150 MHz, DMSO-d6) δ 178.2, 172.3, 164.9, 163.5, 157.6, 156.0, 149.2, 148.2, 147.5, 145.6, 140.8, 138.1, 130.8, 129.8, 123.3, 122.8, 122.5, 121.7, 118.4, 118.0, 116.1, 114.6, 104.5, 99.1, 94.5, 75.1, 52.8, 32.6, 30.9, 28.5, 27.2, 26.2; ESI-MS: m/z: 667 [M+Na]$^+$; HRMS (ESI-TOF): m/z calc'd for C$_{33}$H$_{32}$N$_4$O$_{10}$Na: 667.2011 [M+Na]$^+$; found: 667.200

Kinetic Studies. The inhibition constants ($K_I$) of montbretins A-E and MbA substructures for wild-type HPA, along with MbA for H299N HPA were determined by measuring the rates of reactions at different inhibitor and substrate concentrations. Inhibitor concentrations varied from ¼ to 5 times the $K_I$ value in 50 mM sodium phosphate, 100 mM sodium chloride buffer, pH 7.0 at 30° C. 2-Chloro-4-nitrophenyl α-D-maltotrioside (CNP-G3) was used as the substrate in a similar range of concentrations. Initial reaction rates for the release of chloronitrophenolate were measured and the further progress of substrate cleavage monitored continuously. Reactions were performed on a Varian Cary 4000 UV/Vis spectrophotometer at 400 nm and 30° C. Observed reaction rates were fitted directly to various inhibition models using GraFit version 5.0.13 and $K_I$ values were determined. Competitive inhibition provided the best fit in each case.

Structure Determination. To investigate MbA binding in the active site of HPA, co-crystallizations were attempted with wild-type and variant HPAs, with the H299N variant showing the best results. The H299N variant HPA/MbA complex was crystallized using the hanging drop vapor diffusion method (15, 16). Hanging drops consisted of 2 μL of protein solution (12.3 mg/mL) mixed with lyophilized MbA in a 10:1 MbA to protein molecule ratio. To this mixture, 2 μL of reservoir solution containing 58% 2-methylpentane-2,4-diol (MPD) and 100 mM sodium cacodylate (pH 7.5) was added before sealing the coverslip to the well. Under these conditions, high-resolution diffraction quality crystals appeared over the period of one month. In preparation for data collection, crystals were subsequently mounted on diffraction loops and flash frozen in liquid nitrogen.

Diffraction data from a H299N variant HPA/MbA complex crystal were collected on beam line 7-1 at the Stanford Synchrotron Radiation Lightsource at 100 K and a wavelength of 0.98 Å, using an ADSC Quantum 315R CCD detector. This data was processed and reduced using Mosflm (17, 18) and then scaled using Scala (19-21). Observed space group and unit cell dimensions (TABLE 1) indicated that this complex containing crystal was isomorphous with that of wild-type HPA (10), and this latter structure was subsequently used as a starting model for molecular replacement using the CNS software package (22, 23). All subsequent refinement of the structural model of the H299N HPA/MbA complex was accomplished with CNS, using alternating cycles of simulated annealing, positional and thermal factor B refinements. During this process, the complete polypeptide chain for the inhibitor complex was examined periodically with Fo-Fc, 2Fo-Fc and composite omit electron density maps. Where necessary, manual model rebuilding was performed with COOT (24).

The preliminary placement of bound MbA was readily apparent on the basis of difference electron density maps calculated during the refinement of the protein portion of this complex. The MbA inhibitor was built into this well defined residual electron density in the active site, starting with the myricetin group and then adding the extensive array of sugar moieties gradually during subsequent refinement cycles. The HIC-Up database (25, 26) was used to derive initial models and parameter files for the different sugar groups of MbA. Initial models for both myricetin and ethyl caffeate were drawn with the JME Editor (27), with the topology and parameter files for these and the complete MbA molecule being generated using the PRODRG server (28).

Subsequent refinement of both the MbA inhibitor and HPA polypeptide chain placements was carried out to convergence. All inhibitor atoms were refined at full occupancy. At this point, difference electron density maps indicated the presence of an additional N-acetylglucosamine group covalently bound to the side chain of N461 and two MPD molecules hydrogen bonded to the surface of the protein. These molecules were subsequently added to the refinement model along with those of solvent waters identified from further difference electron density maps. The validity of water molecules was monitored on the basis of hydrogen bonding potential to protein and inhibitor atoms, and the refinement of a thermal factor B of <65 Å$^2$. TABLE 1 provides a summary of data collection, structural refinement and polypeptide chain geometry statistics for this structure determination.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

1. Brayer, G. D., Luo, Y., and Withers, S. G. (1995) The structure of human pancreatic alpha-amylase at 1.8 A resolution and comparisons with related enzymes., *Protein Sci.* 4, 1730-1742.

2. Chiasson, J., Josse, R., and Hunt, J. (1994) The Efficacy of Acarbose in the Treatment of Patients with Non-Insulin-Dependent Diabetes Mellitus: A Multicenter, Controlled Clinical Trial, *Annals of internal medicine* 121, 928-935.

3. Mooradian A. D. and Thurman J. E. (1999) Drug Therapy of Postprandial Hyperglycaemia. *Drugs* 57, 19-29.

4. Scott, L. J., and Spencer, C. M. (2000) Miglitol: a review of its therapeutic potential in type 2 diabetes mellitus., *Drugs* 59, 521-549.

5. Tarling, C. A., Woods, K., Zhang, R., Brastianos, H. C., Brayer, G. D., Andersen, R. J., and Withers, S. G. (2008) The Search for Novel Human Pancreatic α-Amylase Inhibitors: High-Throughput Screening of Terrestrial and Marine Natural Product Extracts, *ChemBioChem* 9, 433-438.

6. Ong, K. C., and Khoo, H. E. (2000) Effects of myricetin on glycemia and glycogen metabolism in diabetic rats., *Life Sciences* 67, 1695-1705.

7. Piparo, Lo, E., Scheib, H., Frei, N., Williamson, G., Grigorov, M., and Chou, C. J. (2008) Flavonoids for Controlling Starch Digestion: Structural Requirements for Inhibiting Human α-Amylase, *J. Med. Chem.* 51, 3555-3561.

8. Yoshida, K., Hishida, A., Iida, O., Hosokawa, K., and Kawabata, J. (2008) Flavonol Caffeoylglycosides as α-Glucosidase Inhibitors from Spiraea cantoniensis Flower, *J. Agric. Food Chem.* 56, 4367-4371.

9. Sambrook, J., Fritsch, E., and Maniatis, T. (1989) Molecular Cloning: A Laboratory Manual. Cold Spring Harbor Laboratory Press, Plainview, N.Y.

10. Rydberg, E. H., Sidhu, G., Vo, H. C., Hewitt, J., CÔTÉ, H. C. F., Wang, Y., Numao, S., Macgillivray, R. T. A., Overall, C. M., Brayer, G. D., and Withers, S. G. (1999) Cloning, mutagenesis, and structural analysis of human pancreatic [alpha]-amylase expressed in Pichia pastoris, *Protein Science* 8, 635-643.

11. Numao, S., Maurus, R., Sidhu, G., Wang, Y., Overall, C. M., Brayer, G. D., and Withers, S. G. (2002) Probing the Role of the Chloride Ion in the Mechanism of Human Pancreatic α-Amylase, *Biochemistry* 41, 215-225.

12. Maurus, R. (2005) Incomplete reference Structural and mechanistic studies of chloride induced activation of human pancreatic-amylase, *Protein Science* 14, 743-755.

13. Woods, K. B. (2010) Bioactive natural products. Ph.D. Thesis, University of British Columbia.

14. Withers, S. G., and Aebersold, R. (1995) Approaches to labeling and identification of active site residues in glycosidases., *Protein Sci.* 4, 361-372.

15. Burk, D., Wang, Y., Dombroski, D., and Berghuis, A. (1993) Isolation, Crystallization and Preliminary Diffraction Analyses of Human Pancreatic [alpha]-Amylase, *Journal of Molecular Biology* 250, 1084-1085.

16. Brayer, G. D., Sidhu, G., Maurus, R., Rydberg, E. H., Braun, C., Wang, Y., Nguyen, N. T., Overall, C. M., and Withers, S. G. (2000) Subsite Mapping of the Human Pancreatic α-Amylase Active Site through Structural, Kinetic, and Mutagenesis Techniques, *Biochemistry* 39, 4778-4791.

17. Leslie, A. G. W. (2006) The integration of macromolecular diffraction data., *Acta Cryst* D62, 48-57.

18. Powell, H. R. (1999) The Rossmann Fourier autoindexing algorithm in MOSFLM, *Acta Cryst* D55, 1690-1695.

19. Evans, P. (2006) Scaling and assessment of data quality., *Acta Cryst D* 62, 72-82.

20. Collaborative Computational Project, Number 4. (1994) The CCP4 suite: programs for protein crystallography, *Acta Cryst* D50, 760-763.

21. Winn, M. D., Ballard, C. C., Cowtan, K. D., Dodson, E. J., Emsley, P., Evans, P. R., Keegan, R. M., Krissinel, E. B., Leslie, A. G. W., McCoy, A., McNicholas, S. J., Murshudov, G. N., Pannu, N. S., Potterton, E. A., Powell, H. R., Read, R. J., Vagin, A., and Wilson, K. S. (2011) Overview of the CCP4 suite and current developments., *Acta Cryst* D67, 235-242.

22. Brünger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) Crystallography & NMR system: A new software suite for macromolecular structure determination., *Acta Cryst* D54, 905-921.

23. Brunger, A. T. (2007) Version 1.2 of the Crystallography and NMR system, *Nat Protoc* 2, 2728-2733.

24. Emsley, P., and Cowtan, K. (2004) Coot: model-building tools for molecular graphics, *Acta Cryst* D60, 2126-2132 [doi:10.1107/S0907444904019158]1-7.

25. Kleywegt, G. J., and Jones, T. A. (1998) Databases in protein crystallography., *Acta Cryst* D54, 1119-1131.

26. Kleywegt, G. J. (2007) Crystallographic refinement of ligand complexes., *Acta Cryst* D63, 94-100.

27. Ertl, P. (2010) Molecular structure input on the web, *J Cheminform* 2, 1.

28. Schüttelkopf, A. W., and van Aalten, D. M. F. (2004) PRODRG: a tool for high-throughput crystallography of protein-ligand complexes., *Acta Crystallogr. D Biol. Crystallogr.* 60, 1355-1363.

29. Li, C., Begum, A., Numao, S., Park, K. H., Withers, S. G., and Brayer, G. D. (2005) Acarbose Rearrangement Mechanism Implied by the Kinetic and Structural Analysis of Human Pancreatic α-Amylase in Complex with Analogues and Their Elongated Counterparts, *Biochemistry* 44, 3347-3357.

30. Numao, S., Damager, I., Li, C., Wrodnigg, T. M., Begum, A., Overall, C. M., Brayer, G. D., and Withers, S. G. (2004) In Situ Extension as an Approach for Identifying Novel α-Amylase Inhibitors, *Journal of Biological Chemistry* 279, 48282-48291.

31. Zhang, R., Li, C., Williams, L. K., Rempel, B. P., Brayer, G. D., and Withers, S. G. (2009) Directed " in Situ" Inhibitor Elongation as a Strategy To Structurally Characterize the Covalent Glycosyl-Enzyme Intermediate of Human Pancreatic α-Amylase, *Biochemistry* 48, 10752-10764.

32. Maurus, R., Begum, A., Williams, L. K., Fredriksen, J. R., Zhang, R., Withers, S. G., and Brayer, G. D. (2008) Alternative Catalytic Anions Differentially Modulate Human α-Amylase Activity and Specificity, *Biochemistry* 47, 3332-3344.

33. Goto, T., Horita, M., Nagai, H., Nagatomo, A., Nishida, N., Matsuura, Y., and Nagaoka, S. (2011) Tiliroside, a glycosidic flavonoid, inhibits carbohydrate digestion and glucose absorption in the gastrointestinal tract, *Mol. Nutr. Food Res.* 56, 435-445.

34. The PyMOL Molecular Graphics System, Version 1.3, Schrödinger, LLC.

35. Wicki, J. Personal Communication, *University of British Columbia*, 2009. Vancouver, BC.

36. Lincez, P., and Hii, C. Alpha-amylase inhibitors for Type-2 diabetes: Isolation, Purification, and Kinetic Analysis of Montbretins from *Crocosmia* sp., *Presented at the CDRD, University of British Columbia*, 2008. Vancouver, BC.

37. Sim, L., Quezada-Calvillo, R., Sterchi, E. E., Nichols, B. L. & Rose, D. R. Human intestinal maltase-glucoamylase: crystal structure of the N-terminal catalytic subunit and basis of inhibition and substrate specificity. *J. Mol. Biol.* 375, 782-792 (2008).

38. Sim, L. et al. Structural basis for substrate selectivity in human maltase-glucoamylase and sucrase-isomaltase N-terminal domains. J. Biol. Chem. 285, 17763-17770 (2010).

39. Blaszykowski, C., Sheikh, S., Benvenuto, P., Thompson, M. New Functionalizable Alkyltrichlorosilane Surface Modifiers for Biosensor and Biomedical Applications, *Langmuir*, 28, 2318-2322 (2012).

40. Li, N. G., Shi, Z. H., Tang, Y. P., Yang, J. P., Duan, J. A. An efficient partial synthesis of 4'-O-methylquercetin via regioselective protection and alkylation of quercetin, *Beilstein J. Org. Chem.*, 5 (60) (2009).

41. Mattarei, A. et al. Mitochondriotropic Derivative of Quercetin: A Strategy to Increase the Effectiveness of Polyphenols, *ChemBioChem*, 9, 2633-2642 (2008).

42. Lee, B. Y., Park, S. O., Jeon, H. B., Kim, K. S. A new solvent system for efficient synthesis of 1,2,3-triazoles, *Tetrahedron Lett.*, 47, 5105-5109 (2006).

What is claimed is:

1. A method for inhibiting a mammalian α-amylase, comprising administering a compound of Formula I or a salt thereof to a subject in need thereof,

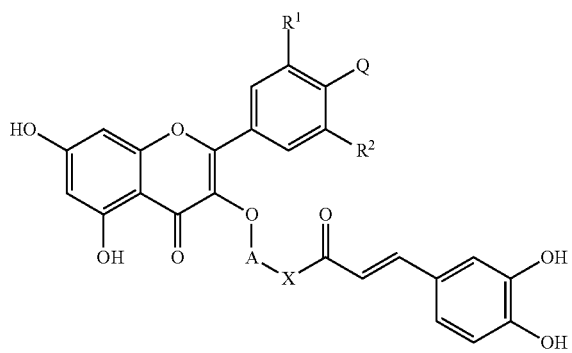

I wherein,
Q is H, OH or a monosaccharide;
$R^1$ is OH;
$R^2$ is H or OH;
X is O or NH; and
A is a disaccharide, a trisaccharide,

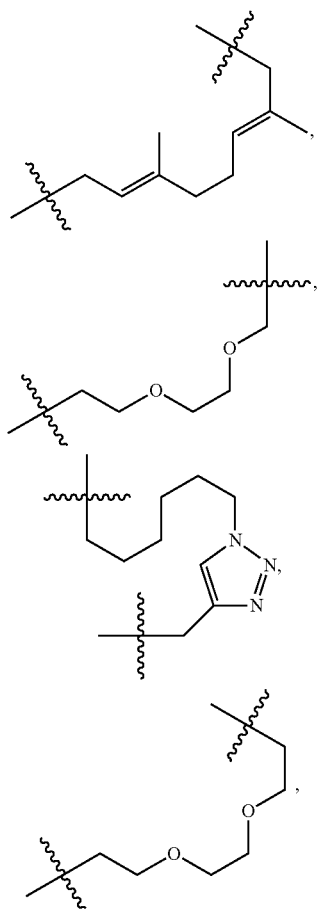

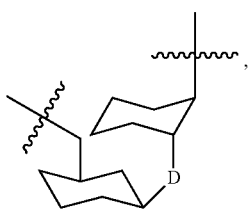

a polyethylene glycol comprised of CH₂CH₂O subunits; a polyprenyl chain; or a 5-15 carbon alkyl; and wherein D is CH$_2$, O, S, or NH.

2. The method of claim 1, wherein A is selected from the following:

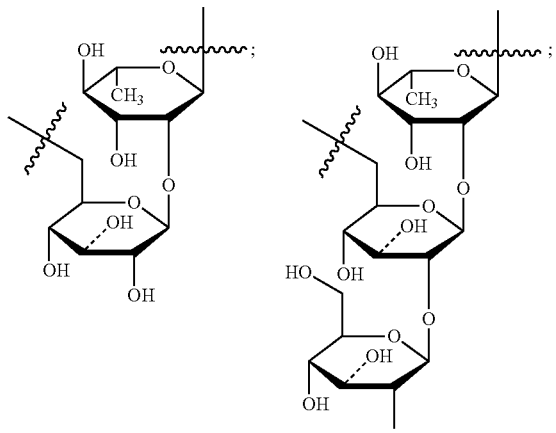

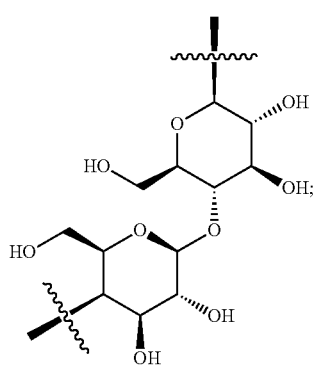

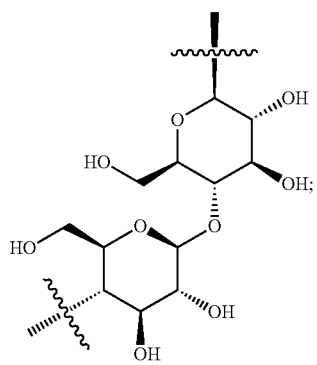

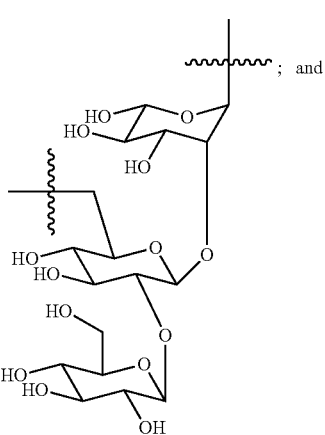

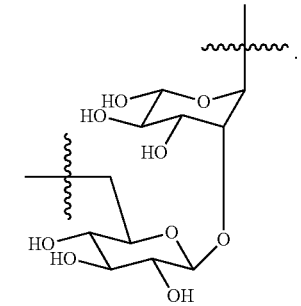

3. The method of claim 1, polyprenyl chain is comprised of 1-3

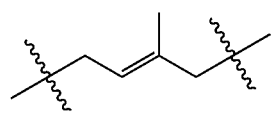 [SMILES: *C/C=C(\C)C*]

subunits.

4. The method of claim 1, wherein the polyethelene glycol comprises 1-5 CH₂CH₂O subunits.

5. The method of claim 1, wherein the polyethelene glycol comprises 2-3 CH₂CH₂O subunits.

6. The method of claim 1, wherein Q is a xylose.

7. The method of claim 1, wherein Q is H.

8. The method of claim 1, wherein Q is OH.

9. The method of claim 1, wherein the mammalian α-amylase is a salivary α-amylase or pancreatic α-amylase.

10. The method of claim 1, wherein the subject is a human.

11. The method of claim 10, wherein the inhibition of the mammalian α-amylase is for the treatment or prophylaxis of dental caries or plaque.

12. The method of claim 10, wherein the inhibition of the mammalian α-amylase is for the treatment of pre-diabetes, diabetes or obesity.

13. The method of claim 10, wherein the administering of the compound of Formula I or a salt thereof to a subject in need thereof is in an effective amount for the treatment of pre-diabetes, diabetes or obesity or for the treatment or prophylaxis of dental caries or plaque.

14. A method for inhibiting a mammalian α-amylase, comprising administering a compound selected from one or more of the following:

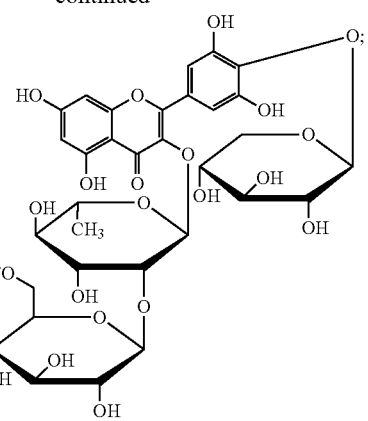

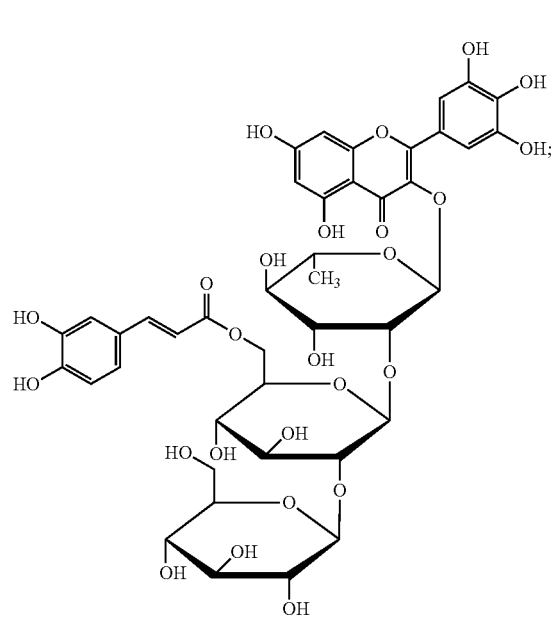

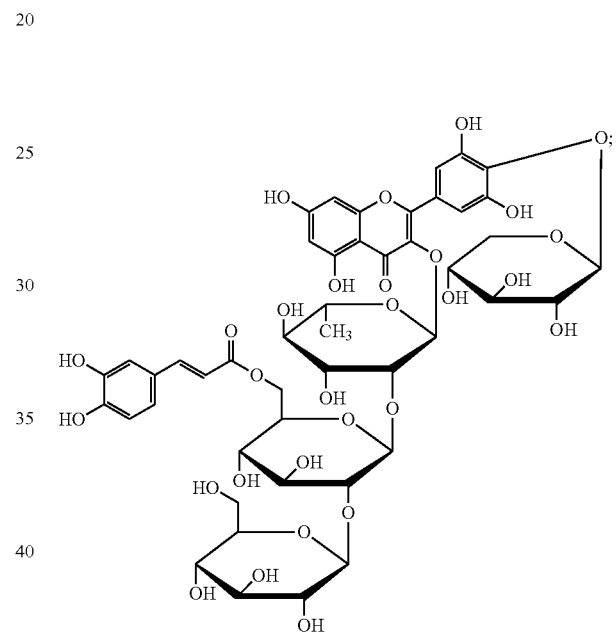

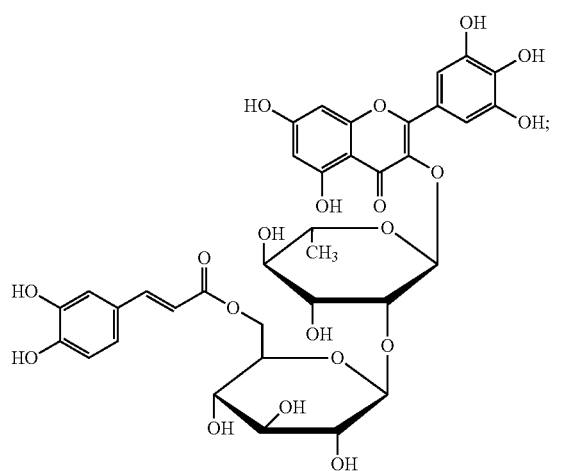

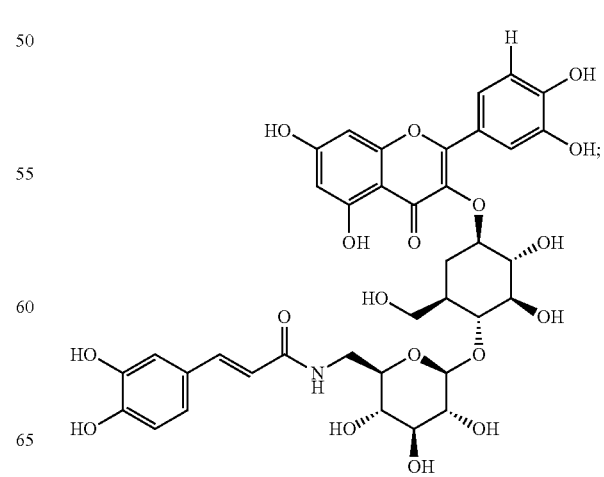

81
-continued
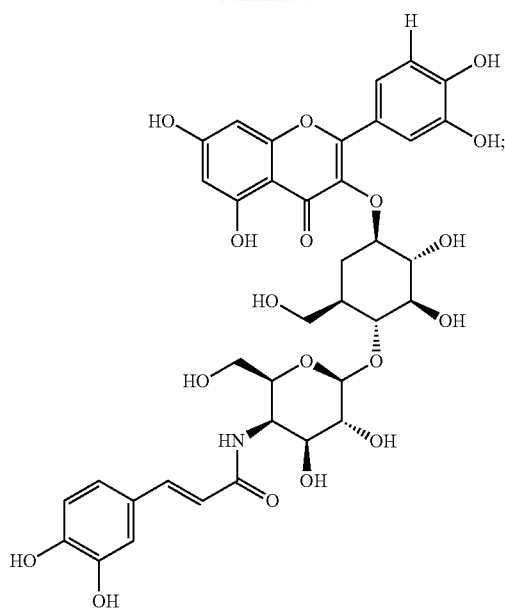
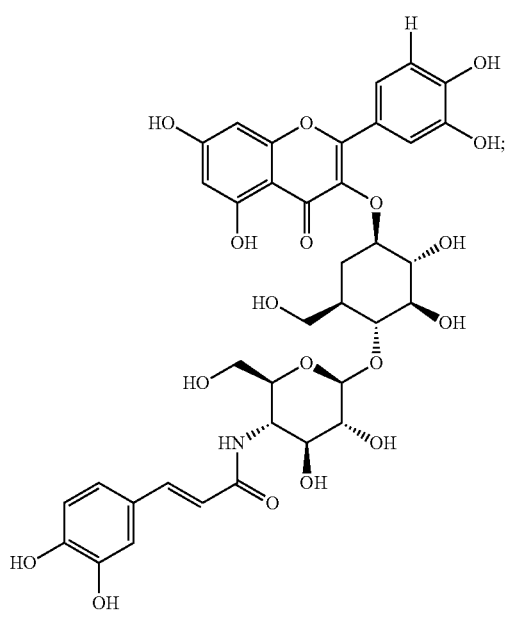
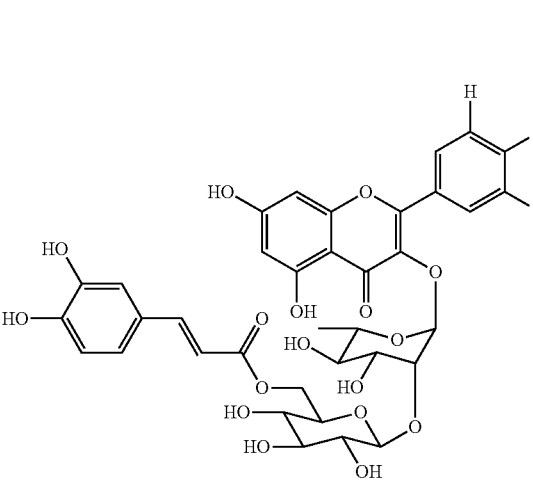
82
-continued
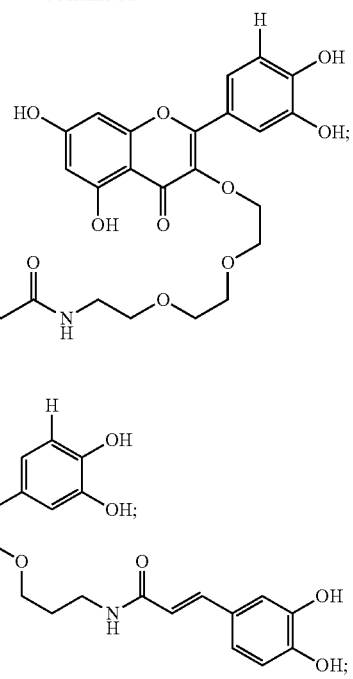
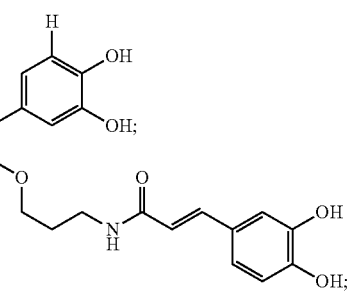
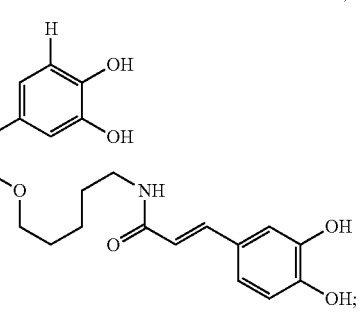
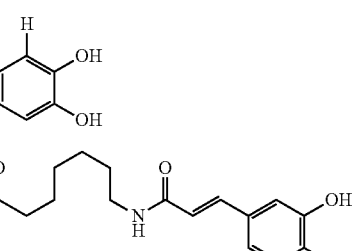

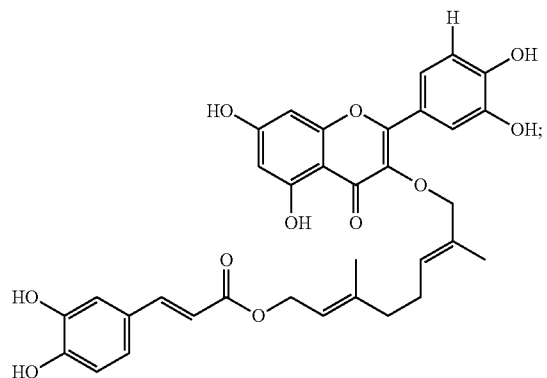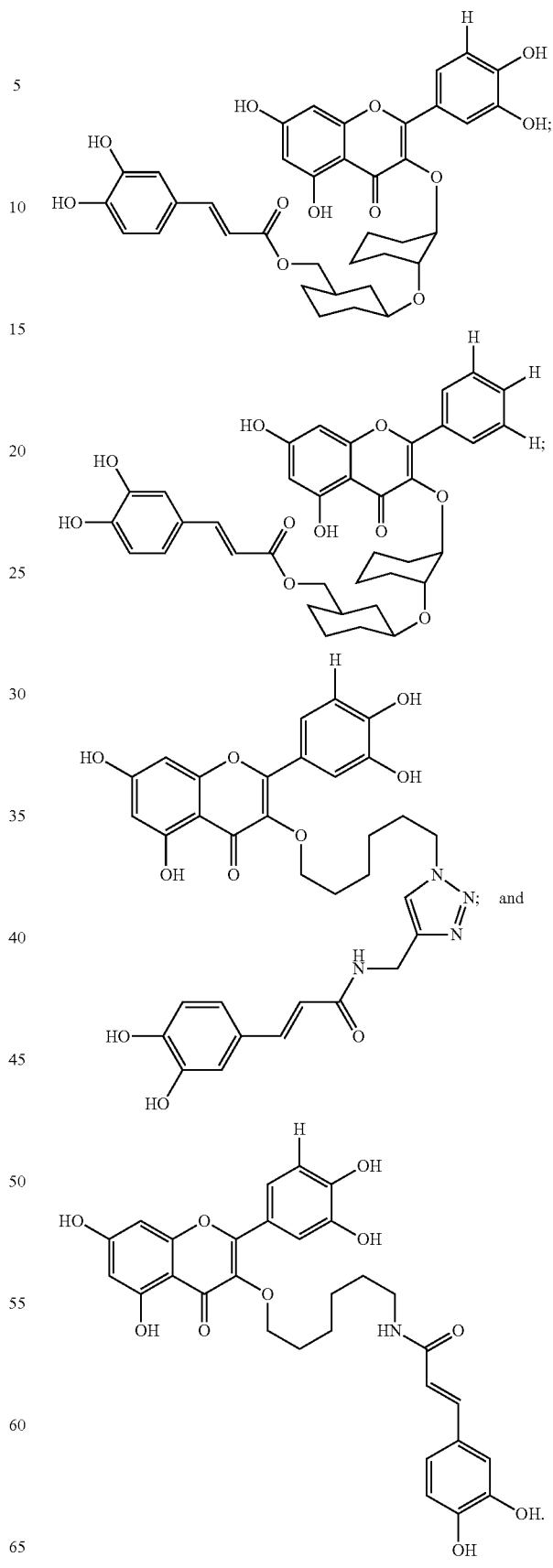

15. The method of claim 14, wherein the administering of the compound is in an effective amount for the treatment of pre-diabetes, diabetes or obesity, or for the treatment or prophylaxis of dental caries or plaque.

16. The method of claim 14, wherein the administering of the compound is for the treatment of pre-diabetes, diabetes or obesity.

* * * * *

UNITED STATES PATENT AND TRADEMARK OFFICE
CERTIFICATE OF CORRECTION

PATENT NO.         : 11,608,353 B2                              Page 1 of 6
APPLICATION NO.    : 16/675535
DATED              : March 21, 2023
INVENTOR(S)        : Stephen G. Withers et al.

It is certified that error appears in the above-identified patent and that said Letters Patent is hereby corrected as shown below:

In the Specification

Column 20,

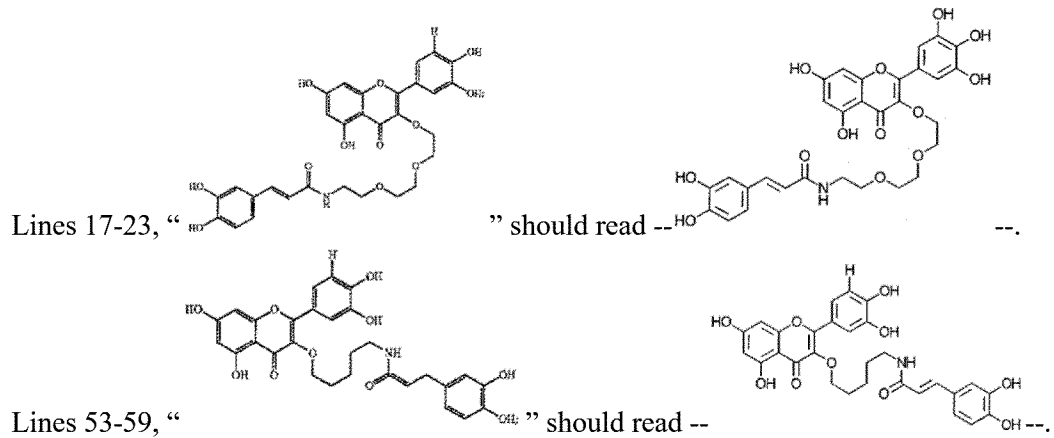

Lines 17-23, " [structure] " should read -- [structure] --.

Lines 53-59, " [structure] " should read -- [structure] --.

Column 21,

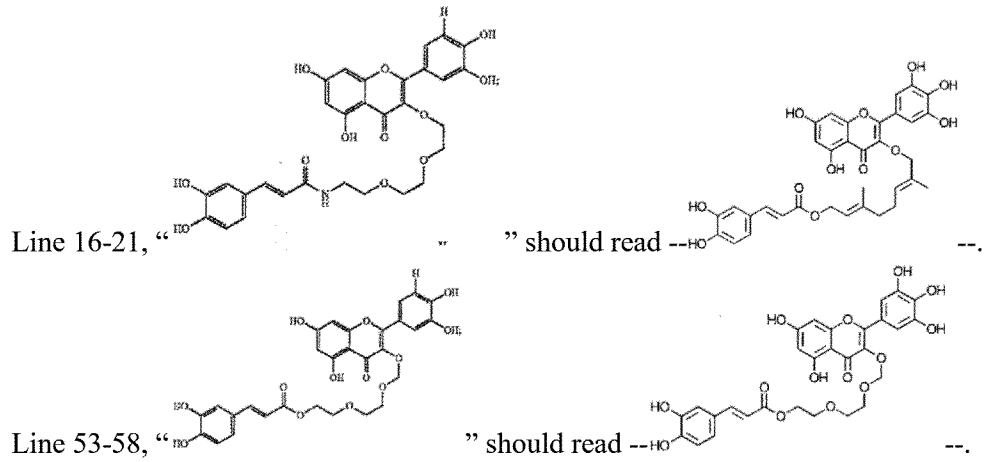

Line 16-21, " [structure] " should read -- [structure] --.

Line 53-58, " [structure] " should read -- [structure] --.

Signed and Sealed this
Twenty-sixth Day of September, 2023

Katherine Kelly Vidal
*Director of the United States Patent and Trademark Office*

CERTIFICATE OF CORRECTION (continued)
U.S. Pat. No. 11,608,353 B2

Column 22,

Lines 15-30, " 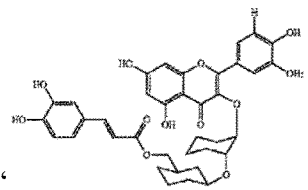 " should read -- 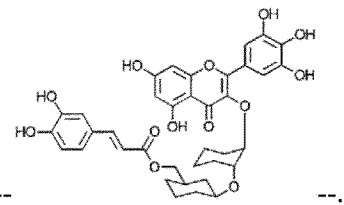 --.

Column 25,

Lines 8-14, " 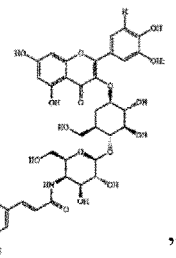 " should read -- 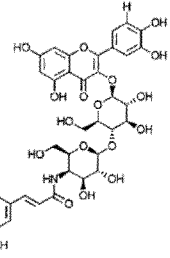 --.

Lines 33-38, " 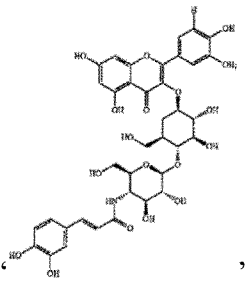 " should read -- 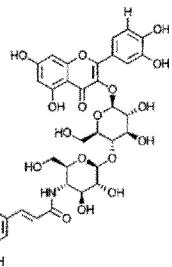 --.

Lines 51-55, " 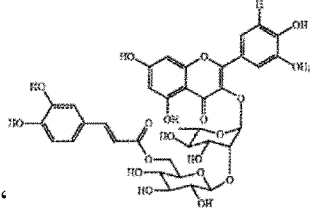 " should read -- 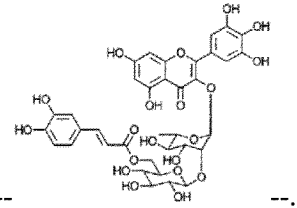 --.

Column 26,

Lines 34-37, " 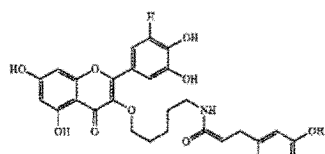 " should read -- 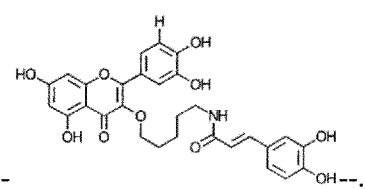 --.

Column 27,

Lines 1-13, " 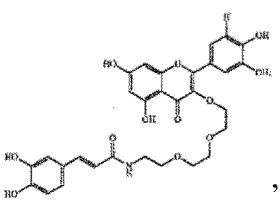 " should read -- 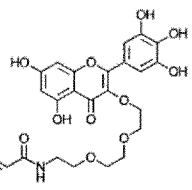 --.

Lines 35-47, " 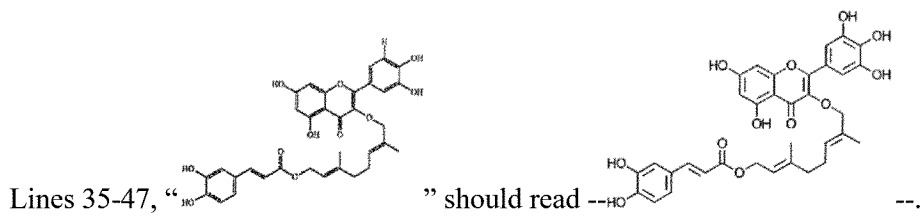 " should read -- --.
Column 28,
Lines 1-13, " 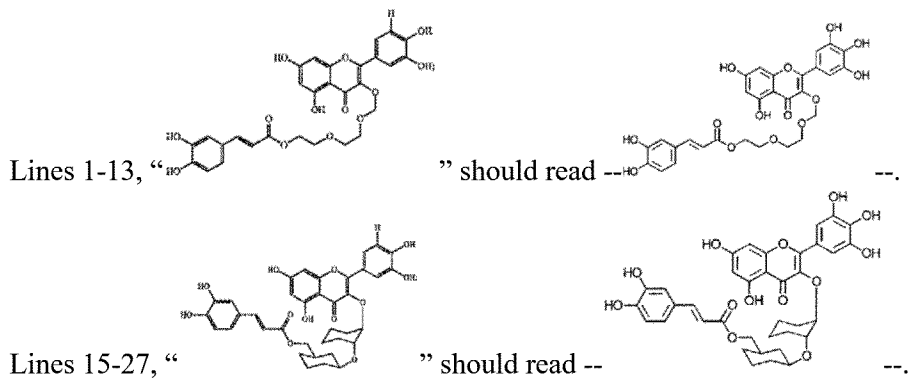 " should read -- --.
Lines 15-27, " " should read -- --.
Column 30,
Lines 57-60, " 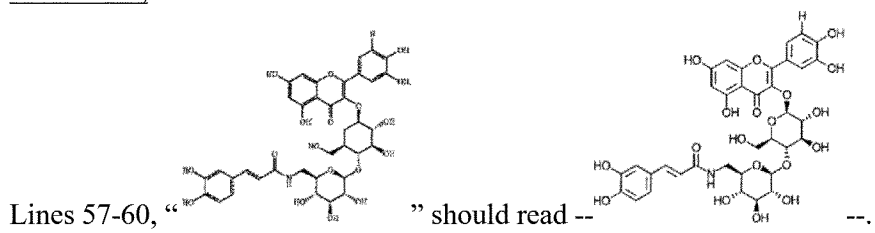 " should read -- --.
Column 31,
Lines 7-13, " 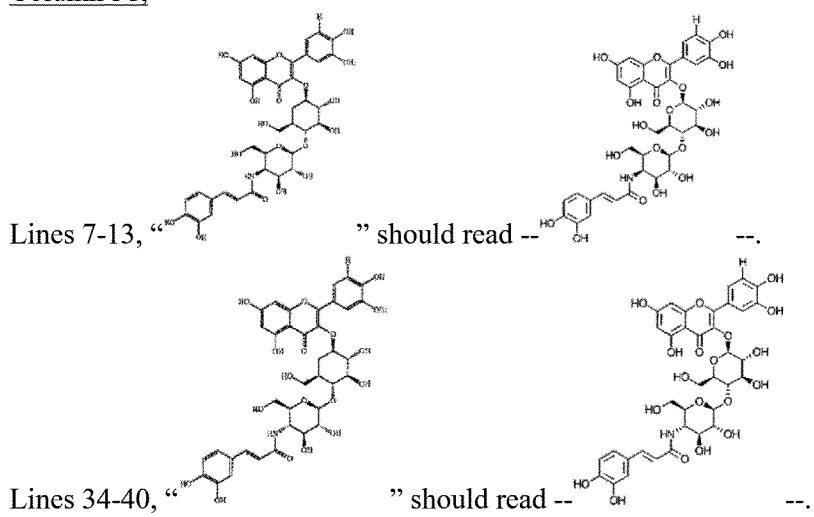 " should read -- --.
Lines 34-40, " " should read -- --.

Lines 53-57, " 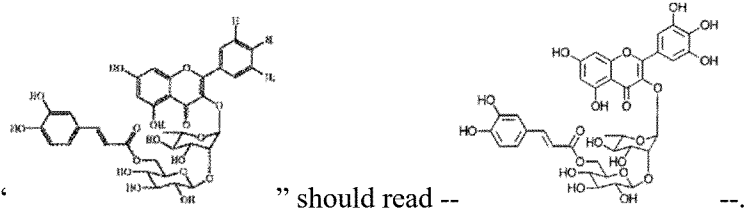 " should read -- --.
Column 32,
Lines 45-49, " 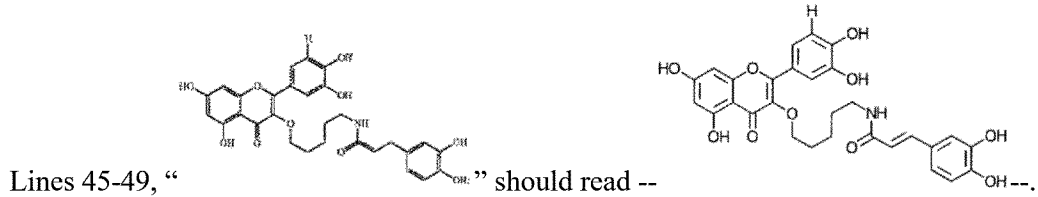 " should read -- --.
Column 33,
Lines 16-18, " 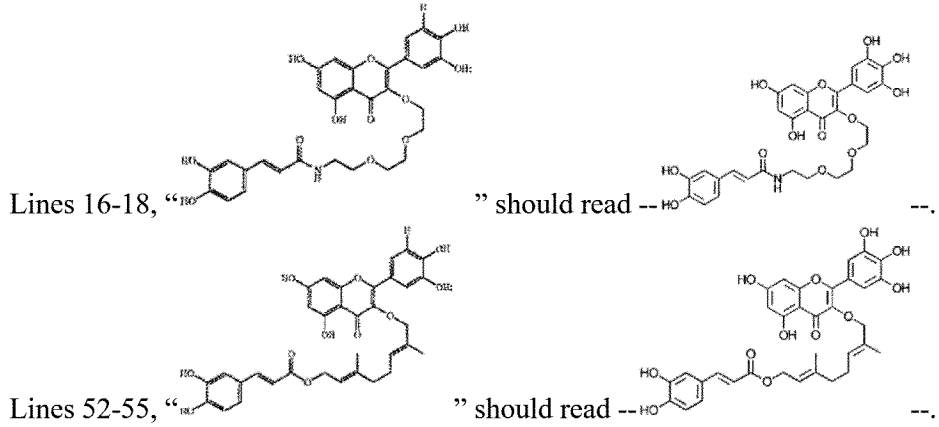 " should read -- --.
Lines 52-55, " " should read -- --.
Column 34,
Lines 16-19, " 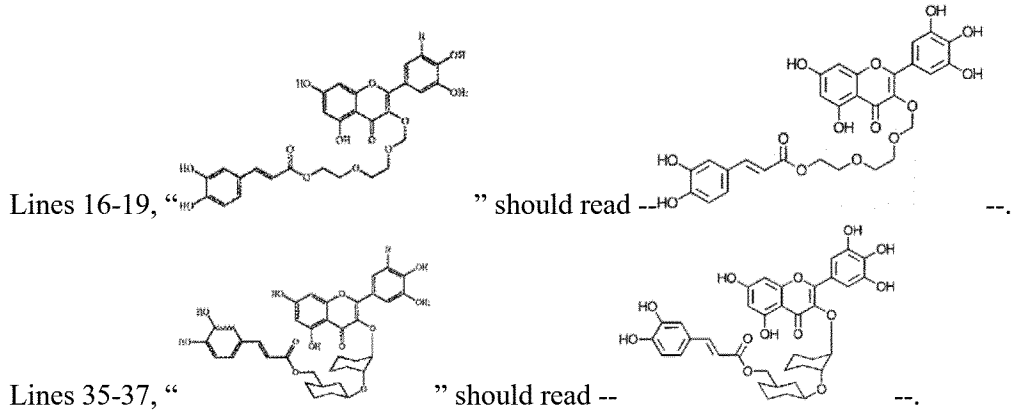 " should read -- --.
Lines 35-37, " " should read -- --.
Column 63,
Line 56, "compounds (6-amino" should read --11 (6-amino--.

CERTIFICATE OF CORRECTION (continued)
U.S. Pat. No. 11,608,353 B2

Column 77,

Lines 27-30, " " should read -- --.

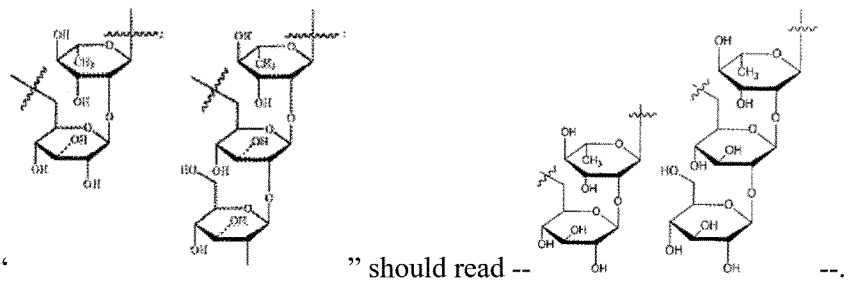

Column 81,

Lines 8-13, " " should read -- --.

Lines 33-35, " " should read -- --.

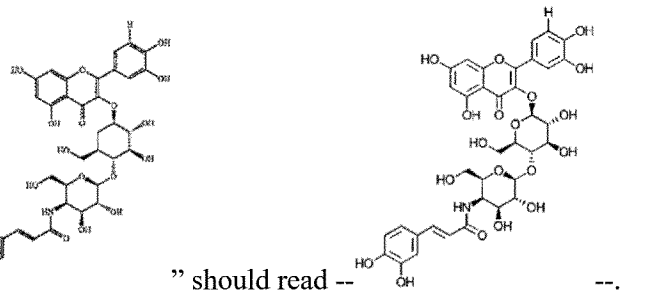

Column 82,

Lines 1-3, " " should read -- --.

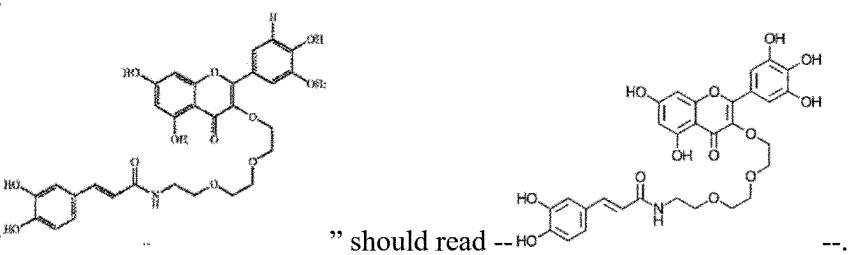

Column 83,

Lines 1-3, " " should read -- --.

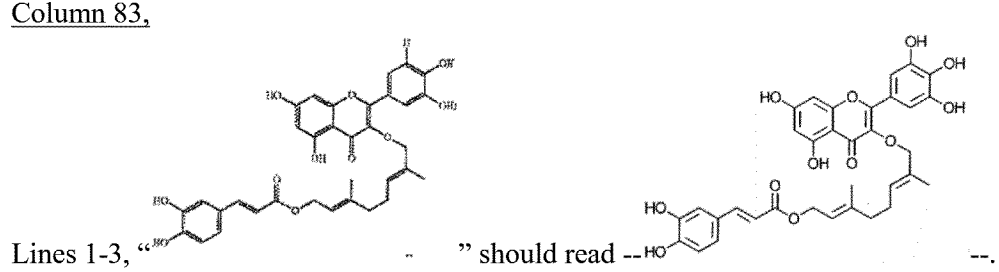

CERTIFICATE OF CORRECTION (continued)
U.S. Pat. No. 11,608,353 B2

Column 84,

Lines 1-3, " 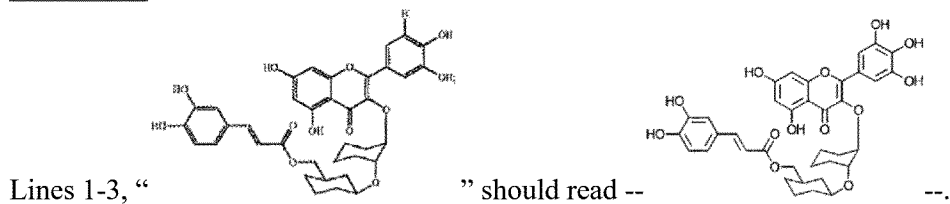 " should read -- -- .